US009220678B2

(12) United States Patent
Kendall et al.

(10) Patent No.: US 9,220,678 B2
(45) Date of Patent: Dec. 29, 2015

(54) COATING METHOD

(75) Inventors: Mark Anthony Fernance Kendall, Chelmer (AU); Germain Fernando, Indooroopilly (AU); Xianfeng Chen, Toowong (AU); Tarl Prow, Collingwood Park (AU)

(73) Assignee: The University of Queensland, St. Lucia (AU)

( * ) Notice: Subject to any disclaimer, the term of this patent is extended or adjusted under 35 U.S.C. 154(b) by 150 days.

(21) Appl. No.: 12/810,298

(22) PCT Filed: Dec. 23, 2008

(86) PCT No.: PCT/AU2008/001903
§ 371 (c)(1),
(2), (4) Date: Nov. 22, 2010

(87) PCT Pub. No.: WO2009/079712
PCT Pub. Date: Jul. 2, 2009

(65) Prior Publication Data
US 2011/0059150 A1 Mar. 10, 2011

(30) Foreign Application Priority Data
Dec. 24, 2007 (AU) .................................. 2007907092

(51) Int. Cl.
*A61M 31/00* (2006.01)
*A61M 5/00* (2006.01)
*A61K 49/00* (2006.01)
*A61K 9/00* (2006.01)
*A61M 37/00* (2006.01)

(52) U.S. Cl.
CPC .......... *A61K 9/0021* (2013.01); *A61M 37/0015* (2013.01); *A61M 2037/0023* (2013.01); *A61M 2037/0046* (2013.01)

(58) Field of Classification Search
CPC ..... A61K 9/0021; A61K 47/38; A61K 39/00; A61M 37/0015
USPC .................... 604/93.01, 173, 272; 264/238.1; 424/9.1, 9.2
See application file for complete search history.

(56) References Cited

U.S. PATENT DOCUMENTS

| 2,881,500 | A | | 4/1959 | Furness |
| 4,702,799 | A | * | 10/1987 | Tuot .............................. 159/48.1 |
| 5,201,992 | A | | 4/1993 | Marcus et al. |
| 5,353,792 | A | | 10/1994 | Lübbers et al. |
| 5,449,064 | A | | 9/1995 | Hogan et al. |
| 5,457,041 | A | | 10/1995 | Ginaven et al. |
| 5,499,474 | A | | 3/1996 | Knooihuizen |
| 5,527,288 | A | | 6/1996 | Gross et al. |
| 5,611,806 | A | | 3/1997 | Jang |
| 5,859,937 | A | | 1/1999 | Nomura |
| 5,922,356 | A | | 7/1999 | Koseki et al. |
| 5,928,207 | A | | 7/1999 | Pisano et al. |
| 6,052,652 | A | | 4/2000 | Lee |
| 6,287,556 | B1 | | 9/2001 | Portnoy et al. |
| 6,299,621 | B1 | | 10/2001 | Fogarty et al. |
| 6,334,856 | B1 | | 1/2002 | Allen et al. |
| 6,352,697 | B1 | | 3/2002 | Cox et al. |
| 6,454,755 | B1 | | 9/2002 | Godshall |
| 6,463,312 | B1 | | 10/2002 | Bergveld et al. |
| 6,478,738 | B1 | | 11/2002 | Hirabayashi et al. |
| 6,503,231 | B1 | | 1/2003 | Prausnitz et al. |
| 6,551,849 | B1 | | 4/2003 | Kenney |
| 6,558,361 | B1 | | 5/2003 | Yeshurun |
| 6,589,202 | B1 | | 7/2003 | Powell |
| 6,591,124 | B2 | | 7/2003 | Sherman et al. |
| 6,743,211 | B1 | | 6/2004 | Prausnitz et al. |
| 6,749,575 | B2 | | 6/2004 | Matriano et al. |
| 6,855,372 | B2 | | 2/2005 | Trautman et al. |
| 6,908,453 | B2 | | 6/2005 | Fleming et al. |
| 6,923,764 | B2 | | 8/2005 | Aceti et al. |
| 6,945,952 | B2 | | 9/2005 | Kwon |
| 7,022,071 | B2 | | 4/2006 | Schaupp et al. |
| 7,045,069 | B2 | | 5/2006 | Ozeryansky |
| 7,097,631 | B2 | | 8/2006 | Trautman et al. |
| 7,169,600 | B2 | | 1/2007 | Hoss et al. |
| 7,211,062 | B2 | | 5/2007 | Kwon |
| 7,250,037 | B2 | | 7/2007 | Shermer et al. |
| 8,052,633 | B2 | | 11/2011 | Kendall |
| 8,062,573 | B2 | | 11/2011 | Kwon |
| 8,734,697 | B2 | | 5/2014 | Chen et al. |
| 8,883,015 | B2 | | 11/2014 | Kendall et al. |
| 2002/0008530 | A1 | | 1/2002 | Kim et al. |
| 2002/0016562 | A1 | | 2/2002 | Cormier et al. |
| 2002/0128599 | A1 | * | 9/2002 | Cormier et al. ............... 604/116 |

(Continued)

FOREIGN PATENT DOCUMENTS

| CN | 101214395 A | 7/2008 |
| CN | 101297989 A | 11/2008 |

(Continued)

OTHER PUBLICATIONS

Gill et al. J. of Controlled Release. Available online Oct. 24, 2006. vol. 117:227-237. 2007.*
Gill et al., J. of Controlled Research. vol. 117:227-237. Published online Oct. 24, 2006).*
International Application Serial No. PCT/AU2008/001903, International Preliminary Report on Patentability issued Jun. 29, 2010, 8 pgs.

(Continued)

*Primary Examiner* — Rodney P Swartz
(74) *Attorney, Agent, or Firm* — Seed IP Law Group PLLC

(57) ABSTRACT

A method of coating a material onto projections provided on a patch. The method includes applying a coating solution containing the material to at least the projections and drying the coating solution to at least the projections using a gas flow.

27 Claims, 32 Drawing Sheets

(56) References Cited

U.S. PATENT DOCUMENTS

| | | |
|---|---|---|
| 2002/0177839 A1* | 11/2002 | Cormier et al. ............... 604/500 |
| 2003/0036710 A1 | 2/2003 | Matriano et al. |
| 2003/0199810 A1 | 10/2003 | Trautman et al. |
| 2004/0039397 A1 | 2/2004 | Weber et al. |
| 2005/0042866 A1 | 2/2005 | Klapproth et al. |
| 2005/0126710 A1 | 6/2005 | Laermer et al. |
| 2005/0137531 A1 | 6/2005 | Prausnitz et al. |
| 2005/0143713 A1 | 6/2005 | Delmore et al. |
| 2005/0197308 A1 | 9/2005 | Dalton et al. |
| 2005/0261632 A1 | 11/2005 | Xu |
| 2006/0015061 A1 | 1/2006 | Kuo et al. |
| 2006/0055724 A1 | 3/2006 | Krawczyk et al. |
| 2006/0074376 A1 | 4/2006 | Kwon |
| 2006/0264782 A1 | 11/2006 | Holmes et al. |
| 2007/0027474 A1 | 2/2007 | Lasner |
| 2007/0060867 A1 | 3/2007 | Xu |
| 2007/0078376 A1 | 4/2007 | Smith |
| 2007/0224252 A1 | 9/2007 | Trautman et al. |
| 2007/0264749 A1 | 11/2007 | Birkmeyer |
| 2007/0270738 A1 | 11/2007 | Wu et al. |
| 2007/0299388 A1 | 12/2007 | Chan et al. |
| 2008/0108959 A1 | 5/2008 | Jung et al. |
| 2008/0245764 A1 | 10/2008 | Pirk et al. |
| 2008/0312669 A1 | 12/2008 | Vries et al. |
| 2010/0221314 A1 | 9/2010 | Matsudo et al. |
| 2011/0028905 A1 | 2/2011 | Takada |
| 2011/0160069 A1 | 6/2011 | Corrie et al. |
| 2011/0223542 A1 | 9/2011 | Kendall |
| 2011/0245776 A1 | 10/2011 | Kendall |
| 2011/0288484 A1 | 11/2011 | Kendall et al. |
| 2012/0027810 A1 | 2/2012 | Chen et al. |
| 2012/0083741 A1 | 4/2012 | Kendall |
| 2012/0083762 A1 | 4/2012 | Kendall |
| 2012/0330250 A1 | 12/2012 | Kuwahara et al. |
| 2013/0190794 A1 | 7/2013 | Kendall et al. |
| 2014/0257188 A1 | 9/2014 | Kendall et al. |

FOREIGN PATENT DOCUMENTS

| | | |
|---|---|---|
| EP | 0 139 286 A2 | 5/1985 |
| EP | 1695734 B1 | 6/2008 |
| EP | 2 327 419 A1 | 6/2011 |
| JP | 2007-260889 A | 10/2007 |
| WO | 91/06571 A1 | 5/1991 |
| WO | 94/24281 A1 | 10/1994 |
| WO | 98/28037 A1 | 7/1998 |
| WO | WO-99/02694 A1 | 1/1999 |
| WO | WO-99/42564 A2 | 8/1999 |
| WO | WO-99/64580 A1 | 12/1999 |
| WO | WO-00/05339 A1 | 2/2000 |
| WO | WO-00/42215 A1 | 7/2000 |
| WO | 00/74764 A1 | 12/2000 |
| WO | WO-00/74763 A2 | 12/2000 |
| WO | WO-01/33614 A1 | 5/2001 |
| WO | WO-01/85207 A2 | 11/2001 |
| WO | WO-02/064193 A2 | 8/2002 |
| WO | WO-02/074173 A1 | 9/2002 |
| WO | WO-02/075794 A1 | 9/2002 |
| WO | 02/085446 A2 | 10/2002 |
| WO | 02/085447 A2 | 10/2002 |
| WO | 02/100476 A2 | 12/2002 |
| WO | 03/020359 A2 | 3/2003 |
| WO | WO-03/026732 A2 | 4/2003 |
| WO | 03/048031 A2 | 6/2003 |
| WO | 03/053258 A1 | 7/2003 |
| WO | WO-03/092785 | 11/2003 |
| WO | WO-03/092785 A1 | 11/2003 |
| WO | 2004/000389 A2 | 12/2003 |
| WO | 2004/024224 A1 | 3/2004 |
| WO | 2005/049108 A2 | 6/2005 |
| WO | WO-2005/060621 A2 | 7/2005 |
| WO | 2005/069736 A2 | 8/2005 |
| WO | WO-2005/072630 A1 | 8/2005 |
| WO | 2005/123173 A1 | 12/2005 |
| WO | WO 2006/055799 A1* | 5/2006 ............ A61M 37/00 |
| WO | 2006/101459 A1 | 9/2006 |
| WO | 2006/108185 A1 | 10/2006 |
| WO | 2006/116281 A2 | 11/2006 |
| WO | WO-2006138719 A2 | 12/2006 |
| WO | 2007/002521 A2 | 1/2007 |
| WO | WO-2007/002123 A2 | 1/2007 |
| WO | 2007/012114 A1 | 2/2007 |
| WO | 2007/030477 A2 | 3/2007 |
| WO | WO-2007/054090 A1 | 5/2007 |
| WO | WO-2007/061781 A1 | 5/2007 |
| WO | WO-2007/070004 A2 | 6/2007 |
| WO | WO-2007/080427 A2 | 7/2007 |
| WO | WO-2007/127976 A2 | 11/2007 |
| WO | WO-2008/010681 A1 | 1/2008 |
| WO | WO-2008/011625 A2 | 1/2008 |
| WO | WO-2008/053481 A1 | 5/2008 |
| WO | 2008/069566 A1 | 6/2008 |
| WO | 2009/040548 A1 | 4/2009 |
| WO | WO-2009/066763 A1 | 5/2009 |
| WO | 2009/081122 A1 | 7/2009 |
| WO | WO-2009079712 | 7/2009 |
| WO | 2009/097660 A1 | 8/2009 |
| WO | WO-2009/140735 A1 | 11/2009 |
| WO | WO-2010042996 | 4/2010 |
| WO | 2010/071918 A1 | 7/2010 |
| WO | WO-2010/109471 A1 | 9/2010 |
| WO | 2011/105496 A1 | 9/2011 |
| WO | 2011/116388 A1 | 9/2011 |

OTHER PUBLICATIONS

International Application Serial No. PCT/AU2008/001903, International Search Report mailed Feb. 20, 2009, 5 pgs.

International Application Serial No. PCT/AU2008/001903, Written Opinion mailed Feb. 20, 2009, 6 pgs.

Aichele, P., et al., "Antiviral Cytotoxic T Cell Response Induced by In Vivo Priming With a Free Synthetic Peptide", *J. Exp. Med.*, 171, (1990), 1815-1820.

Albert, M. L., et al., "Dendritic cells acquire antigen from apoptotic cells and induce class I-restricted CTLs", *Nature*, 392(6671), (1998), 86-89.

Albert, M. L., et al., "Tumor-specific killer cells in paraneoplastic cerebellar degeneration", *Nature Medicine*, 4(11), (1998), 1321-1324.

Althanasopoulos, T., et al., "Gene Therapy Vectors Based on Adeno-Associated Virus: Characteristics and Applications to Acquired and Inherited Diseases (Review)" (Abstract Only), *Int. J. Mol. Med.*, 6(4), (2000), 1 pg.

Bachmann, M. F., et al., "Dendritic cells process exogenous viral proteins and virus-like particles for class I presentation to $CD8^+$ cytotoxic T lymphocytes", *Eur. J. Immunol.*, 26, (1996), 2595-2600.

Camilli, A., et al., "*Listeria monocytogenes* Mutuants Lacking Phosphatidylinositol-specific Phospholipase C Are Avirulent", *J. Exp. Med.*, 173, (1991), 751-754.

Cormier, M., et al., "Transdermal delivery of desmopressin using a coated microneedle array patch system", *Journal of Controlled Release*, 97, (2004), 503-511.

Cox, J. C., et al., "Adjuvants-a classification and review of their modes of action", *Vaccine*, 15(3), (1997), 248-256.

Gao, X.-M., et al., "Priming of Influenza Virus-Specific Cytotoxic T Lymphocytes Vivo by Short Synthetic Peptides", *The Journal of Immunology*, 147(10), (1991), 3268-3273.

Gill, H. S., et al., "Coated microneedles for transdermal delivery", *Journal of Controlled Release*, 117, (2007), 227-237.

Gill, H. S., et al., "Coating Formulations for Microneedles", *Pharamaceutical Research*, 24(7), (2007), 1369-1380.

Jondal, M., et al., "MHC Class I-Restricted CTL Responses to Exogenous Antigens", *Immunity*, 5, (1996), 295-302.

Kay, M. A., et al., "Viral vectors for gene therapy: the art of turning infectious agents into vehicles of therapeutics", *Nature Medicine*, 7(1), (2001), 33-40.

Kuzu, H., et al., "In vivo priming effect during various stages of ontogeny of an influenza A virus nucleoprotein peptide", *Eur. J. Immunol.*, 23, (1993), 1397-1400.

(56) References Cited

OTHER PUBLICATIONS

Matriano, J. A., et al., "Macroflux® Microprojection Array Patch Technology: A New and Efficient Approach for Intracutaneous Immunization", *Pharmaceutical Research*, 19(1), (2002), 63-70.

Mengaud, J., et al., "Expression in *Escherichia coli* and Sequence Analysis of the Listeriolysin O Determinant of *Listeria monocytogenes*", *Infection and Immunity*, 56(4), (1988), 766-772.

Moore, M. W., et al., "Introduction of Soluable Protein into the Class I Pathway of Antigen Processing and Presentation", *Cell*, 54, (1988), 777-785.

Palmer, M., et al., "Streptolysin O: A Proposed Model of Allosteric Interaction between a Pore-Forming Protein and Its Target Lipid Bilayer", *Biochemistry*, 37(8), (1998), 2378-2383.

Portnoy, D. A., et al., "Capacity of Listeriolysin O, Streptolysin O, and Perfringolysin O to Mediate Growth of *Bacillus subtilis* within Mammalian Cells", *Infection and Immunity*, 60(7), (1992), 2710-2717.

Rossjohn, J., et al., "Structure of a Cholesterol-Binding, Thiol-Activated Cytolysin and a Model of Its Membrane Form", *Cell*, 89(5), (1997), 685-692.

Schulz, M., et al., "Peptide-induced antiviral protection by cytotoxic T cells", *Proc. Natl. Acad. Sci. USA*, 88(3), (1991), 991-995.

Vigna, E., et al., "Lentiviral vectors: excellent tolls for experimental gene transfer and promising candidates for gene therapy", *The Journal of Gene Medicine*, 2(5), (2000), 308-316.

Walther, W., et al., "Viral Vectors for Gene Transfer—A Review of Their Use in the Treatment of Human Diseases", *Drugs*, 60(2), (2000), 249-271.

Wu, N., et al., "Production of viral vectors for gene therapy applications", *Current Opinion in Biotechnology*, 11(2), (2000), 205-208.

Zhou, F., et al., "Liposome-Mediated Cytoplasmic Delivery of Proteins: An Effective Means of Accessing the MHC Class I-Restricted Antigen Presentation Pathway", *Immunomethods*, 4(3), (1994), 229-235.

Dreyer, E. C., "Microneedles: Microprocessing in Medicine", Final Presentation, ENMA 465 Project, (May 10, 2004), 23 pgs.

Gardeniers, H. J. G. E., et al., "Silicon Micromachined Hollow Microneedles for Transdermal Liquid Transport", *Journal of Microelectromechanical Systems*, 12(6), (2003), 855-862.

Lin, L., et al., "Silicon-Processed Microneedles", *Journal of Microelectromechanical Systems*, 8(1), (1999), 78-84.

Stoeber, B., et al., "Arrays of Hollow Out-of-Plane Microneedles for Drug Delivery", *Journal of Microelectromechanical Systems*, 14(3), (2005), 472-479.

Tao, J., et al., "A systematic study of dry etch process for porfile control of silicon tips", *Microelectronic Engineering*, 78-79, (2005), 147-151.

Anderson, "Cutaneous Microdialysis: Is it Worth the Sweat?," *Journal of Investigative Dermatology* 126:1207-1209, 2006.

Feng et al., "Molecular Biomarkers for Cancer Detection in Blood and Bodily Fluids," *Critical Reviews in Clinical Laboratory Sciences* 43(5-6):497-560, 2006.

International Preliminary Report on Patentability, completed Nov. 14, 2012, for International Application No. PCT/AU2011/000890, 6 pages.

International Preliminary Report on Patentability, mailed Jun. 7, 2006, for International Application No. PCT/GB2005/000336, 11 pages.

International Search Report, mailed Oct. 25, 2011, for International Application No. PCT/AU2011/000890, 4 pages.

International Search Report, mailed Feb. 20, 2013, for International Application No. PCT/AU2012/001289, 13 pages.

Ito et al., "Feasibilty of microneedles for percutaneous absorption of insulin," *European Journal of Pharmaceutical Sciences* 29:82-88, 2006.

Ito et al., "Self-dissolving microneedles for the percutaneous absorption of EPO in mice," *Journal of Drug Targeting* 14(5):255-261, 2006.

Ito et al., "Evaluation of self-dissolving needles containing low molecular weight heparin (LMWH) in rats," *International Journal of Pharmaceutics* 349:124-129, 2008.

Kendall et al., "The mechanical properties of the skin epidermis in relation to targeted gene and drug delivery," *Biomaterials* 28:4968-4977, 2007.

Kwon, "In Vitro Evaluation of Transdermal Drug Delivery by a Micro-needle Patch," Controlled Release Society $31^{st}$ Annual Meeting, 2004, 2 pages.

Kwon, "Acne Treatment by a Dissolvable Micro-Needle Patch," TheraJect Inc., 2006, 2 pages.

Kwon et al., "Rapid Intradermal Drug Delivery by a Dissolvable Micro-Needle Patch," Controlled Release Society $32^{nd}$ Annual Meeting, 2005, 2 pages.

Kwon et al., "In Vitro Modeling of Transdermal PTH Delivery by Dissolving Micro-needle Patch," TheraJect Inc., 2007, 2 pages.

Lee et al., "Dissolving microneedles for transdermal drug delivery," *Biomaterials* 29:2213-2124, 2008.

Miyano et al., "Sugar Micro Needles as Transdermic Drug Delivery System," *Biomedical Microdevices* 7(3):185-188, 2005.

Miyano et al., "Hydrolytic Microneedles as Transdermal Drug Delivery System," *Transducer & Eurosensors '07*, The $14^{th}$ International Conference on Solid-State Sensors, Actuators and Microsystems, Lyon, France, Jun. 10-14, 2007, 4 pages.

Mukerjee et al., "Microneedle array for transdermal biological fluid extraction and in situ analysis," *Sensor and Actuators A* 114:267-275, 2004.

Office Action, issued Feb. 17, 2012, for Chinese Patent Application No. 200980104635.3, 7 pages. (English Translation).

Oh et al., "Intradermal influenza vaccine delivery using skin-penetrating dissolvable vaccine microneedles," 2006 AAPS Annual Meeting and Exposition, 1 page.

Oh et al., "Demonstration of Dose-controlled Delivery by Dissolvable Micro-needle Arrays," $34^{th}$ Annual CRS Conference, Jun. 2007, 2 pages.

Park et al., "Biodegradable polymer microneedles: Fabrication, mechanics and transdermal drug delivery," *Journal of Controlled Release* 104:51-66, 2005.

Park et al., "Polymer Microneedles for Controlled-Release Drug Delivery," *Pharmaceutical Research* 23(5):1008-1019, 2006.

Park et al., "Towards the silicon nanowire-based sensor for intracellular biochemical detection," *Biosensors and Bioelectronics* 22:2065-2070, 2007.

Silver et al., "Viscoelastic Properties of Young and Old Human Dermis: A Proposed Molecular Mechanism for Elastic Energy Storage in Collagen and Elastin," *J. Appl. Polym Sci* 86:1978-1985, 2002.

Sullivan et al., "Minimally Invasive Protein Delivery with Rapidly Dissolving Polymer Microneedles," *Adv. Mater.* 20:933-938, 2008.

Tsuchiya et al., "Development of Blood Extraction System for Health Monitoring System," *Biomedical Microdevices* 7(4):347-353, 2005.

Tyagi et al., "Molecular Beacons: Probes that Fluoresce upon Hybridization," *Nature Biotechnology* 14:303-308, 1996.

Wang et al., "Label-free hybridization detection of a single nucleotide mismatch by immobilization of molecular beacons on an agarose film," *Nucleic Acids Research* 30(12):e61, 2002. (9 pages).

Widera et al., "Effect of Delivery parameter on immunization to ovalbumin following intracutaneous administration by a coated microneedle array patch system," *Vaccine* 24:1653-1664, 2006.

Yuan et la., "Measuring microelastic properties of stratum corneum," *Colloids and Surfaces B: Biointerfaces* 48:6-12, 2006.

Zheng et al., "Multiplexed electrical detection of cancer markers with nanowire sensor arrays," *Nature Biotechnology* 23(10):1294-1301, 2005.

\* cited by examiner

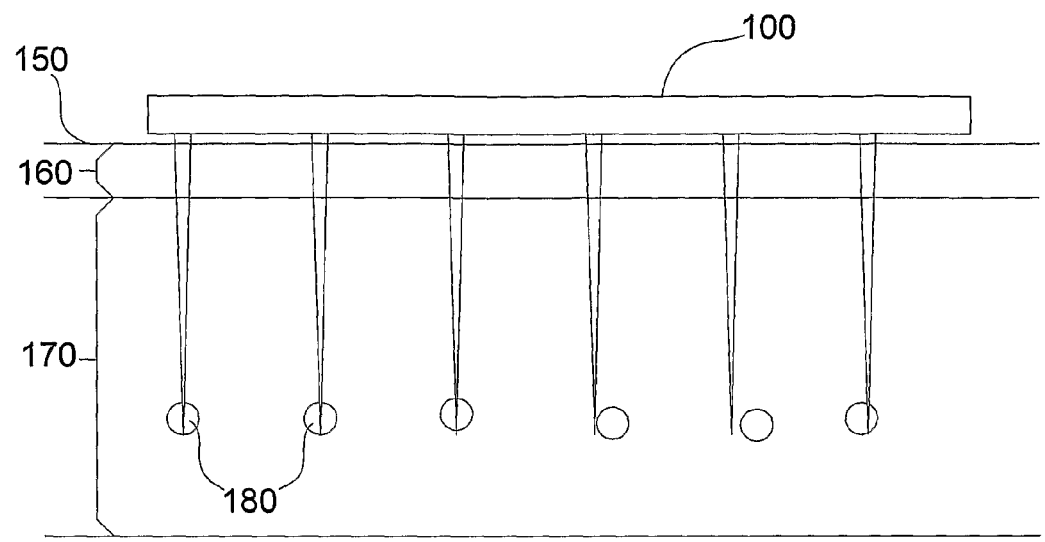
Fig. 1C
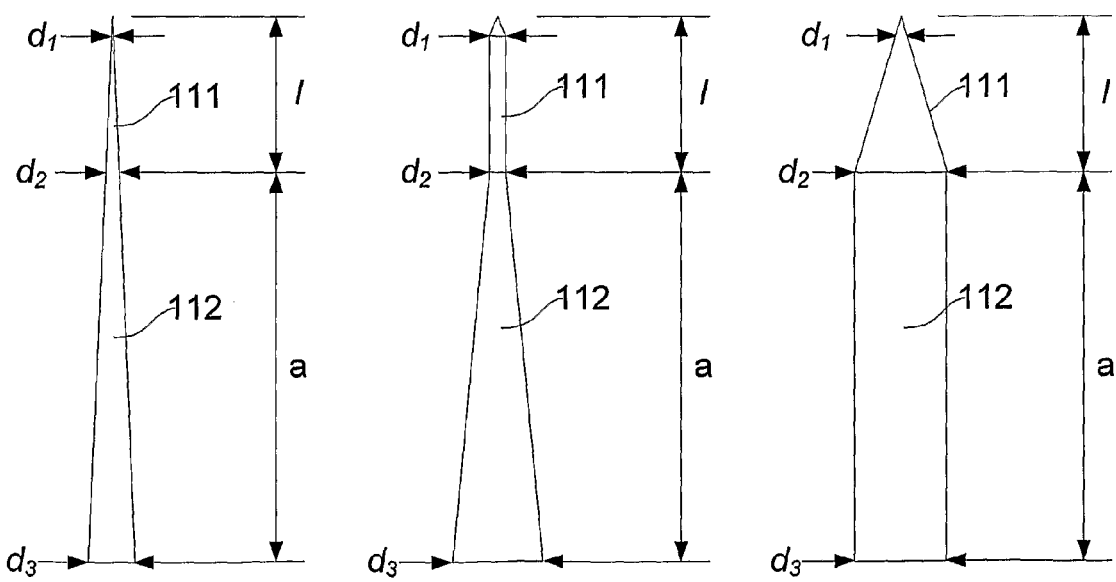
Fig. 1D  Fig. 1E  Fig. 1F

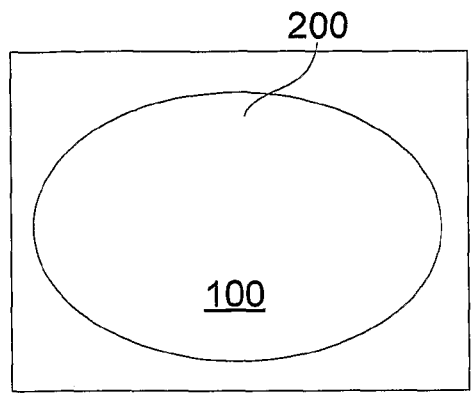
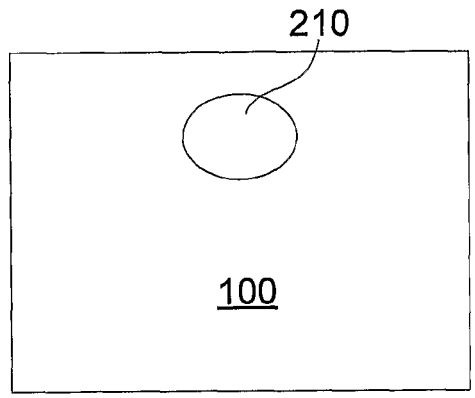
Fig. 2A	Fig. 2B
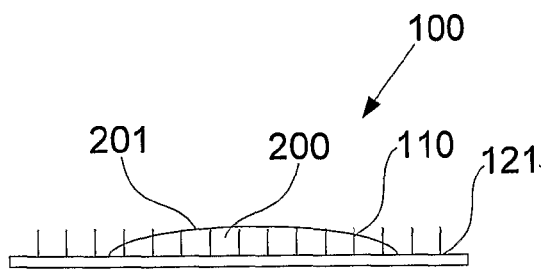
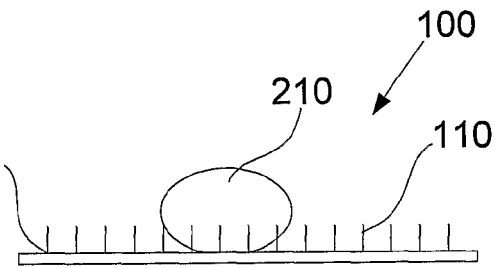
Fig. 2C	Fig. 2D
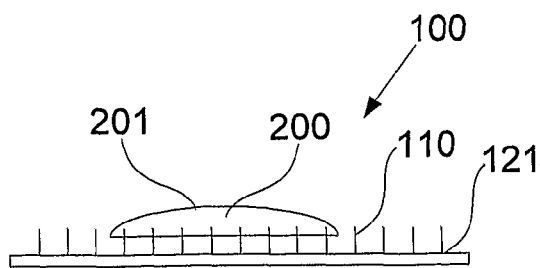
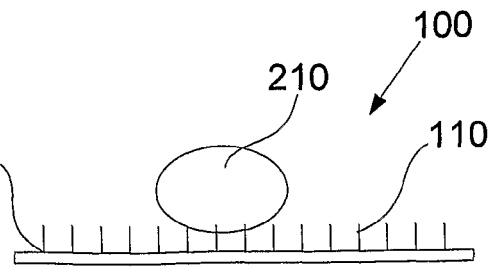
Fig. 2E	Fig. 2F

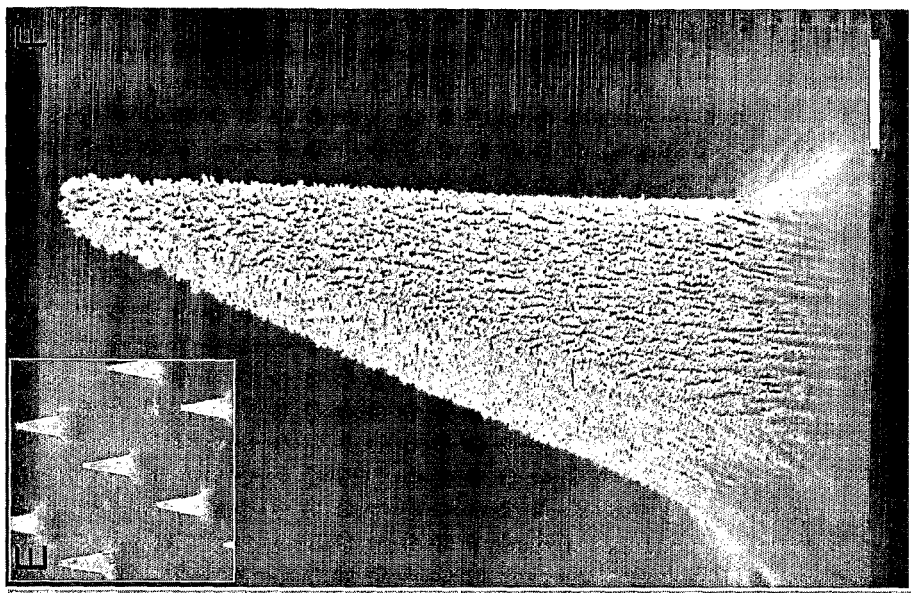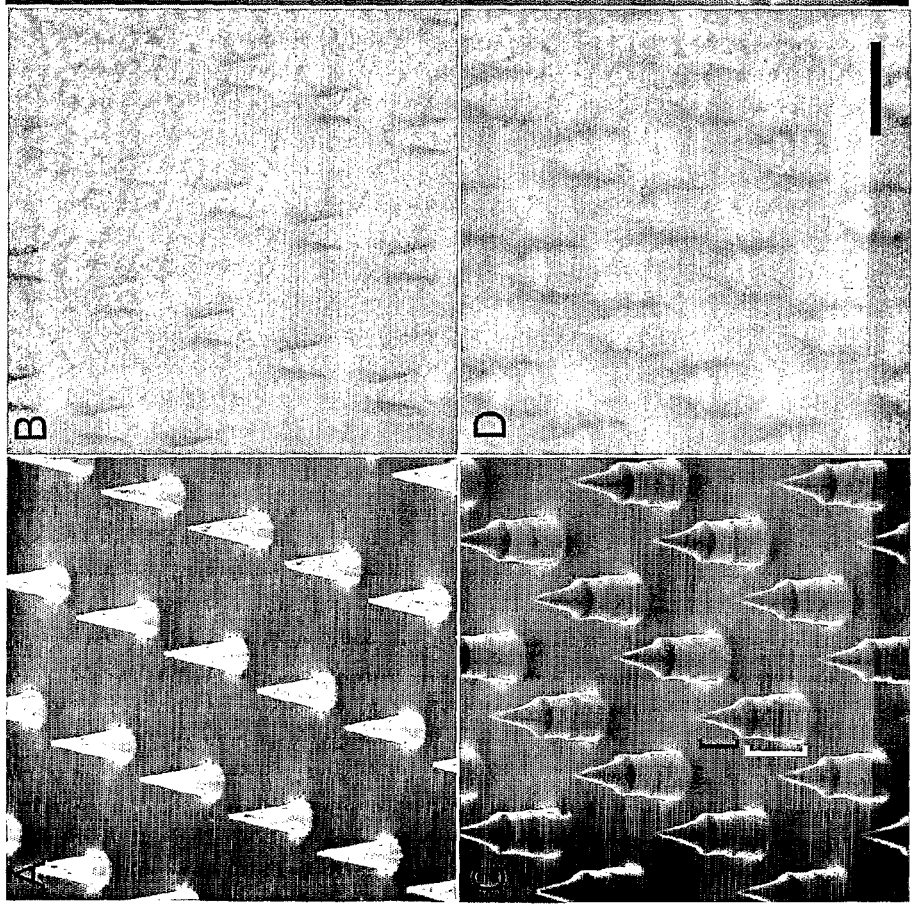

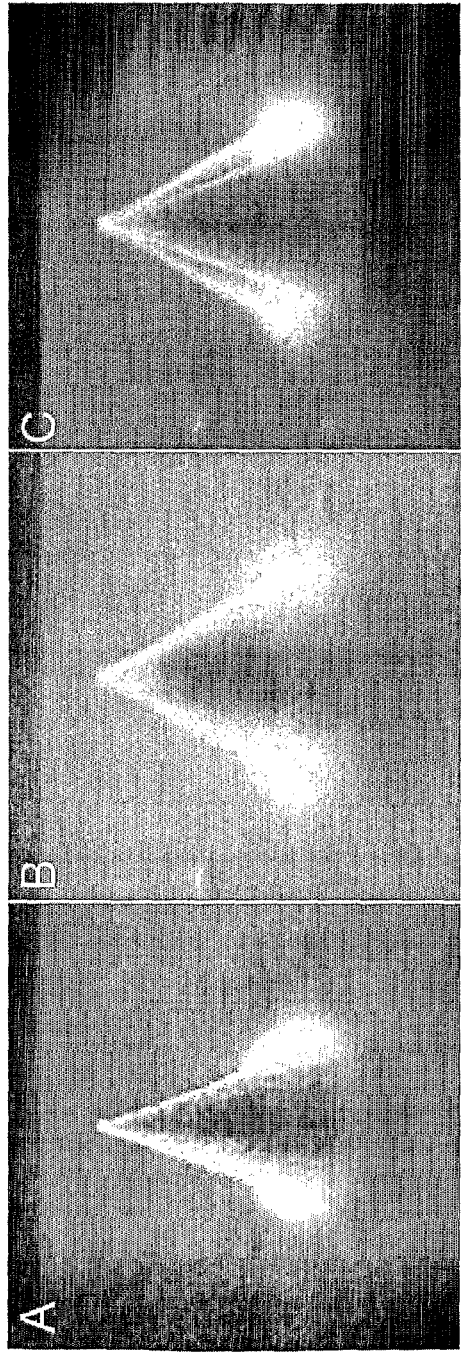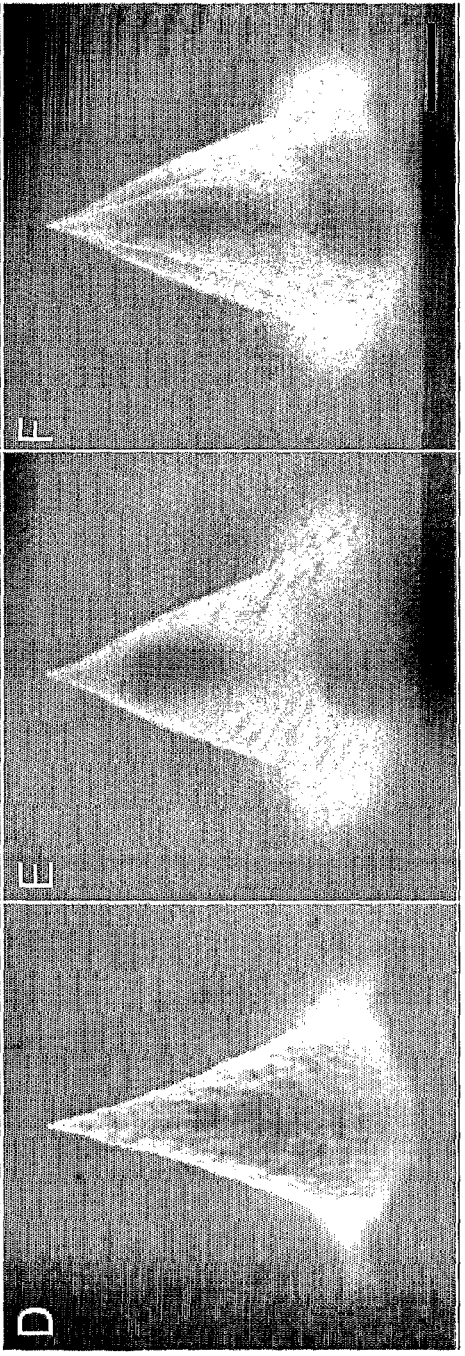

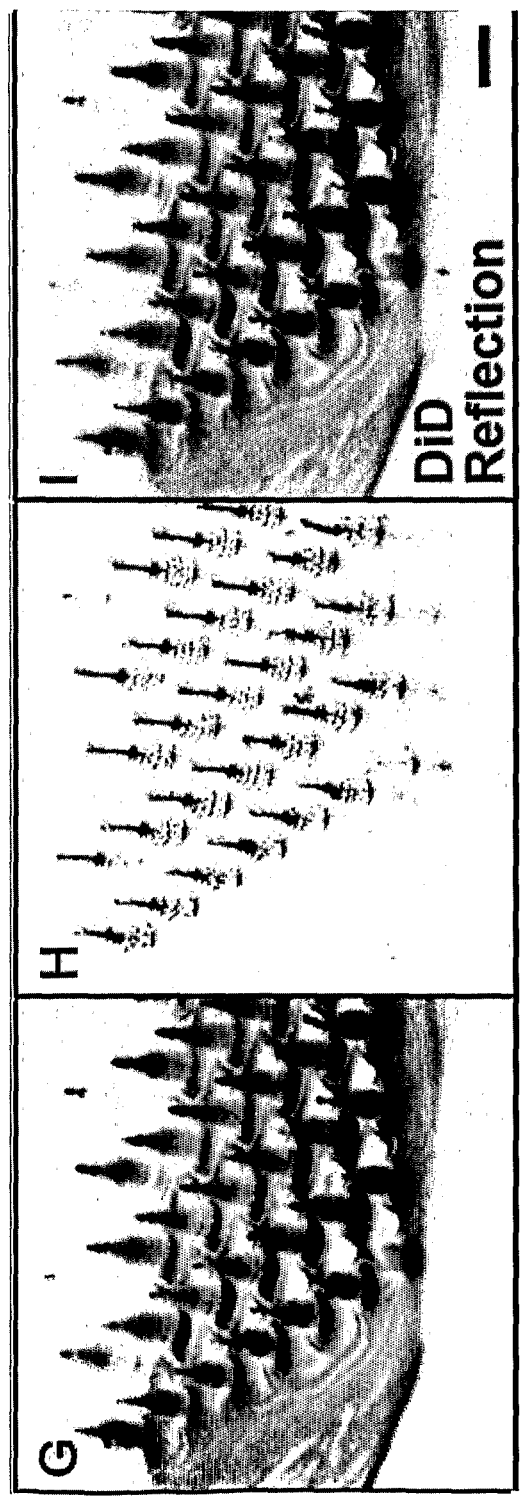

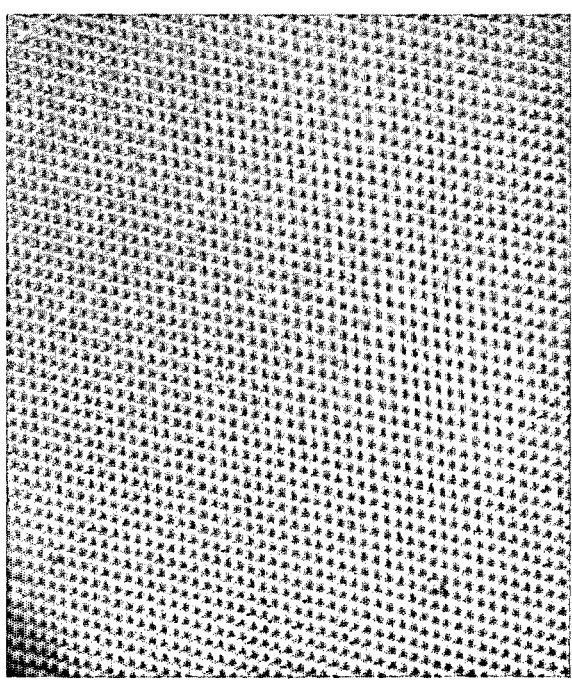
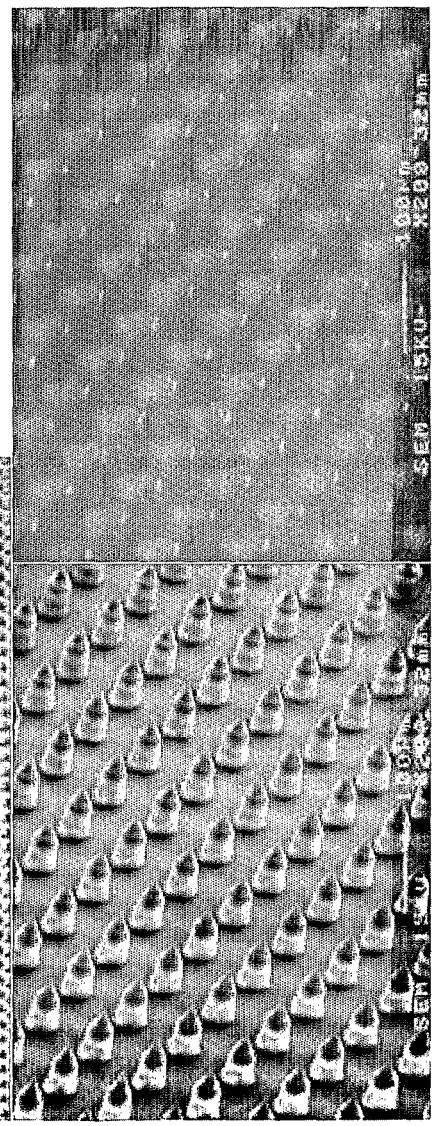
Fig. 12A
Fig. 12B
Fig. 12C

Fig. 17A
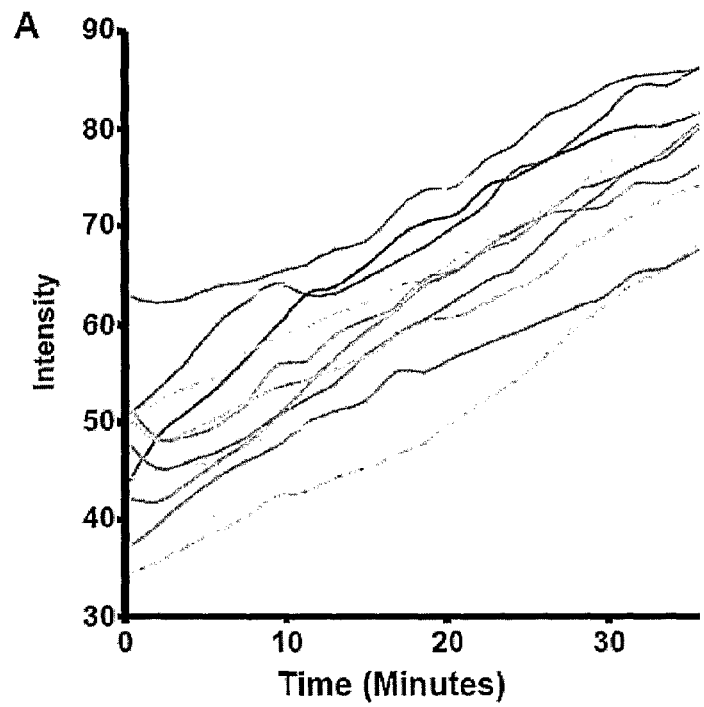
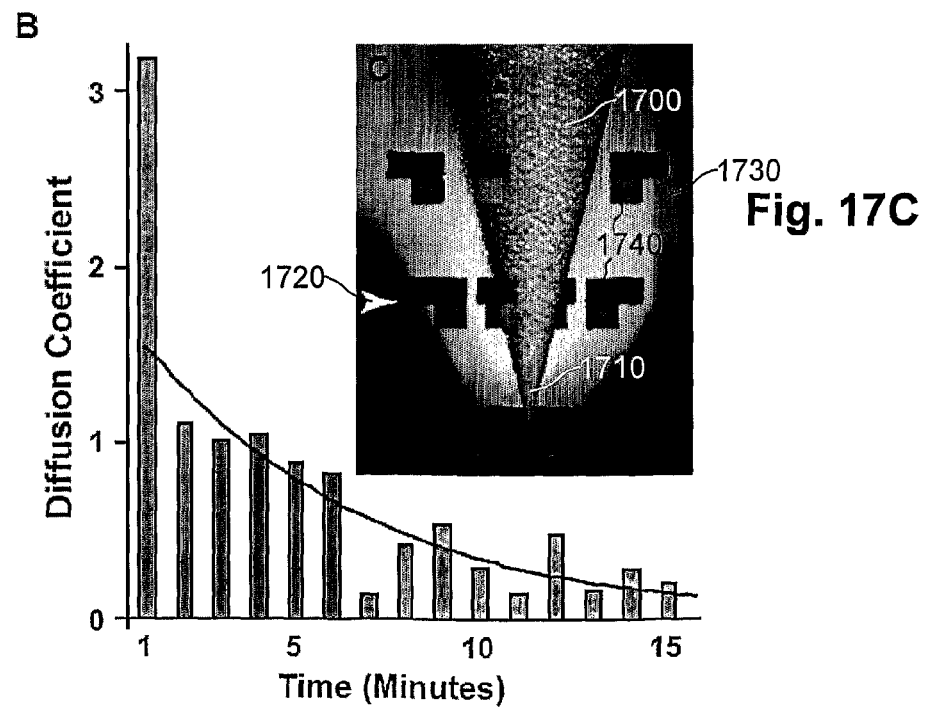
Fig. 17C
Fig. 17B

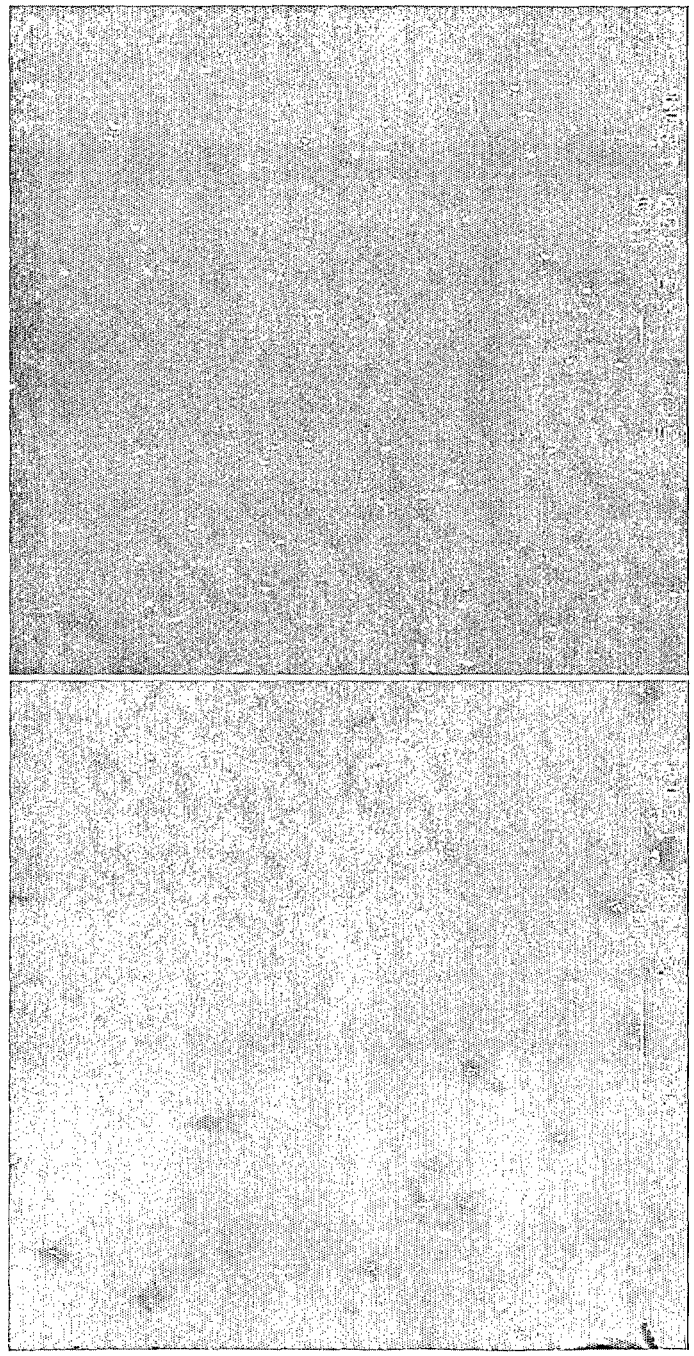

COATING METHOD

PRIORITY CLAIM TO RELATED APPLICATIONS

This application is a national stage application under 35 U.S.C. §371 of PCT/AU2008/001903, filed Dec. 23, 2008, and published as WO 2009/079712 A1 on Jul. 2, 2009, which claims priority to Australian Patent Application No. 2007907092 Filed Dec. 24, 2007, which applications and publications are incorporated herein by reference and made a part hereof in their entirety, and the benefit of priority of which is claimed herein.

BACKGROUND OF THE INVENTION

The present invention relates to a method of coating and in particular to coating projections provided on a patch.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

It is known to provide patches including a number of projections thereon to allow bioactive material to be administered to a subject. Such arrays of projections or needles on a patch are an increasingly effective way of delivering therapeutic agents or biomarkers since there is minimal or no pain, little or no injury from the needle and highly reduced possibility of cross infection. The solid projections or needles on a patch can be coated with drugs or macromolecules. These can be subsequently delivered to a desired target by the penetration of the projections or needles into the skin.

For example, WO2005/072630 describes devices for delivering bioactive materials and other stimuli to living cells, methods of manufacture of the device and various uses of the device, including a number of medical applications. The device comprises a plurality of projections which can penetrate a body surface so as to deliver the bioactive material or stimulus to the required site. The projections are typically solid and the delivery end section of the projection is so dimensioned as to be capable of insertion into targeted cells or specific sites to deliver the bioactive material or stimulus without appreciable damage to the targeted cells or specific sites therein.

Various methods of coating patches are also known. For example, microprojection arrays are known to be coated by being dipped into a coating solution reservoir through dip-holes at the same spacing as the microneedles in the array (Harvinder S. Gill and Mark R. Prausnitz, Journal of Controlled Release, 117 (2007) 227-237 and Harvinder S. Gill and Mark R Prausnitz, Pharmaceutical Research, 24 (2007) 1369-1380). The coating solution contains carboxymethylcellulose (CMC) sodium salt, poloxamer 188 and a suitable drug. The size of the projection is around 700 µm in length, 160 µm in width and 50 µm in thickness. The distance between projections is over a few mm.

Microneedle arrays can also be coated with a drug by partial immersion in aqueous formulations containing drug and polysorbate 20 (Michel Cormier, Bonny Johnson, Mahmoud Ameri, Kofi Nyam, Luz Libiran, Dee Dee Zhang, Pete Daddona, Journal of Controlled Release 97 (2004) 503-511). Each microneedle is arrowhead-shaped with a length of 200 µm, a maximal width of 170 µm, and a thickness of 35 µm. The density of projections is 321 projections/cm$^2$.

Microprojection arrays are also known to be coated by immersion in an aqueous solution of ovabulmin or OVA (James A. Matriano, Michel Cormier, Juanita Johnson, Wendy A. Young, Margaret Buttery, Kofi Nyam, and Peter E. Daddona, Pharmaceutical Research, 19 (2002) 63-70). The arrays were air-dried for 1 h at ambient conditions. The length of each microprojection is 330 µm. The density of projections is 190 projections/cm$^2$.

WO02/074173 and U.S. Pat. No. 6,855,372 describe an apparatus and method for selectively applying an agent-containing liquid coating to skin piercing microprojections (10). The coating solution is applied to the skin piercing microprojections (10) using a coating technique which selectively coats only the skin piercing microprojections (10) and not the substrate (12) from which the microprojections (10) extend, and then dried. The coating method includes providing an agent-containing coating liquid and conveying the liquid to a liquid holding surface having a coating transfer region. The depth of the coating liquid at the coating transfer region is precisely controlled. The microprojections are then immersed to a predetermined level in the coating liquid. The liquid that coats the microprojections (10) is then dried to form a solid agent-containing coating on the microprojections (10).

US2005/197308 relates to a pharmaceutical agent delivery device having a skin piercing protrusion that is typically about 100 to 400 µm in length. The protrusion can be coated with a solid biodegradable reservoir medium containing the pharmaceutical agent.

However, the coating quality of these techniques can be poor as a large area around the edges and the tips of the projections remain poorly coated.

Furthermore, previous systems have focussed on coating large and very sparsely packed projections. Such techniques often prove to be unsuccessful when coating small and densely packed projections, which are often hydrophobic, reducing the effectiveness of traditional coating techniques. Hydrophobic properties occur when such type of microstructures are patterned on a hydrophobic substrate. Consequently, coating using straightforward immersion often results in projections being uncoated.

Attempts to overcome poor coating by attaching thiols to microprojection patches, with DNA and positively charged polymers then being deposited in alternate layers, have been tried. The DNA amount deposited on patches increased exponentially with the increase of number of DNA layers on patches. However, in-vitro release experiments showed that the release in phosphate-buffered saline (PBS) solution was extremely slow. For example, 12 layers of DNA on both projections and base of each patch can only release 2.25 µg DNA after overnight dipping in 1.5 M NaCl solution (physiological salt concentration is only 0.15 M or 0.9%). Whilst no release of DNA can be detected after overnight dipping of coated patches in 0.15 M NaCl solution.

For successful vaccine delivery systems, effective dry coating of the vaccine on the patch projections in a controlled manner, followed by the rapid, subsequent release of an effective amount of the vaccine in the skin after application of the patch, is required. Further, whilst it is desirable to employ patches that have smaller projections or needles, effectively coating these using existing techniques is difficult.

SUMMARY OF THE PRESENT INVENTION

The present invention seeks to substantially overcome, or at least ameliorate, one or more disadvantages of existing arrangements.

In a first broad form the present invention seeks to provide a method of coating a material onto projections provided on a patch, wherein the method includes:
- a) applying a coating solution containing the material to at least the projections; and,
- b) drying the coating solution using a gas flow.

Typically the method includes at least one of:
- a) distributing the coating solution over the projections at least in part using the gas flow; and,
- b) moving coating solution on patches to wet all projections using a gas flow, thereby coating at least part of the projections.

Typically the method includes selecting coating properties to thereby control the distribution of coating over the projections.

Typically coating properties are selected so that at least one of:
- a) at least tips of the projections are coated; and,
- b) at least target sections of the projections are coated.

Typically the projections are provided on a surface of the patch, and wherein the method includes selecting coating properties to thereby vary at least one of:
- a) an amount of coating on a surface of the patch; and,
- b) an amount of coating on the projections.

Typically the coating properties include at least one of:
- a) a gas flow rate;
- b) patch properties;
- c) coating solution properties; and,
- d) a drying time.

Typically the patch properties include at least one of:
- a) projection size;
- b) projection shape;
- c) projection spacing; and,
- d) projection materials.

Typically the coating solution properties include at least one of:
- a) a surface tension; and,
- b) a viscosity.

Typically the material includes at least one of:
- a) nanoparticles;
- b) a nucleic acid or protein;
- c) an antigen, allergen, or adjuvant;
- d) parasites, bacteria, viruses, or virus-like particles;
- e) quantum dots, SERS tags, Raman tags or other nanobiosensors;
- f) metals or metallic compounds; and,
- g) molecules, elements or compounds.

Typically the coating solution includes a therapeutic agent.

Typically the therapeutic agent is at least one of:
- a) DNA having a concentration of between 0.01 mg/ml and 5 mg/ml; and,
- b) protein having a concentration of between 0.01 mg/ml and 50 mg/ml Typically the coating solution includes at least one of:
- a) a viscosity enhancer;
- b) a surfactant; and,
- c) an adjuvant.

Typically the adjuvant acts as a surfactant.

Typically at least one of:
- a) the viscosity agent is 0% to 90% of the coating solution; and,
- b) the surfactant is 0% to 90% of the coating solution.

Typically the viscosity agent is at least one of MC, CMC, gelatin, agar, and agarose.

Typically the coating solution has a viscosity of between $10^{-3}$ Pa·S and 1 Pa·S.

Typically the coating solution has a viscosity of 0.01-0.06 Pa·S

Typically the coating solution has a surface tension of between 0.023 N/m and 0.073 N/m.

Typically the coating solution has a surface tension of 0.03-0.04 N/m.

Typically the gas flow has a gas flow rate of between 6 m/s and 10 m/s.

Typically the method includes selecting a gas flow rate in accordance with gas properties.

Typically the gas properties include a gas density.

Typically the gas flow includes at least one of:

a) nitrogen;
b) argon;
c) air flow; and,
d) an inert gas.

Typically the gas flow is induced at least in part by extracting gas from a container containing the patch.

Typically the method includes coating the projections a number of times.

Typically the method includes:

a) coating the surface a first time using a first set of coating parameters; and,
b) coating the surface at least a second time using a second set of coating parameters different to the first set of coating parameters.

Typically the method includes applying between 5 and 15 μl of coating solution to the patch.

Typically the patch has a surface area of approximately 0.16 $cm^2$.

Typically the projections have a density of between 1,000-30,000 projections/$cm^2$.

Typically the projections have a density of 20,000 projections/$cm^2$

Typically the projections have a length of between 10 to 400 μm.

Typically the projections have a length of 90 μm

Typically the projections have a radius of curvature of greater than 1 μm.

Typically the projections have a radius of curvature greater than 5 μm.

Typically the projections include a support section and a targeting section.

Typically the targeting section has a diameter of less than at least one of:

a) 50 μm; and,
b) 100 μm;
c) 150 μm; and,
d) 400 μm.

Typically a length for the targeting section is at least:

a) less than 50 μm; and,
b) less than 100 μm; and,
c) less than 300 μm.

Typically a length for the support section is at least one of:

a) for epidermal delivery <200 μm;
b) for dermal cell delivery <1000 μm;
c) for delivery to basal cells in the epithelium of the mucosa 600-800 μm; and,
d) for lung delivery of the order of 100 μm.

Typically a length for the support section is at least one of:

a) for epidermal delivery greater than the thickness of the Stratum Corneum;
b) for dermal cell delivery greater than the thickness of epidermis;
c) for delivery to basal cells in the epithelium of the mucosa greater than a thickness of upper epithelium; and,
d) for lung delivery of the order of 100 μm in this case.

Typically the projections are solid.

Typically the projections are non-porous and non-hollow.

Typically the patch is at least one of:
a) hydrophobic; and,
b) hydrophilic.

In a second broad form the present invention seeks to provide a method of coating a material onto projections provided on a patch, wherein the method includes:
a) applying a coating solution containing the material to at least the projections; and,
b) distributing the coating solution, over the projections at least in part using a gas flow.

Typically the method further includes drying the coating solution using the gas flow.

In a third broad form the present invention seeks to provide a coating solution for coating a material onto projections on a patch, the coating solution including Quillaja saponins acting as a surfactant and a vaccine adjuvant.

Typically the Quillaja saponins include at least one of QA, QS-21, QS-7 and other purified saponin adjuvants.

Typically the coating solution includes an adjuvant that is an Immunostimulating complex.

Typically the Immunostimulating complex includes ISCO-MATRIX.

Typically the coating solution includes at least one of:
a) a viscosity enhancer;
b) a surfactant; and,
c) an adjuvant.

In a fourth broad form the present invention seeks to provide a coating solution for coating a material onto projections on a patch, the coating solution including nanoparticles.

Typically the nanoparticles are multilayered nanoparticles.

Typically the nanoparticles includes layers including at least one of:
a) cell targeting molecules; and,
b) cell-entry facilitating molecules.

Typically the nanoparticles include layers including intracellular targeting molecules.

In a fifth broad form the present invention seeks to provide a patch for use in medical procedures, the patch including a number of projections thereon, the projections having a coating applied thereto using the method of the first broad form of the invention.

In a sixth broad form the present invention seeks to provide a method performing a medical procedure, the method including applying a patch to a subject, the patch being a patch according to the fifth broad form of the invention.

Typically the method includes hydrating a surface of the subject and applying the patch to the hydrated surface.

It will be appreciated that the broad forms of the invention may be used individually or in combination.

BRIEF DESCRIPTION OF THE DRAWINGS

An example of the present invention will now be described with reference to the accompanying drawings, in which:—

FIG. 1C is a schematic diagram of an example of the device of FIG. 1A in use;

FIGS. 1D to 1F are schematic diagrams of examples of projections used in the device of FIG. 1A;

FIGS. 2A and 2B are schematic plan views of examples of a fluid spreading out and of a droplet forming on a hydrophobic patch, respectively;

FIGS. 2C and 2D are schematic side views of the examples of FIGS. 2A and 2B in a Wenzel state;

FIGS. 2E and 2F are schematic side views of the examples of FIGS. 2A and 2B in a Cassie state;

FIGS. 9A and 9C show examples of secondary electron images of patches with 60 μm and 90 μm long projections, respectively;

FIGS. 9B and 9D show examples of corresponding backscattered electron images for the patches of FIGS. 9A and 9C, respectively;

FIGS. 9E and 9F show examples of scanning electron microscopy (SEM) images of 60 μm long projections dip coated and dried in air;

FIGS. 11A, 11B and 11C show examples of individual 35 μm long projections before coating, after coating using a gas flow and an overlay of the images, respectively;

FIGS. 11D, 11E and 11F show examples of individual 60 μm long projections before coating, after coating using a gas flow and an overlay of the images, respectively;

FIGS. 11G, 11H and 11I show examples of fluorescence images of individual 90 μm long projections from a DiD coating, the reflection and an overlay of the images, respectively;

FIG. 12A shows an example of an SEM image of a patch coated using a gas flow;

FIGS. 12B and 12C show example of secondary and backscattered electron high-magnification images of projections coated using a gas flow;

FIG. 17A is a graph of an example of release intensity values from a 70 kDa payload in living skin;

FIG. 17B is a graph of an example of release diffusion coefficients kinetics from a 70 kDa payload in living skin;

FIG. 17C is a schematic diagram illustrating an interrogation space for the measurements of FIGS. 17A and 17B;

DETAILED DESCRIPTION OF THE PREFERRED EMBODIMENTS

Figure 1A:
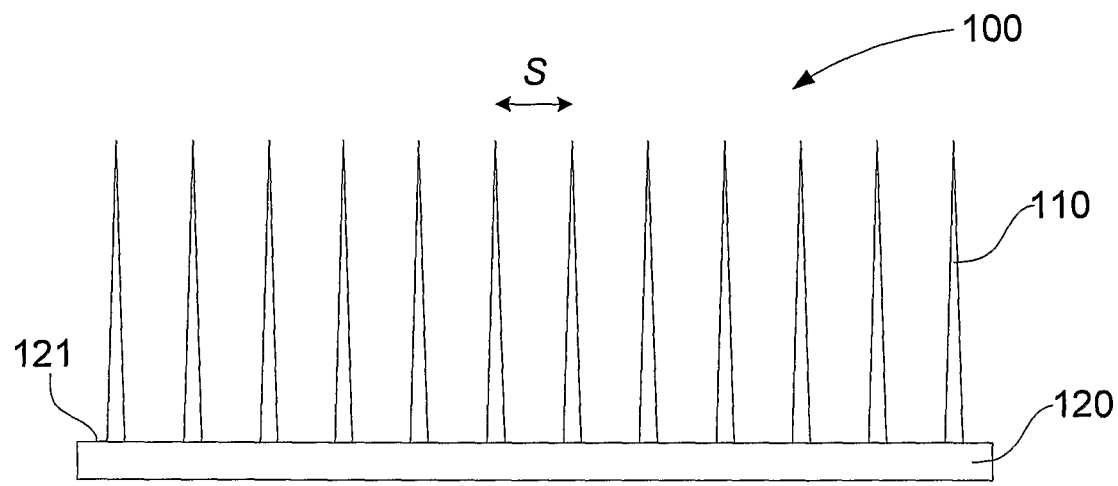
FIGS. 1A and 1B are schematic side and plan views, respectively, of an example of device for delivery of material to targets within a body.
Figure 1B:
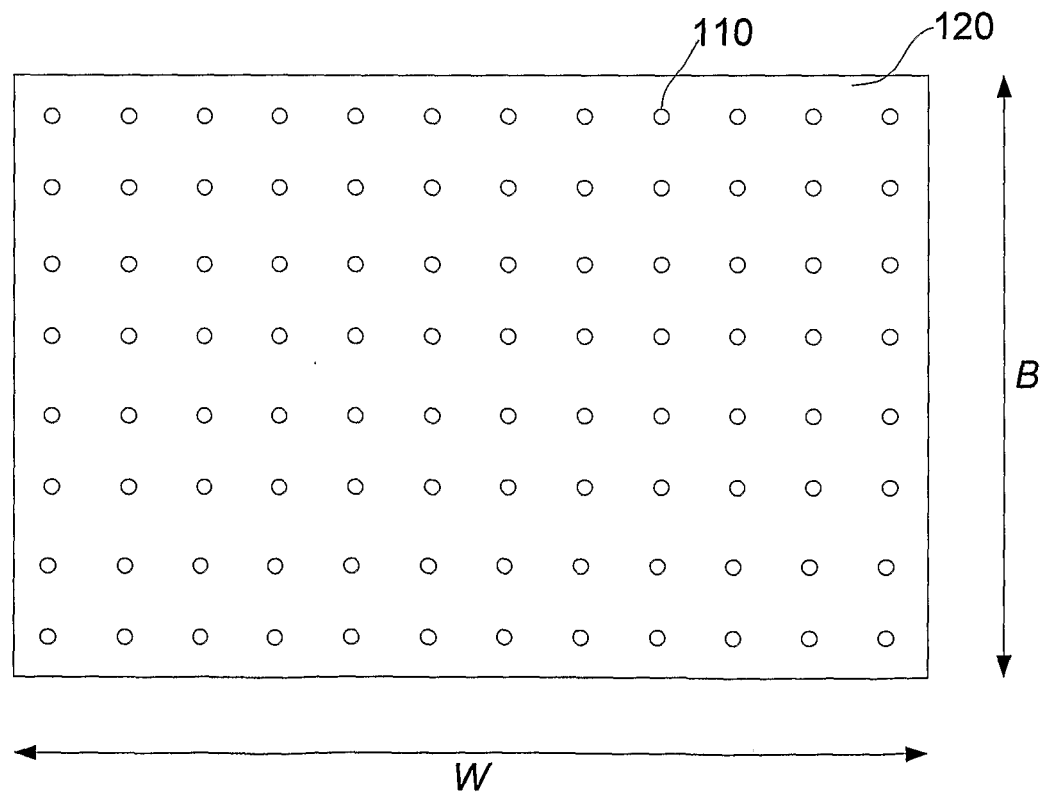

An example of a device for delivering material to targets within a body will now be described with reference to FIGS. 1A to 1F.

In this example, the device is in the form of patch 100 having a number of projections 110 provided on a surface 121 of a substrate 120. The projections 110 and substrate 120 may be formed from any suitable material, but in one example, are formed from a silicon type material, allowing the device to be fabricated using processes such as vapour deposition, silicon etching, Deep Reactive Ion Etching (DRIE), or the like. The projections are therefore typically solid, non-porous and non-hollow, although this is not essential.

In the example shown, the patch has a width W and a breadth B with the projections 110 being separated by spacing S.

In use, the patch 100 is positioned against a surface of a subject, allowing the projections to enter the surface and provide material to one or more targets therein. An example of this is shown in FIG. 1C.

In this example, the patch 100 is urged against a subject's skin shown generally at 150, so that the projections 110 pierce the Stratum Corneum 160, and enter the Viable Epidermis 170 to reach targets of interest, shown generally at 180. However, this is not essential and the patch can be used to deliver material to any part or region in the subject.

It will be appreciated that the projections can have a variety of shapes, and examples of suitable projection shapes are shown in more detail in FIGS. 1D, 1E and 1F.

In one example, the projection includes a targeting section 111, intended to deliver the material or stimulus to targets within the body, and a support section 112 for supporting the targeting section 111. However, this is not essential, and a single element may be used.

In the example of FIG. 1D, the projection is formed from a conically shaped member, which tapers gradually along its entire length. In this example, the targeting section 111 is therefore defined to be the part of the projection having a diameter of less than $d_2$.

In FIGS. 1E and 1F, the structure of the projection may vary along its length to provide a defined targeting section 111 with a designed structure. In the example of FIG. 1E, the targeting section 111 is in the form of a substantially cylindrical shape, such that the diameter $d_1$ is approximately equal to the diameter $d_2$, with a tapered support section, such that the diameter $d_2$ is smaller than the diameter $d_3$. In contrast, in the example of FIG. 1F, the targeting section 111 is in the form of taper such that the diameter $d_1$ is smaller than the diameter $d_2$, with a cylindrical support section, such that the diameter $d_2$ is substantially equal to the diameter $d_3$.

In general, the support section 112 has a length a, whilst the targeting section 111 has a length l. The diameter of the tip is indicated by $d_1$, whilst the diameter of the support section base is given by $d_3$.

In use, the device can be used to deliver material to specific targets within the body or more generally to the blood supply, or tissue within the body and the configuration of the device will tend to depend on its intended use.

Thus, for example, if the patch is configured so as to ensure material is delivered to specific targets such as cells, then it may be necessary to select a more specific arrangement of projections than if delivery is provided mom generally to the blood. To achieve this, the device can be provided with a particular configuration of patch parameters to ensure specific targeting. The patch parameters can include the number of projections N, the spacing S between projections, and the projection size and shape. This is described in more detail in co-pending application U.S. Ser. No. 11/496,053.

In one specific example, a patch having a surface area of approximately 0.16 cm² has projections provided at a density of between 1,000-30,000 projections/cm², and typically at a density of approximately 20,000 projections/cm². However, alternative dimensions can be used. For example, a patch for an animal such as a mouse may have a surface area of 0.32 to 0.48 cm², whereas as a patch for a human may have a surface area of approximately 1 cm². A variety of surface areas can be achieved by mounting a suitable number and arrangement of patches on a common substrate.

The projections typically have a length of between 10 to 200 μm and typically 90 μm with a radius of curvature of greater than 1 μm and more typically greater than 5 μm. However, it will be appreciated that other dimensions may be used.

If distinct targeting section and support sections are provided, the targeting section typically has a diameter of less than 1 μm and more typically less than 0.5 μm. The length of the targeting section is typically less than 100 μm, less than 10 μm and typically less than 5 μm. The length of the support section typically varies depending on the location of the target within the subject. Example lengths include less than 200 μm for epidermal delivery, less than 1000 μm for dermal cell delivery, 600-800 μm for delivery to basal cells in the epithelium of the mucosa and approximately 100 μm for lung delivery.

In order to allow delivery of material to the subject, it is necessary to provide a coating on at least the projections. In one example, coating is achieved by applying a solution containing the material to at least the projections. This may be achieved in any one of a number of manners. Thus, for example, the solution can be applied by dripping the solution onto the patch. Alternatively however other techniques may be used, such as immersion of the patch in solution.

In one example, the gas flow can be used to help ensure even distribution of material over the entire patch. This is particularly useful when the combination of patch and coating solution properties prevent the coating solution from wetting the projections. When coating solution is applied to a surface it can either spread out, or remain as a droplet, and can also fill the space between the projections (known as a "Wenzel" state), or rest on the top of the projections (known as a "Cassie" state). Examples of this will now be described will respect to FIGS. 2A to 2F.

In the example of FIG. 2A the coating solution has properties, such as surface tension and viscosity that allow the coating solution 200 to spread out over the patch 100. In the example of FIG. 2B the properties are such that prevents the solution 200 spreading out over the patch and projections. In this example, when solution is applied to the patch, the solution forms a droplet 210.

Examples of these scenarios in the Wenzel and Cassie states are shown in FIGS. 2C to 2F.

As shown in FIG. 2C, the coating solution has spread out in the Wenzel state, so that the coating solution 200 flows over the surface 121 of the patch 100 between the projections 110. As a result, it is possible to completely immerse the projections 110 by simply adding more solution until the solution level 201 rises above the level of the projections 110.

In the example of FIG. 2D, the coating has remained confined in the Wenzel state. Despite being in the Wenzel state, not all of the projections 110 are completely wetted.

In the example of FIG. 2E, even though the coating solution has spread out, but by virtue of being in the Cassie state, not all of the projections 110 are completely wetted as the droplet rests on top of the projections 110. Similarly, in the example of FIG. 2F, as the coating solution is in the Cassie state, again not all of the projections 110 are completely wetted as the droplet rests on top of the projections 110.

Accordingly, in some instances, the projections 110 can remain un-immersed, meaning they will not be coated when the solution dries. However, using the gas flow, this can urge the coating solution around the surface of the patch, thereby ensuring that the projections are completely wetted.

Thus, in some of the example patch configurations described above, the patch is hydrophobic so that the contact angle of coating solution on patches is greater than 90 degrees, meaning the coating solution can not spread on patches.

In this case, gas flow allows a small volume of coating solution to be distributed over the patch to thereby thoroughly wet all projections. This avoids the need to immerse the entire patch surface in coating solution as well as allowing a small volume of coating solution to be distributed over the patch to thoroughly wet all projections, thereby reducing the amount of coating solution required to coat a patch.

In one example, when coat 0.16 $cm^2$ patches with 60 μm needles, over 20 μl coating solution is needed to cover all projections. However, the using of gas flow can control the movement of 6 μl coating solution to wet all projections and achieve uniform coating.

Even in the event that coating solution initially wets the projections, previous drying techniques often leave the projections uncoated. The reason for this is that the coating solution covers many projections due to capillary action, and slowly disperses from the projections during drying under ambient conditions. During the slow drying process, the coating solution drips off from the projections to the base of patches, meaning the projections will not be coated once the coating solution dries. This is undesirable as it reduces the ability of the patch to deliver material to a subject. In particular, maximising coating on the projections increases the rate of transfer of material to the subject, as well as maximising the amount of material on the patch that is delivered.

Accordingly, in one example, the coating solution is dried using a gas flow, to thereby remove the coating solution between projections, reduce the drying time and consequently reduce the chance of coating solution dispersing from the projections, and thereby ensure that the projections remain coated as the coating solution dries.

The gas flow could also be provided in a variety of manners. For example, this could be achieved by using a gas jet directed towards the patch. Whilst any gas may be used, in one example the gas is nitrogen as this is substantially inert and will not therefore react with the solution, whilst also being readily available. It will be appreciated that other inert gases, such as argon, can also be used, as well as air flow or other types of gas flow. In one example, the gas selected will depend on the reactivity of the coating material. As an alternative to the use of a gas jet however, flow could be induced by extracting gas from a container containing the patch.

When performing the coating process it is typical to select coating properties, such as gas flow rate, solution properties such as the solution viscosity and surface tension, and optionally a drying time, to thereby control the distribution of coating over the projections 110.

For example, the degree to which the projections are wetted will also depend on the coating solution properties. Thus, for example, if a higher viscosity solution is used, this will tend to adhere more strongly to the projections, and hence allow a greater thickness of coating to be achieved. However, a higher viscosity coating solution may require an increased gas flow to allow adequate distribution over the patch.

In the case of surface tension, if the surface tension is too great, the coating solution will not be effective at wetting the projections, reducing the effectiveness of coating. A lower surface tension will increase the ability of the coating solution to wet the projections, allowing better coating, although too low a surface tension and the coating solution can rest primarily on the surface of patches reducing coating of the projection tips.

In addition to this, the solution properties will also have an impact on the drying process. For example, if a thicker viscosity coating solution is used this reduces the likelihood of coating run-off during the drying process, but may increase the drying time.

Additional control is also achieved using the gas flow rate. Thus, a higher gas flow rate can increase the degree to which coating solution is distributed on the patch, and/or can reduce the drying time.

Appropriate selection of the coating properties can be used to ensure at least the projections are coated, as well as to allow the thickness of coating on the projections to be controlled. This can also be used to vary properties such as the relative amounts of coating on the patch surface 121 and on the projections 110, which can be characterised by a coating ratio based on a ratio of an amount of coating on the projections 110 against an amount of coating on the patch surface 121.

It will also be appreciated that the degree to which the patch is hydrophobic will depend on the patch configuration and in particular, on patch parameters such as the projection size and shape and the projection spacing S. Accordingly, when performing a coating process, it is typical to first determine patch properties and then use this information to allow appropriate coating properties to be selected.

In general the coating solution includes at least a material such as a therapeutic agent and examples of suitable materials include:
nanoparticles;
a nucleic acid or protein;
an antigen, allergen, or adjuvant;
parasites, bacteria, viruses, or virus-like particles;
quantum dots, SERS tags, Raman tags or other nanobiosensors;
metals or metallic compounds; and,
molecules, elements or compounds.

Examples of preferred formulations include a solution containing DNA having a concentration of between 0.01 mg/ml and 5 mg/ml or protein having a concentration of between 0.01 and 50 mg/ml.

The agent or other material is typically either dissolved in a suitable solvent or held in suspension in a suitable carrier fluid, as will be appreciated by those skilled in the art. In one example, the solvent is acetone, although alternatively water or other suitable solvents can be used. The resulting surface tension in pure acetone solution and pure aqueous solution is between 0.023 N/m (acetone) and 0.073 N/m (water).

The solution properties are also typically controlled through the addition of one or more other agents such as a viscosity enhancer, a surfactant, and an adjuvant. It will be appreciated that other additives such as detergents may also be used. These ingredients can be provided in a range of different concentrations. For example, the viscosity enhancer or surfactant can form between 0% and 90% of the coating solution.

A range of different viscosity enhancers can be used and examples include MC, CMC, gelatin, agar, and agarose and any other viscosity agents. The solution typically has a viscosity of between $10^{-3}$ Pa·S and 1 Pa·S. In one example, using a coating solution containing 1-2% MC, which results in suitable uniform coatings, resulting in a viscosity within the range 0.011 (1%)-0.055 (2%) Pa·S.

Similarly, a range of different surfactants can be used to modify the surface tension of the coating solution, such as any surfactant or any suitable agent that changes surface tension, and that is biocompatible at a low concentration.

Surfactants are wetting agents that lower the surface tension of a liquid, allowing easier spreading, and lower the interfacial tension between two liquids. The term 'surfactant' is a blend of "surface acting agent". Surfactants are usually organic compounds that are amphiphilic, meaning they contain both hydrophobic groups ("tails") and hydrophilic groups ("heads"). Therefore, they are soluble in both organic solvents and water.

Surfactants may be used as the surface tension of the coating solution becomes dominant on a micron-scale, so the surfactant reduces the surface tension of the solution, which helps solution, wet the surface of patch projections, thereby improving coating quality. Furthermore, a viscosity enhancer can increase the viscosity of coating solution and therefore increase the thickness of coating.

Example coating solutions will be described in more detail below.

Once the coating solution has been formed, the patch can be coated either by dripping the coating solution onto the patch or by immersing the patch in the coating solution. Typically, the amount of coating solution used to coat a patch is between 5 μl to 15 μl, for patches similar to those outlined above.

Once the coating solution is deposited on the patch, the patch may be allowed to rest, for example in a sealed environment, to assist with wetting of projections, although this is not essential and may depend on the nature of the deposition process. Following this, or otherwise, a gas jet is used to evenly disperse the coating solution over the patch surface, and/or to dry the coating solution.

In general, the gas jet should be of sufficient diameter to completely encompass the patch. Accordingly, in one example, the diameter should be about 1.5 times and even 2 times as big as the largest patch dimension.

Typically a flow rate of between 6-10 m/s is used to distribute and/or dry the coating solution, however, this will depend on the solution properties. However a gas jet of a higher flow rate can also be used to remove excess coating solution, and the gas flow rate used may depend on gas properties, such the density of the gas.

Figure 3:
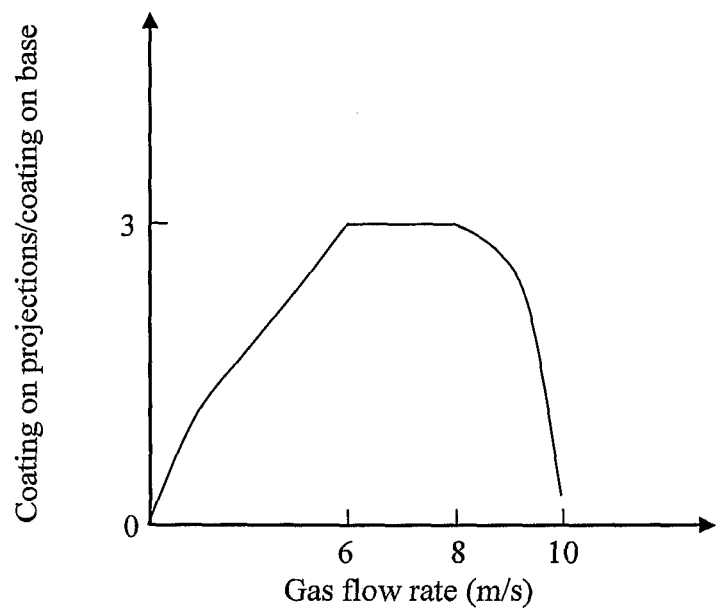
FIG. 3 is a graph of an example of a relationship between a coating ratio and a gas flow rate.

An example of the coating ratio against gas flow rate is shown in FIG. 3, for a coating solution having a viscosity of between 0-0.05 Pa·S and a surface tension of 0.023-0.073 N/m. For this coating solution, a suitable range of gas flow rate is about 6-8 m/s. A faster flow rate, around 10 m/s gas flow, can be used to remove excess coating solution, whilst a reduced gas flow rate has a reduced effect on the coating. Whilst different flow rates may be required for coating solutions having different coating properties, in general, a flow rate of 6-8 m/s is acceptable for most coating solutions. If a coating solution is applied on 60 μm projection patches and dried in ambient air, the coating will tend to remain exclusively on the patch surface 121. However, if 10 μl of coating solution containing 2% MC, 2% OVA protein and 0.2% QA is applied on 90 μm projection patches and dry with a nitrogen jet, 120 μg OVA protein will be coated onto projections and 40 μg OVA protein will be coated onto base, using a gas flow in the range 6-8 m/s.

Accordingly, the above described examples provide method for coating therapeutic agents including vaccines on to projections on a patch, to thereby allow for their rapid release when the patch is applied to a subject. The method provides substantially uniform and controllable coating of therapeutic agents like DNA or protein vaccine onto the patches, even in circumstances when the patches are hydrophobic. The method can be applied to any form of patch but is especially suited for patches having projections that are shorter than 200 μm and separated by 10-1000 μm.

Further variations and options will now be described.

Figure 4:
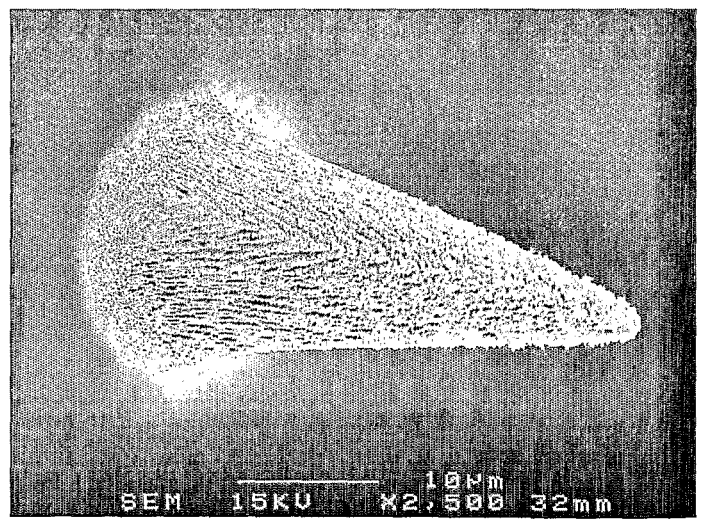
FIG. 4 is an example of a secondary electron image of a patch having a gold coating.

For example, the patch and/or projections can be coated with a thin layer of a suitable metal, prior to application of the coating solution. The reason for this is that metals tend to have, relative to the native silicon or other patch material, a high surface energy, which in turn helps assist with the coating process. In one example, the metal layer is gold, although other suitable metals may be used. An example of a gold coating on a silicon projection is shown in FIG. 4. Gold coating forms a nanostructure on silicon projection. The thickness is about 400-1500 nm and the size of gold particles is about 200-400 nm. This structure together with the projection arrangement provides a very hydrophobic surface.

As described above, the coating solution is typically selected to have a suitable viscosity and surface tension. This may be achieved using viscosity enhancers and surfactants to control the coating solution properties. However, use of surfactants is not essential and in one example, a vaccine coating can be achieved using MC without requiring surfactants. However, if CMC is used for coating, the addition of surfactants is preferred.

As mentioned above, the surfactant can be any suitable agent such as poloxomer 188, triton-X 100, NP40, QA or any surfactant that is biocompatible at a low concentration. The concentration of the surfactant is from about wt. 0% to about 90% of the coating solution, depending on the required solution properties.

A vaccine adjuvant may also be added to the coating solution for enhancing immune response to vaccines. In one example, the adjuvants used include Quillaja saponins, such as QA, QS-21, QS-7 or other purified saponin adjuvants. Use of QA and other similar saponin adjuvants can be particularly beneficial as QA not only acts as a surfactant for coating purposes but also as the vaccine adjuvant. Furthermore, due to QA effectiveness in reducing the surface tension of the coating solution, this can in turn help in reducing the amount of excipients used for coating.

Other amphipathic immunostimulatory compounds such as dimethyldioctadecylammonium bromide or chemically modified immunostimulatory molecules to give surfactant properties can also be employed.

The viscosity agent can be selected from MC, CMC, gelatin, agar, agarose or any other viscosity agent, which can be any substance that modifies the viscosity of the coating solution. The concentration of the viscosity agent is typically from about wt. 0% to about 90% of the coating solution.

Whilst a range of therapeutic agents can be used, in one example the agents are vaccines. The vaccine can be composed of DNA or protein and can also contain an adjuvant. The concentration of DNA in the coating solution can be from 0.01 mg/ml to 5 mg/ml. The concentration of protein in the coating solution can be from 0.01 to 50 mg/ml.

The material can include nanoparticles to provide a nanodelivery system. For example the coating can include DNA containing nanoparticles.

In one example, the nanoparticles are multilayered nanoparticles. Outermost layers of the nanoparticles can include cell targeting and cell-entry facilitating molecules. The next layer can include intracellular targeting molecules for precise delivery of the nanoparticle complex inside the cell of interest.

Molecular biosensors can be used to confirm the presence of expected molecules as a surrogate molecule for signs of infection, for activation in radiation damage, or other criteria, prior to delivery of counter-measure molecules such as vaccines, drugs, or gene therapy. The biosensors can also be used as a feedback control mechanism to control the proper amount of vaccine/drug/gene delivery for each cell.

Further, the nanodelivery system can be used to restrict any cells from encountering the drug unless that cell is specifically targeted. Successful targeting can be verified by 3D multispectral confocal microscopy. These single cell molecular morphology measurements can be extended from individual cells, to other cells in a tissue in tissue monolayers or tissue sections.

This example can be used to provide a nanomedical system and method that can be used for diagnostics, therapeutics, vaccines, or a combination thereof by use of a multilayered nanoparticle system. The multilayered nanoparticle system can built on a nanoparticle core of bio-polymer, polystyrene, silica, gold, iron, or other material.

The concentration, viscosity and surface tension will all influence the thickness, morphology and payload of coating. In the most preferred embodiments, the thickness of the coated vaccines can be from 10 nm to 10 μm.

The amount of resulting dry coating on the projections can be controlled by the concentrations of excipients in coating solution, as well as the surface area of the projections, although as mentioned above, selection of an appropriate surfactant, such as QA can avoid the need for unnecessary excipients.

The coating solution can be applied in several ways. In one example, the projections are completely submersed in the coating solution, although alternatively a defined volume of coating solution can be applied to the patch, the amount of which can vary depending on the patch area.

Once the coating solution is applied, the projections and/or the patch are dried. The gas flow can be used to move the coating solution over the patch surface 121, to thereby ensure all the projections 110 are coated. For example, the gas jet can be used to move the coating solution from one edge of the patch to another opposing edge of the patch, by suitable direction of the gas jet. Additionally, and/or alternatively, the gas flow can be used to dry the coating solution on the projections quickly so the coating solution remains on the projections until they are dry. By using the gas drying technique, this ensures that coating is evenly distributed on the projections.

It will be appreciated that in some instances it may be desirable to coat the projections but not the base of the patch itself, for example to control the rate of delivery of the material, and to help reduce excessive usage of coating solution. This can be achieved using a coating solution of proper viscosity and surface tension and a defined drying process. Specific examples of this will be described in more detail below.

In order to allow the coating solution to be distributed over the patch, it is typical to direct the gas flow over the patch in an appropriate manner. An example of apparatus for achieving this will now be described with reference to FIGS. 5A and 5B.

In this example, the gas flow is generated by a gas jet expelled from a nozzle 500. In one example, the nozzle is coupled via a tube 501 to a gas source 502, such as a compressed gas cylinder, a compressor, or the like. This allows the gas source 502 to supply gas to the nozzle 500, via the tube 501, thereby causing a gas jet to be emitted from the nozzle 500 in a direction substantially parallel to a nozzle axis 510. In one example, the gas source 502 includes a control 503, such as a flow rate valve, that allows the flow rate of the gas from the nozzle to be controlled.

Figure 5A:
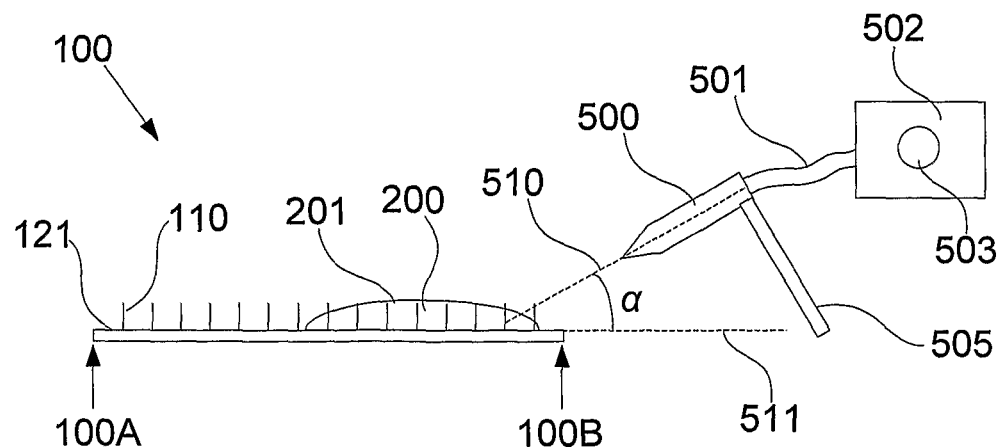
FIGS. 5A and 5B are schematic diagrams of a first example of apparatus for providing gas flow.

As shown in FIG. 5A, initially the coating solution is applied to the surface 120 on one side of the patch 100 near the edge 100B. The nozzle 500 is then aligned with the fluid on the patch, and aimed so as to direct the coating solution towards the other edge 100A of the patch 100. The nozzle 500 is generally aimed so that the nozzle axis 510 is at an angle α relative to a plane 511 containing the patch substrate 120.

Adjustment of the angle α can be used to control the rate at which the fluid is moved across the patch, allowing coating solutions of different viscosities to be moved across the patch prior to drying. It will be appreciated that additional distribution control can also be achieved by adjusting the gas flow rate, although this in turn has an impact on drying rate. Accordingly, it is generally desirable to balance the distribution rate and drying rate for the coating solution by appropriate selection of an appropriate gas flow rate and angle α, which will in turn depend on the viscosity and surface tension of the coating solution. Typically however the angle α is in the region of 0° to 45°, and more typically 10° to 30°, and more typically about 20°.

Figure 5B:
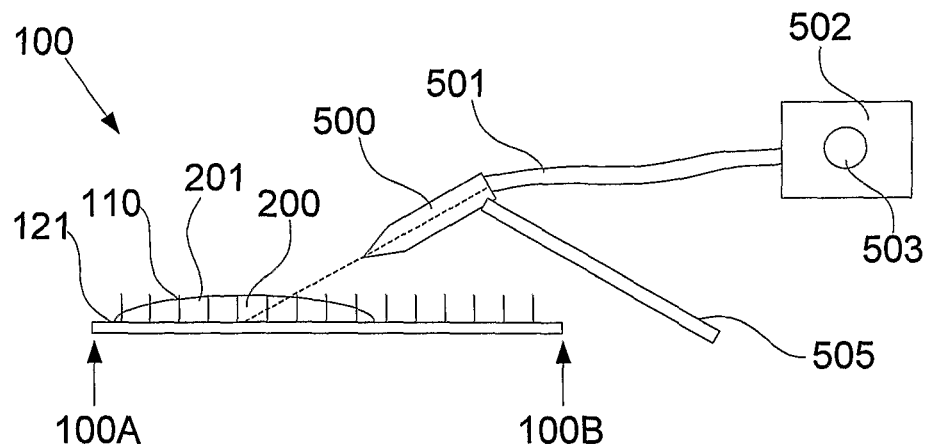

In addition to this, the position of the nozzle 500 can also be adjusted to help distribute coating evenly over the patch 100. This can include moving the nozzle in a direction parallel to the edge 100B, to thereby ensure that coating is distributed across the entire patch width, as well as to move the nozzle in a direction perpendicular to the edge 100B, to thereby move solution along the length of the patch, as shown in FIG. 5B.

In use, the nozzle 500 may also be held in position by a support arrangement 504, which can be any form of suitable support, such as an arm including a clamp, or the like. The support may be capable of manipulation, to allow the position of the nozzle 500 relative to the patch 100 to be adjusted. Thus, in one example, the support 504 could be in the form of a computer controlled arm, such as a robot arm, thereby allowing computer control of the coating process.

It will be appreciated that in addition to the above, multiple gas jets may be used to induce movement and/or drying of the coating solution. Furthermore, the multiple gas jets could be provided at different angles α, as well as at different orientations relative to the patch, to thereby enhance the distribution or drying effect.

Figure 5C:
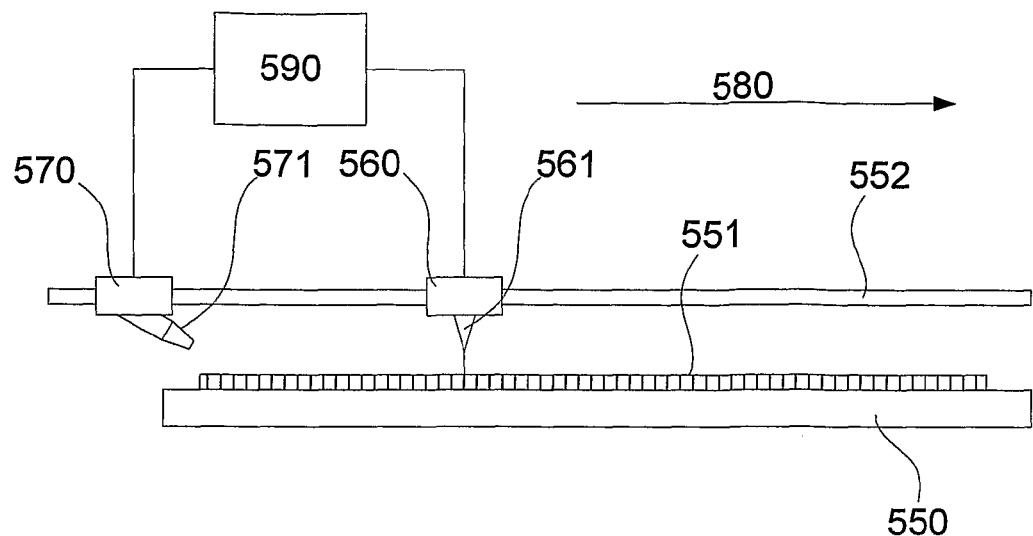
FIGS. 5C and 5D are schematic diagrams of a second example of apparatus for providing gas flow.
Figure 5D:
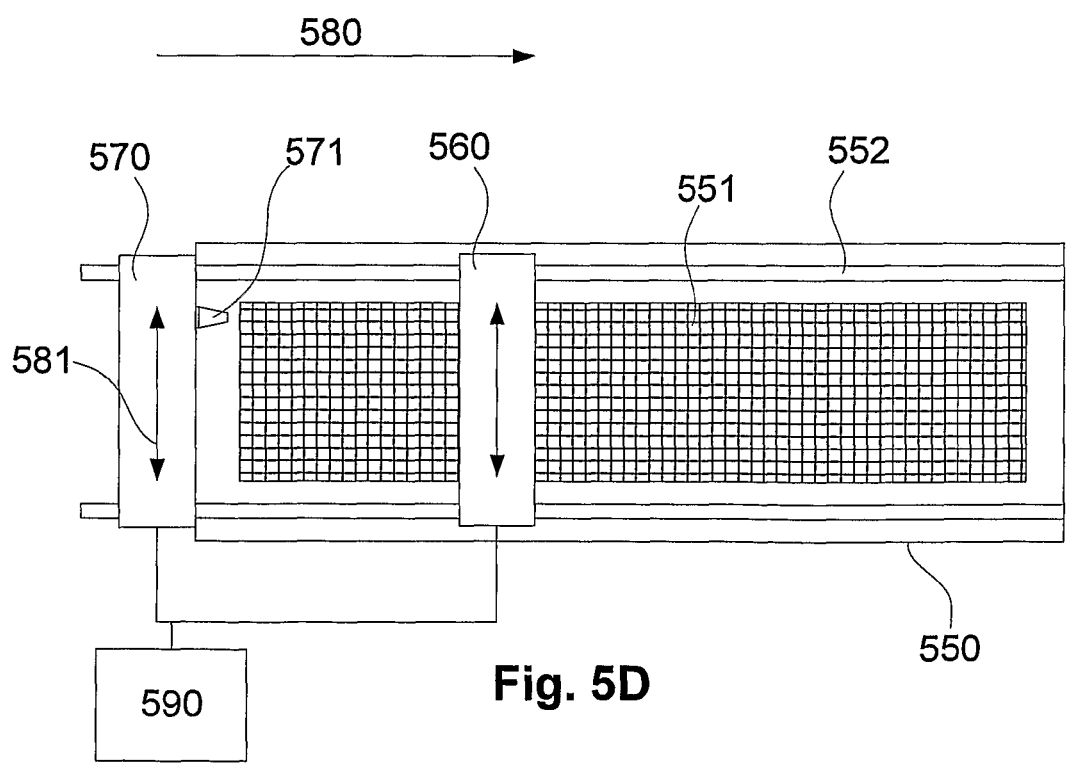

Apparatus of this form can also be adapted to allow multiple patches to be coated during a single process. An example of such apparatus will now be described with reference to FIGS. 5C and 5D.

In this example, the apparatus is formed from a base 550 for supporting a number of patches 551, typically provided in an array. The apparatus includes two supports 552, for supporting two arms 560, 570, which are mounted to allow movement of the arms in the direction of arrow 580. The first arm 560 includes a coating solution delivery system including a nozzle 561 for depositing coating solution on the patches 551. The second arm including a gas delivery system including a gas nozzle 571. In use, the nozzle 561 and the gas nozzle 571 are movably mounted to allow lateral movement of the nozzles 561, 571 in the direction of the arrows 581.

Movement of the arms 560, 570 and the nozzles 561, 571, gas flow rate and coating solution delivery are typically achieved using a computer controlled drive system, shown generally at 590. This allows coating solution and gas flow to be delivered to the patches 551. This can be achieved collectively, or by delivery to each of the patches in turn. In either case, this allows coating solution to be applied, optionally distributed over the patches and dried.

In the example shown, a single respective nozzle 561, 571 is used to deliver coating solution and gas flow. However, multiple nozzles may be provided. Additionally, or alternatively the coating solution and gas delivery systems can be incorporated into a single arm. A further alternative is to provide nozzle systems that extend across an entire length of the arm allowing coating solution and gas to be applied to multiple patches simultaneously.

Further examples of apparatus for providing a gas flow will now be described with reference to FIGS. 6A and 6B.

Figure 6A:
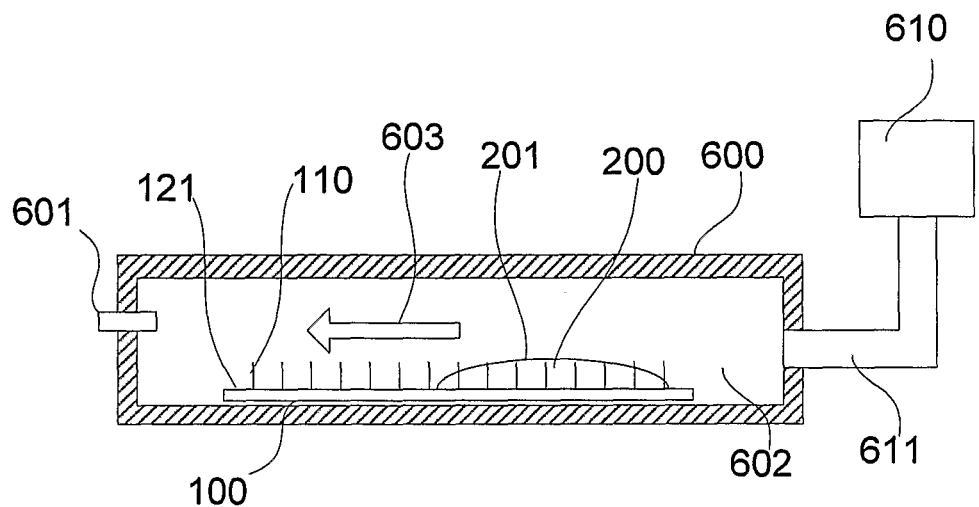
FIG. 6A is a schematic diagram view of a third example of apparatus for providing gas flow.

In the example of FIG. 6A, the apparatus includes a housing 600 having a cavity 602 for containing a patch. In one example, the container is generally sealed to allow a pressure differential to be established between the inside and outside of the housing 600. This can be achieved by coupling the housing to a gas source 610 via a connecting tube 611, allowing the pressure within the housing 600 to be increased to a suitable level. Once this has been reached, a release valve 601 can be activated, allowing gas to escape from the housing 600 through the valve 601. This in turn generates a gas flow, as shown by the arrow 603. The gas flow can be directed utilising appropriate baffles provided on inner surfaces of the housing 600 as required.

As an alternative to pressurising the container however, a further option is to replace the gas Source 610 with a vacuum pump, allowing air or another gas within the cavity 605 to be extracted, to thereby generate a gas flow.

In either case, it will be appreciated that appropriate positioning of the patch 100 within the housing 600, together with a suitable pressure differential, and hence suitable gas flow, can be used to ensure the patch is appropriately coated.

Figure 6B:
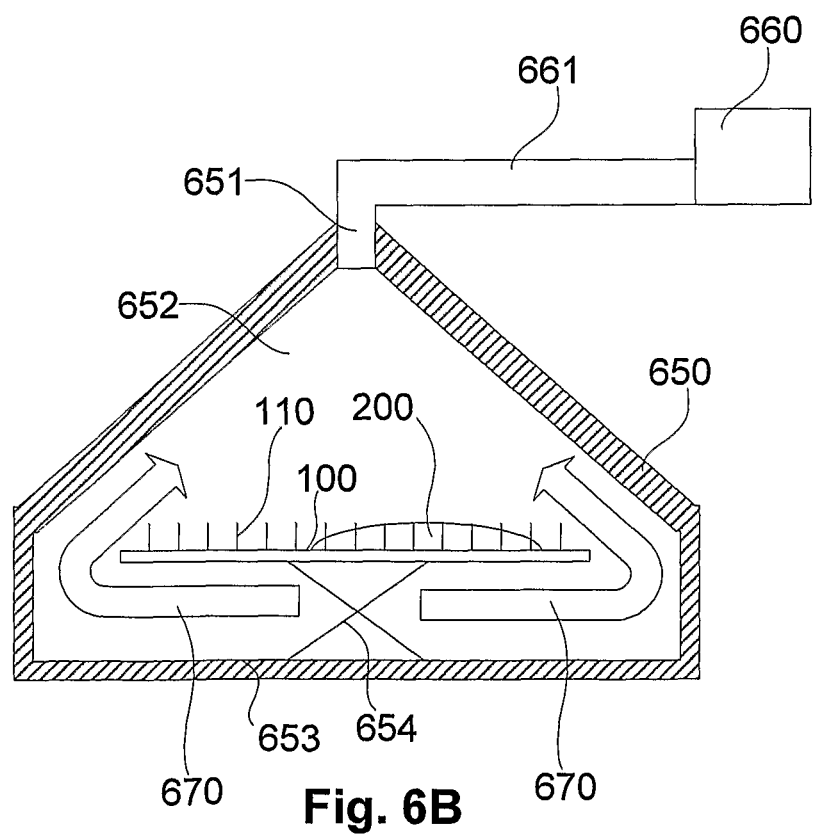
FIG. 6B is a schematic diagram view of a fourth example of apparatus for providing gas flow.

In the example of FIG. 6B, an alternative design of container 650 is shown. In this example, the container includes an opening 651 to allow a cavity 652 to be coupled to a vacuum pump 660, via a connecting tube 661. The patch 100 is supported in the cavity 652 above a lower surface of the cavity 653, using a suitable support 654. The patch 100 is also positioned below the opening 651. Consequently, when air or another gas is evacuated from the housing 650, a gas flow is generated as shown by the arrows 670. As the gas flows around the patch 100 turbulence causes air flow over the entire patch surface, thereby helping to distribute and/or dry the coating solution. It will be appreciated that as an alternative, the cavity 652 can be pressurised in a manner similar to that described above with respect to FIG. 6A.

In one example, only the projections are coated. Consequently, when the patch is placed on the skin, substantially all of the coated therapeutic agent can be rapidly delivered into the skin from the projections. As a result, this can be used where rapid delivery of an agent is required.

However, there are cases where it is required for agent to also be coated to the base. As one example, where some delay is required for delivery of a therapeutic agent, the agent can also be coated onto the patch substrate or base 120. The agent coated on the projections can achieve fast delivery in skin for a first dose, while those coated on the patch base 120 can slowly permeate into the subject's skin through holes made by the projections thereby providing for further dose(s).

As another example, such arrangements may be used when it is desirable to deliver higher amounts of payload into the skin over and above the amount coated on the projections. In this case, the additional payload on the base of the patch can be hydrated (e.g. by fluid within the skin moving through holes generated by the projections with a capillary action) and released, a "depot effect" for higher delivery dose.

An example of this will now be described with reference to FIGS. 7A and 7B.

Figure 7A:
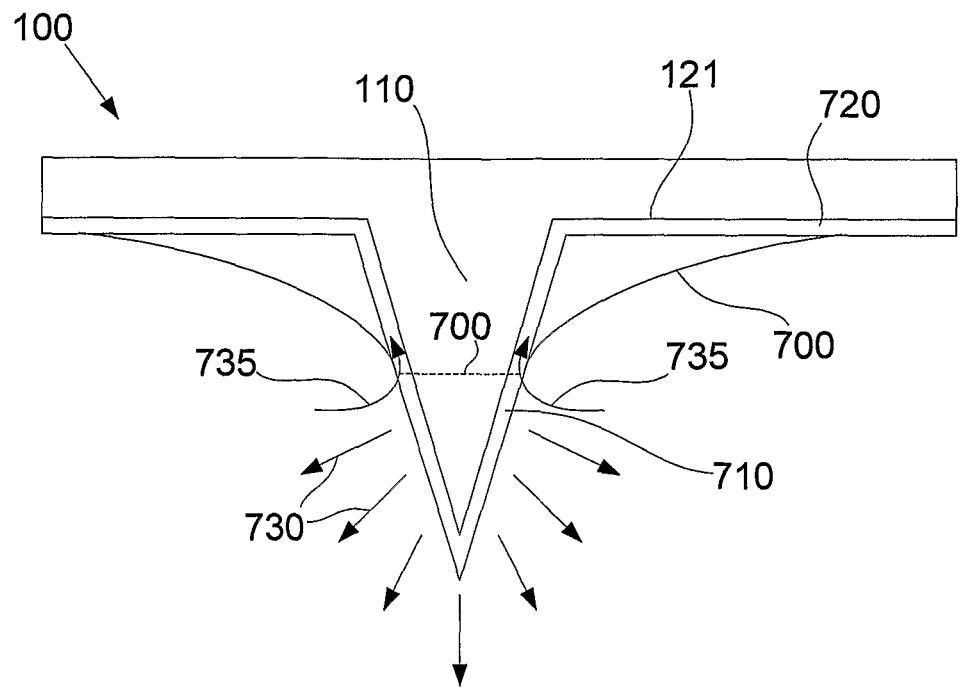
FIGS. 7A and 7B are schematic diagrams illustrating the transfer of coating material to a subject, in use.
Figure 7B:
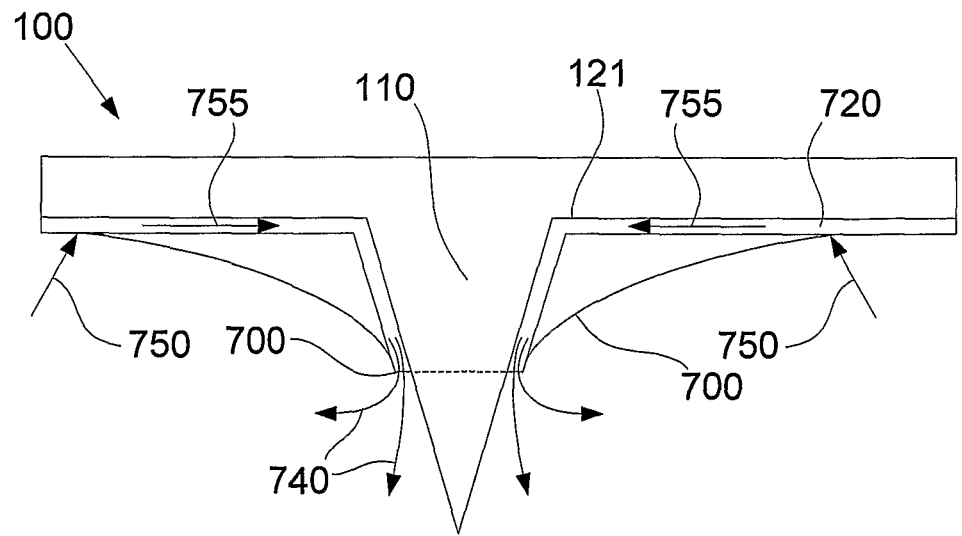

In the example of FIG. 7A, the patch 100 includes coating 710 provided on the projection 110, and coating 720 on the surface 121. Initially, when the patch 100 is applied to a subject, the projections 110 extend through the skin 700. The skin typically deforms in a region immediately surrounding the projection, with the skin bowing down away from the patch surface 121.

Upon insertion into the skin 700, coating 710 on the tip of the projections 110 below the skin surface 700, will immediately begin to hydrate and dissolve, thereby being dispersed into the subject, as shown by the arrows 730.

In addition to this, fluid from the subject will gradually flow into the coating 710 at the base of the projection 110, and coating 720 on the surface 121, as shown by the arrows 735, thereby hydrate the fluid. This will in turn cause fluid to diffuse into the subject, as shown by the arrows 740.

A further effect that can contribute to the delivery of material from the patch surface 121 is a squeezing effect, caused by the resilience of the skin 720, which urges the skin upward as shown by the arrow 750, which in turn urges hydrated material in the direction of the arrow 755, thereby increasing delayed delivery to the subject.

It will therefore be appreciated that controlling the coating ratio can therefore be used to manipulate the amount and rate which material is delivered to the subject. By maximising the coating on the projections, this maximises rapid delivery of material. However, by increasing the amount of coating on the surface 121, this increases the delayed delivery of material.

Figure 8A:
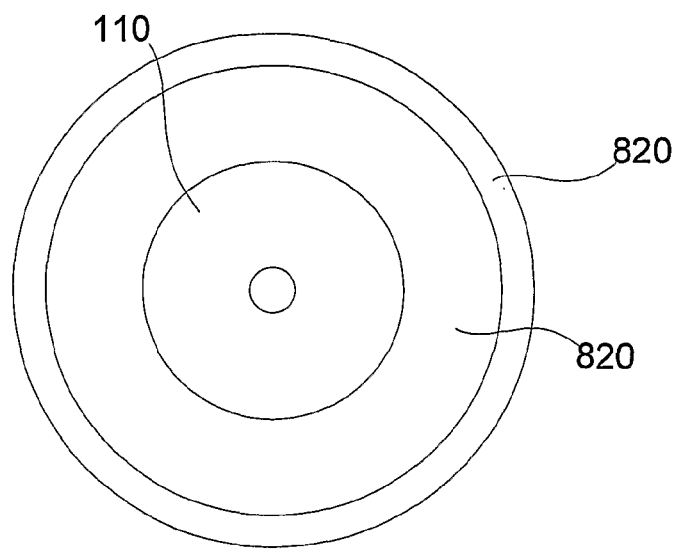
FIGS. 8A and 8B are schematic diagrams of an example of a well provided at the base of a projection.
Figure 8B:
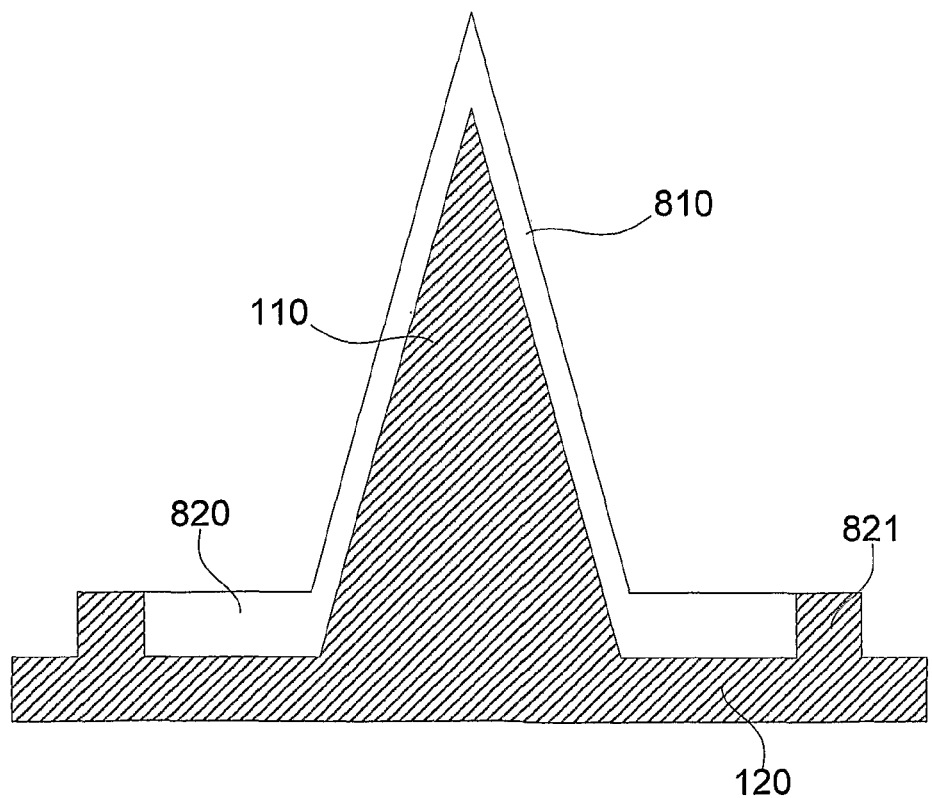

Further delayed delivery of material can be achieved by further increasing the amount of material on the surface. This can be achieved using a projection configuration as shown in FIGS. 8A and 8B.

In this example, the surface 121 includes a raised annular portion 821 surrounding the base of a projection 110, thereby providing a well for containing addition coating solution. Accordingly, in this instance, the coating 820 on the surface 821 can be of an increased thickness in the region immediately surrounding the base of the projection 110. This enhances the delayed delivery of material to the subject.

In one example, the projections can be coated a single time. In a further example, the projections can be coated a number of times. This can be used to allow a required thickness of coating to be achieved. In addition to this however, this allows different coating regimes to be used, which in turn allows greater control over the coating process.

Thus, for example, if coating is carried out using a first set of appropriate coating properties, then the coating can be confined primarily to the tips of the projections. A second coating procedure can then be performed in order to allow the entire projection to be coated. This can be used to ensure that the tip includes a suitable amount of material to maximise the efficacy of the delivery process.

The above described processes therefore allow projections to be dry coated with material. In one example, this is achieved by using a gas flow to move or distribute coating solution over the patch to thereby ensure that all projections are wetted prior to drying. In another example, this is achieved by using as gas flow to dry coating solution more rapidly than can be achieved under ambient conditions, thereby ensuring that coating solution remains on the projections during the drying process. It will be appreciated that the moving and drying steps can be performed simultaneously.

By dry coating the projections of the patch, this ensures that material on the projections is rapidly delivered directly to the subject. This maximises the proportion of coating material effectively delivered to the subject, which in turn reduces the amount of material required in order to produce a biological effect within the subject.

In addition to the above, appropriate selection of coating properties, such as gas flow rate, drying time, and solution properties can be used to further control the coating process. In particular, this can be used to control the thickness of the coating applied to the projections.

The projections can be coated with DNA or protein vaccines. However, in addition to this, many other reagents can be coated using this process including both inorganic and organic materials. Example coatings used include inorganic materials such as EtBr, or organic materials such Evans blue, Dextran, DiD, or the like.

Consequently, the resulting patch can provide small and densely packed projections that can be uniformly and controllably coated. This allows vaccines or other agents to be subsequently delivered to highly immunologically sensitive cells within the epidermis, or to the blood or muscular tissue as required.

In use, the coated and dried projection patches are applied to the skin of a mammal by placing the patch on the skin. The coated and dried projection patches can be tested on skin or skin analogs and the conditions for optimal coating release determined. These conditions include patch application time, force, velocity, strain-rate of insertion, temperature, humidity, location, and skin pretreatment. This process can be done in vitro, ex vivo or in vivo.

It will be appreciated that the final release of the therapeutic agent can also be influenced by several of the coating properties such as the inclusion of excipients and viscosity enhancers, as well as the coating thickness, and testing again allows optimum coating properties such as those outlined above, to be determined.

The in vitro method utilizes a thin polymer film to approximate the stratum corneum (SC), or outer layer of skin. The film can be polycarbonate, polyethylene, or any other film that has physical characteristics that approximate those of the SC. Beneath the polymer is an absorbent material that can be filter paper, polymer mesh, or any other soft and inert material that does not bind the vaccine or coating material. This material is then moistened with water, tris buffered saline (TBS), phosphate buffered saline (PBS), or any other liquid that can dissolve the coating material. The device is then applied to the polycarbonate and the projections pierce the top layer of polymer film. The liquid in the absorbent layer can then dissolve the dry coating. Once the device is removed the absorbent layer is flushed with the liquid. The elutate is then quantified and the device release calculated. The coated and dried projections patches can be applied to this testing environment under many varied conditions to optimize release.

The ex vivo release assay can be used to assess release from the coated and dried projection patches and employ skin. A patch of skin is dissected from a donor (i.e. mouse, pig, rat, human) and kept at −20° C. for less than 7 days prior to use. The skin is warmed to 37° C. and the patches coated as outlined above are applied under a variety of conditions. The patches can be coated with fluorescent dyes such as FITC, Evans Blue, Propidium Iodide, Ethidium Bromide, Alexa Fluor dyes. The patches can also be coated with DNA or proteins that are labelled with fluorescent dyes. Alternately, the patches can be coated with fluorescent dye labelled polymers like dextran, agarose, agar or any other biocompatible polymer that approximates the size, shape, and chemical nature of DNA and protein vaccines.

The release of these fluorescently labelled agents in skin can be monitored by methods including multi-photon/confocal microscopy, fluorescence microscopy, spectrofluorometer, and flow cytometry. Multi-Photon/Confocal microscopy can give real time, 3D patch release information that is necessary for optimizing the device coating and application.

In in vivo release testing, a coated projection patch is applied to the skin. After the application, analysis was carried out as discussed for the ex vivo testing protocol. Alternately, a portion of the skin treated with the projection patch is excised. The outer layer of the skin is peeled and trimmed as required. The skin is snap frozen in liquid nitrogen and then pulverized to a fine powder.

For DNA vaccine delivery, the DNA is extracted with a Qiagen extraction kit and a standard curve employed to determine the amount of DNA with semi-quantitative Polymerase chain reaction (PCR).

A number of specific examples will now be described. For the purpose of these examples the general coating procedure used was as follows:

Patches are cleaned in glycerol:$H_2O$ (1:1) for 10 minutes and then flushed with plenty of water;
Cleaned patches are dried with nitrogen blow;
Coating solution is made of MC, poloxamer 188 or QA, and different concentration of vaccine (0.01 mg/ml-50 mg/ml), the concentrations of chemicals being adjusted to suit different requirements;
5~15 microliters of coating solution is dropped onto each patch; and,
Patches are dried under nitrogen flow as described above.

During application the skin of the subject is typically hydrated to ease application of the patch, and increase hydration of the coating, thereby enhancing delivery.

Example 1

The projection patches are cleaned in a mixture of glycerol and water in a 1:1 ratio for 10 minutes and then flushed with plenty of water. The patches are then dried with nitrogen blow. Example of cleaned and uncoated projections are shown in FIGS. 9A to 9D, which show secondary electron and backscattered electron images for patches with 60 µm and 90 µm long projections, respectively.

A coating solution containing a viscosity enhancer (MC), a surfactant (QA or poloxamer 188) and different concentrations of vaccine (OVA protein or DNA) is prepared. The compositions are set out in Table 1. All percentages are weight percentages of the total compositions unless otherwise indicated.

TABLE 1

| MC | wt. 0-2.5% |
| QA or poloxamer 188 | wt. 0-1% |
| OVA DNA | wt. 0-0.5% |
| OVA protein | wt. 0-5% |

10 microliters of the coating solutions are dropped onto each patch prepared as described above. A gas jet is used to control the movement of coating solution on patches so the liquid can wet the projections without being stuck on patches and covering many projections. In the meantime, the coating solution can be adsorbed and dried on the projections.

In this example, to provide a comparison, the patches of FIGS. 9A and 9C were treated using a classical dip coating approach. Four patches, having totally over 14,000 projections, were coated with a solution containing 10 mg/ml of CMC (viscosity enhancer), 10 mg/ml of poloxamer 188 (surfactant) and 2 mg/ml of OVA DNA (active agent). Patches were dipped into the solution for 10 seconds and dried in air for 1 hour. The morphology of coated patches was then observed by SEM, with the results being shown in FIGS. 9E and 9F.

FIG. 9E shows that no coating is present on the projections. Instead, the coating solution has been exclusively dried on the base the patch. From the magnified image of a single projection, shown in FIG. 9F, the sputter coated gold particles can still be clearly observed, which also confirms that no coating has been obtained on the projection. This highlights that a dip-coating technique is not effective when applied to very small and densely packed projections. This experiment was repeated when MC, QA and OVA protein were used in coating solution at different concentrations and the results were similar. In other words, no coating or very little coating can be obtained on projections by using the dip-coating technique.

Figures 10A, 10B:
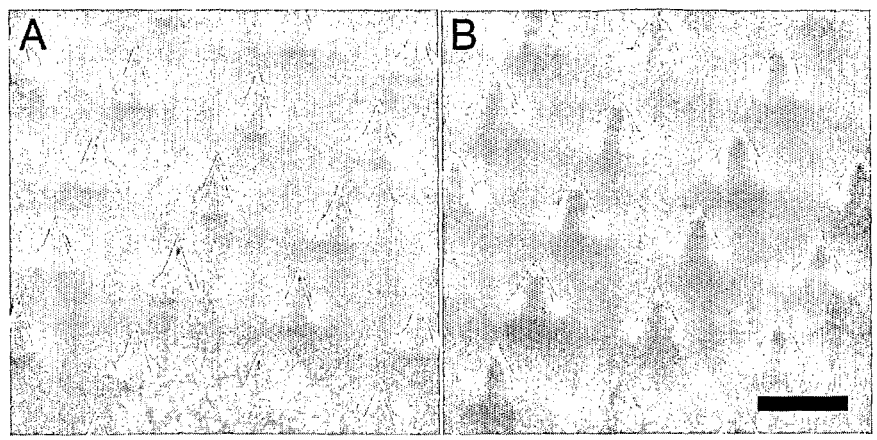
FIGS. 10A and 10B show examples of SEM images of 35 μm long projections before and after coating, respectively, using a gas flow.
Figures 10C, 10D:
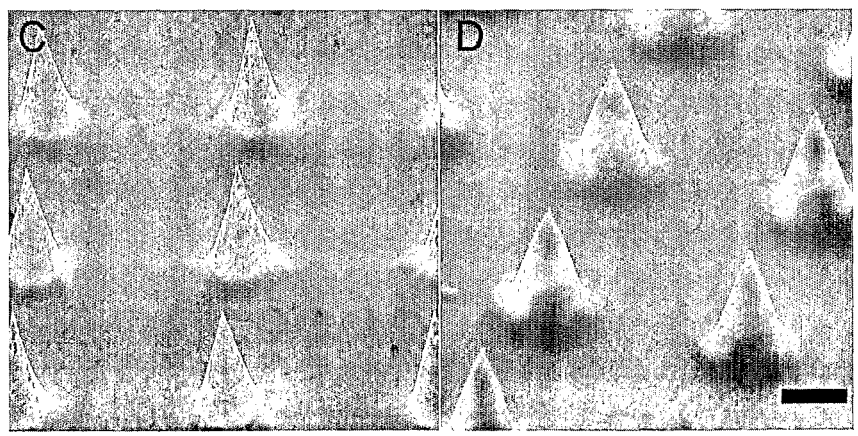
FIGS. 10C and 10D show examples of SEM images of 60 μm long projections before and after coating, respectively, using a gas flow.

Gas-jet drying was used to coat vaccines on patches and SEM was employed to characterise the morphology of the coating. FIGS. 10A and 10C show baseline secondary electron images of uncoated patches, with 30, 60 and 90 µm long projections, respectively.

The patches were then coated using a coating solution composed of 20 mg/ml of MC, 2 mg/ml of Quil-A and 2 mg/ml of OVA DNA vaccine, which was dried using the gas flow technique outlined above. The respective SEM images of the coated patches are shown in FIGS. 10B, 10D, 10E and 10F, which highlight how the effective thickness of the projection increases, due to the coating of a consistent layer. The coating layer is up to 5 µm thick.

Figures 10E, 10F:
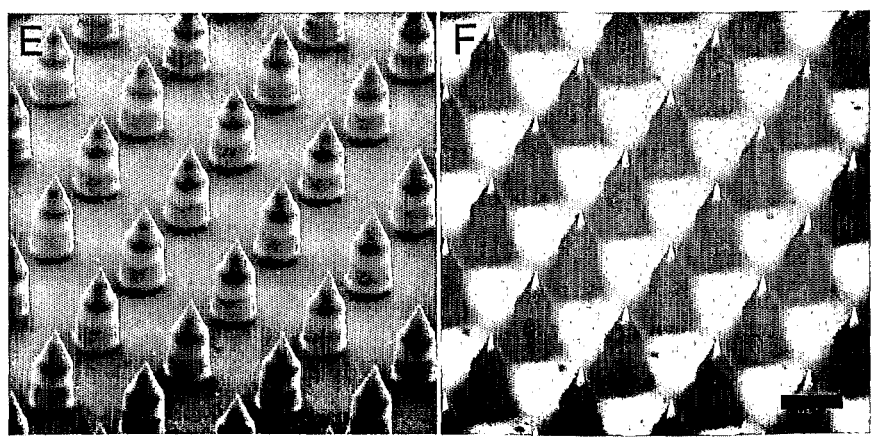
FIGS. 10E and 10F show examples of secondary and backscattered electron images, of 90 μm long projections after coating using a gas flow.
Figure 13A:
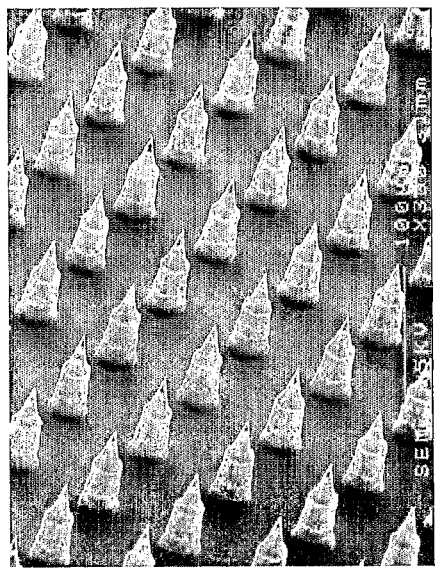
FIGS. 13A to 13D show examples of secondary electron images for patches coated with OVA DNA vaccine on 90 μm projections with concentrations of MC of 0%, 0.5%, 1% and 2.5%, respectively.
Figure 13B:
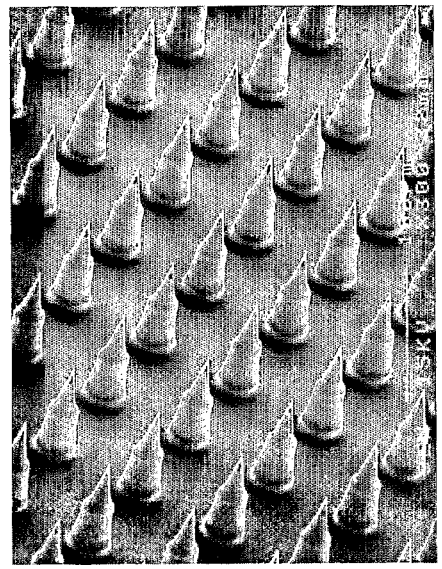
Figure 13C:
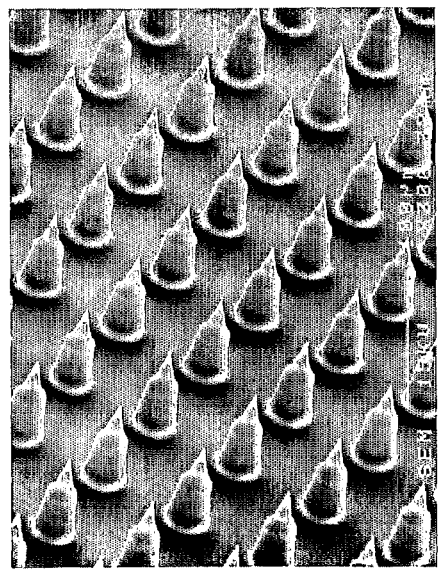
Figure 13D:
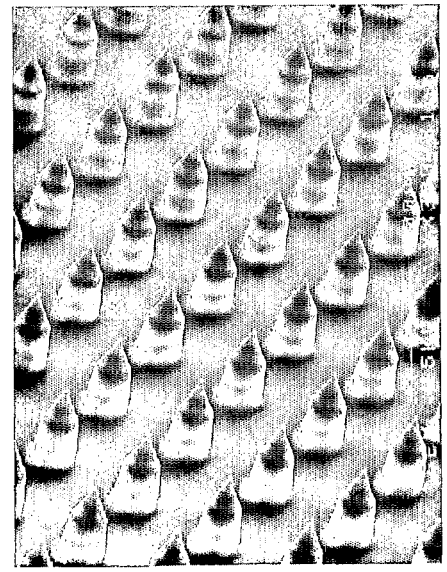
Figure 14A:
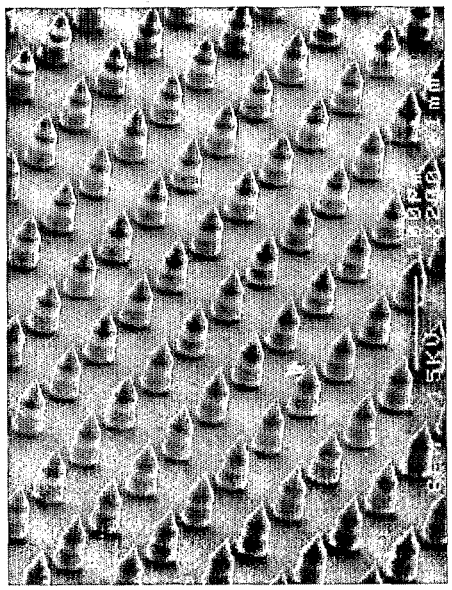
FIGS. 14A and 14B show examples of secondary electron and backscattered electron images, respectively, for patches coated with OVA protein vaccine on 90 μm projections, with concentrations of QA of 0.2%.
Figure 14B:
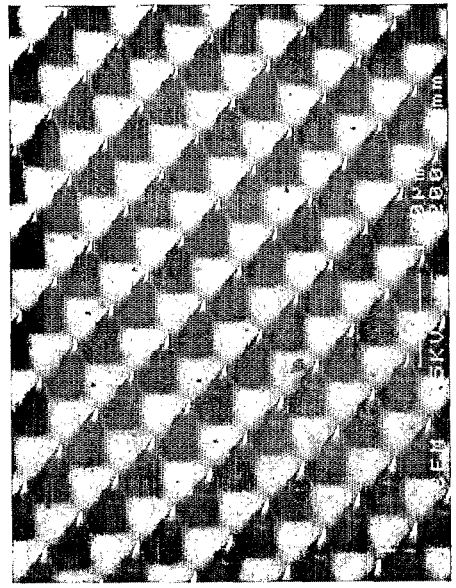
Figure 14C:
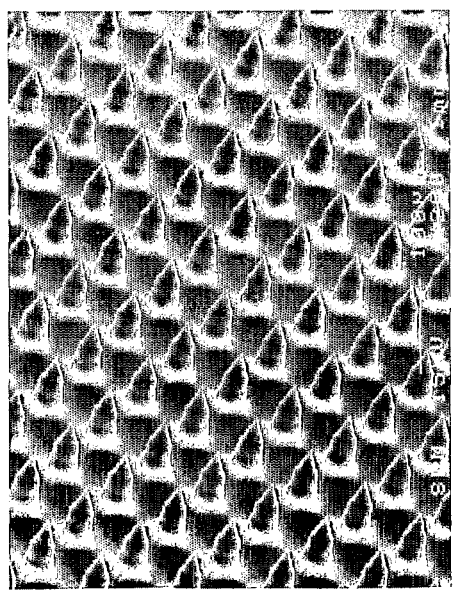
FIGS. 14C and 14D show examples of secondary electron and backscattered electron images, respectively, for patches coated with OVA protein vaccine on 90 μm projections, with concentrations of QA of 1%.
Figure 14D:
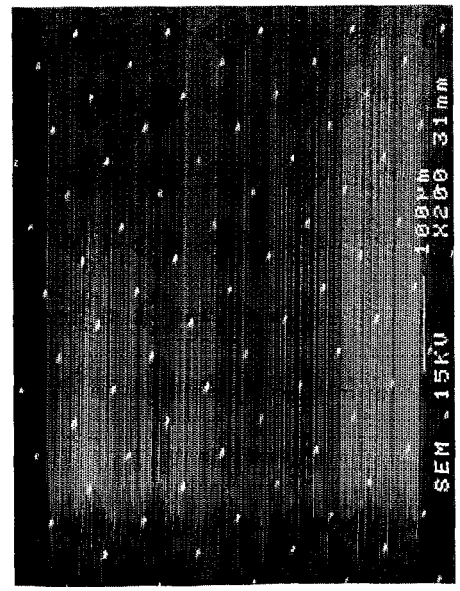

The image in FIG. 10F is a backscattered electron image, which also confirms that the projections are uniformly coated. In this regard after coating, projections presenting dark BSE signals are seen due to the presence of organic materials with low atomic numbers, i.e. carbon, oxygen, and hydrogen, on the surface of projections. In comparison, the base of the patch still has bright BSE signal after coating, which suggests that the coating on the base is very thin (~1 µm).

In FIGS. 11A to 11I, the coating on selected, individual projections are shown in more detail. FIGS. 11A, 11B and 11C show an individual 35 µm long projection before coating, after coating, and an overlay of the two images, respectively. With a longer, 60 µm projection, these images are respectively shown in the same series in FIGS. 11D, 11E and 11F. From these figures, the coating layer on the projections can be clearly observed.

With consistent coating of projections established, the next stage is to demonstrate that biologically active (or relevant) material was uniformly coated on the projections, to show that the projections are not only other excipients, such as, viscosity enhancers, surfactants, or the like. In this regard, FIGS. 11G, 11H and 11I show the fluorescence from a DiD coating on 90 µm projections, a reflection from the projections and an overlay image, respectively. These figures demonstrate that surrogates for active materials in the form of fluorescent dyes can be uniformly coated on projections, as shown the fluorescence from DiD.

Following this, the work was extended to demonstrate that the coating process is robust and broadly applicable to many active entities, including ethidium bromide (EtBr), OVA protein vaccine, OVA DNA vaccine, fluorescent dyes (dextran and DiD) and flu virus on projections. The selection of coated compounds spans from low molecular weight molecules (a few hundred Daltons) to high molecular weight molecules (a few million Daltons). In all cases, coatings were reproducibly applied onto projections on the patches.

FIG. 12A shows an example of an SEM image of a patch uniformly coated with protein using a gas flow. The secondary and backscattered electron images of FIGS. 12B and 12C highlight the even coating.

Accordingly, the gas-jet coating can achieve uniform coating on projections and can rapidly coat large numbers of projections.

Example 2

In this example, the projections are coated in accordance with Example 1, however with the concentration of MC in coating solution being adjusted from 0 to 2.5% while the concentration of QA and OVA protein is kept to be 0.2% and 1%, respectively.

FIGS. 13A to 13D, show secondary electron images for patches coated with OVA DNA vaccine on 90 μm projections with concentrations of MC of 0%, 0.5%, 1% and 2.5% respectively. The coating is pretty uniform for all samples, but the coating thickness is different for coating solutions containing different concentration of MC. This is shown in Table 2, which shows the coating thickness on the middle cylindrical part of projections for coating solutions containing different concentration of MC.

TABLE 2

| MC concentration | Coating thickness |
|---|---|
| 0 | <0.25 μm |
| 0.5% | 1.42 ± 0.18 μm |
| 1% | 2.10 ± 0.18 μm |
| 2.5% | 4.00 ± 0.50 μm |

Example 3

Projections are coated in accordance as described in Example 1 but with a concentration of QA in coating solution of 0.2% or 1% while the concentration of MC and OVA protein is kept to be 2% and 1%, respectively.

FIGS. 14A to 14D show secondary electron and backscattered electron images for patches coated with OVA protein vaccine on 90 μm projections, with concentrations of QA of 0.2% and 1%, respectively. The coating is again pretty uniform for all samples, but the coating thickness on the base is different for the different QA concentrations.

When the concentration of QA is 0.2%, the coating on base is very thin (<1 μm), so very bright backscattered electron signal can be detected from the base, as shown in FIG. 12B.

When the concentration of QA increases to 1%, the coating on base starts to be thicker (>2 μm). Therefore, the backscattered electron signal from gold under the OVA protein coating is difficult to be detected and the base looks dark in backscattered electron image of FIG. 14D.

Example 4

In this example, the projections are coated with OVA protein in accordance with Example 1, but with the coating solution containing water and ethanol (2:1), 1% OVA and 1% MC.

Figures 15A, 15B:
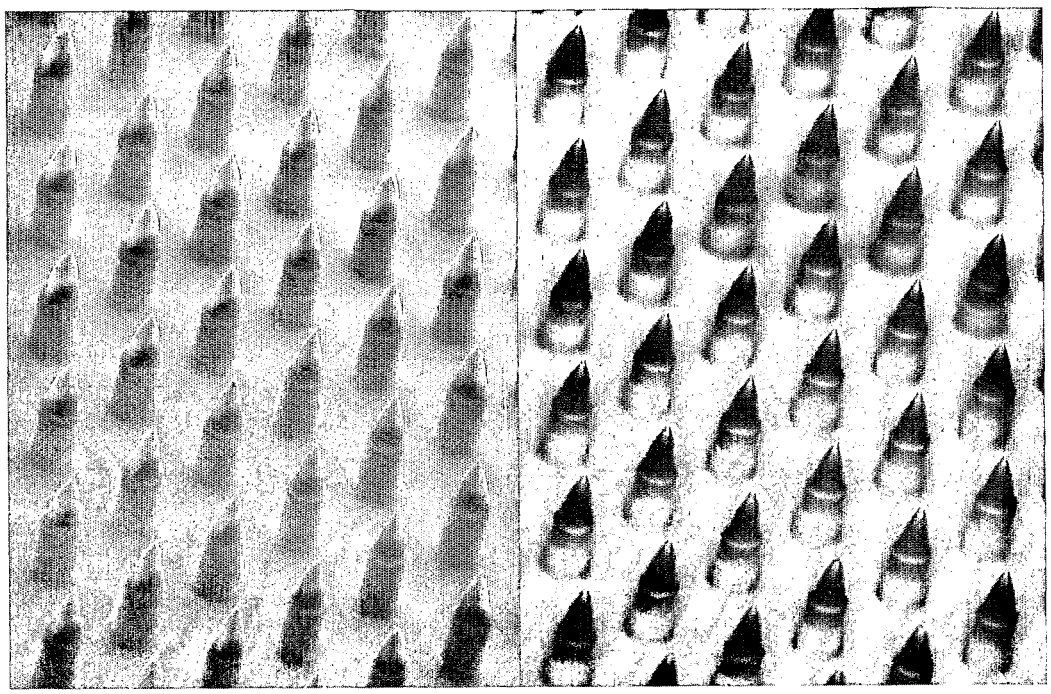
FIGS. 15A and 15B show examples of secondary electron and backscattered electron images, respectively, for an example of the tip of the patch coated with of OVA protein on 90 μm projections.

FIGS. 15A and 15B show a secondary electron and backscattered electron images for an example of the patch coated with of OVA protein on 90 μm projections. It can be seen the coating is mainly on the top part of projections. From the backscattered electron image, it can be seen that the top part of projections look dark while the bottom part of projections and base are bright. This further confirms that the coating is mainly on the top part of projections. After addition of ethanol, the surface tension of the coating solution is very low, so it can well wet projections. Therefore, less amount of coating solution (<6 μl) is enough for coating a patch, which will reduce the cost of vaccine coating required to coat a patch.

Figures 15C, 15D:
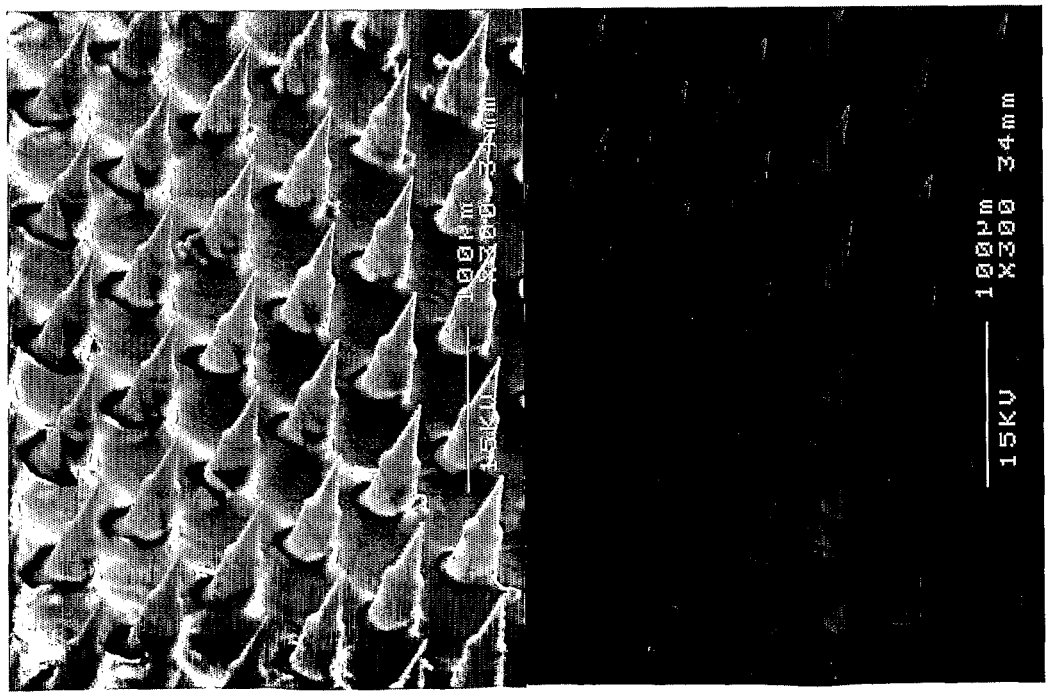
FIGS. 15C and 15D show examples of secondary electron and backscattered electron images, respectively, for an example of the patch coated by applying 10 μl of OVA protein coating solution dried in air.
Figure 16:
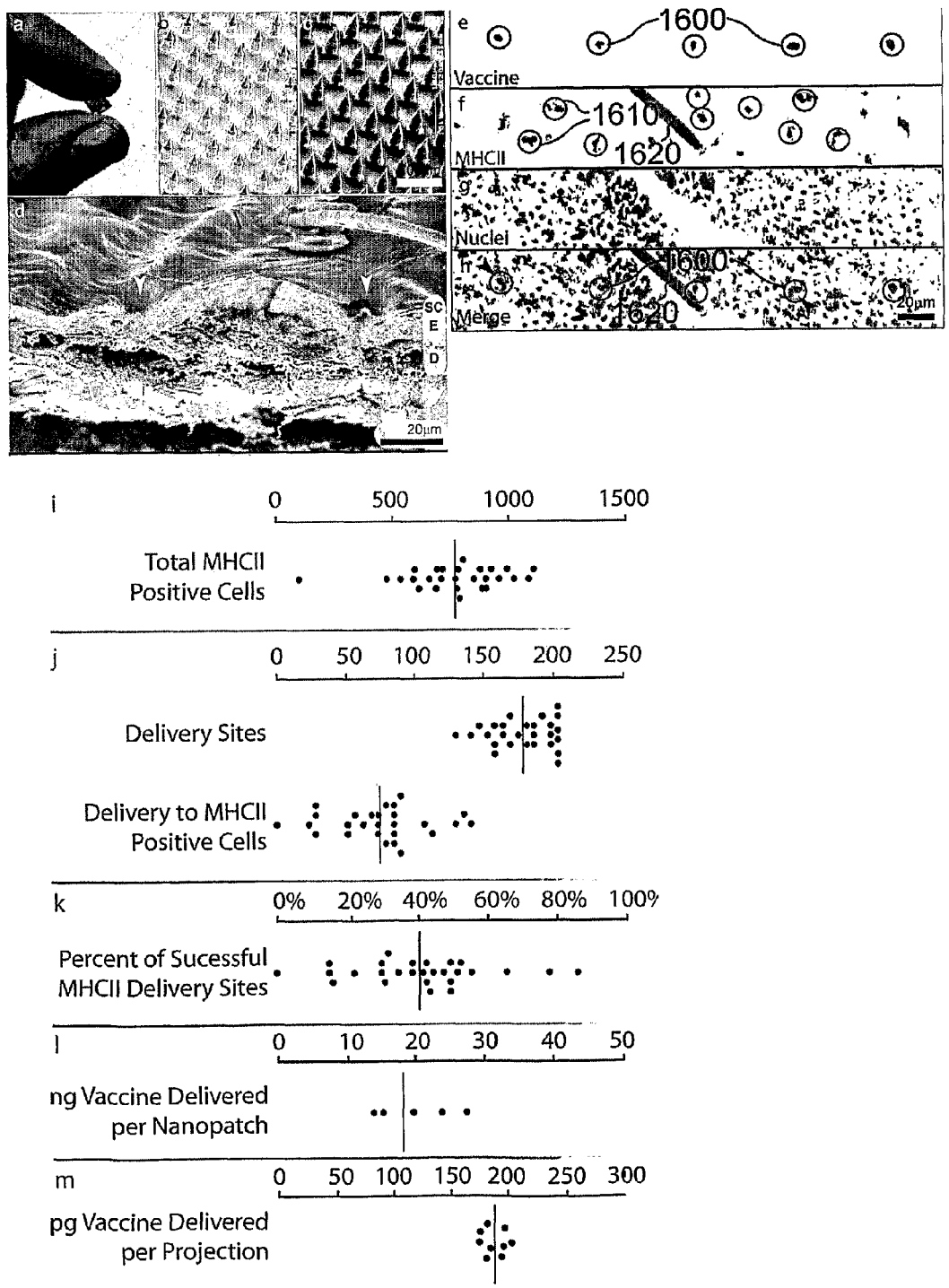
FIG. 16 shows an example of patches and measured local delivery characteristics in mouse epidermis.

To further confirm that the tip coating effect is caused by using a gas jet flow, FIGS. 15C and 15D show examples of secondary electron and backscattered electron images for an example of the patch coated by applying 10 μl of OVA protein coating solution and drying in air. It can be seen that the coating is mainly on base and little coating is on some part of projections.

Example 5

Hardness and Young's modulus are two important mechanical properties for vaccine coating. In order to deliver vaccine into the skin, coating should be robust enough to pierce into skin without wiping off. Preferably, values of hardness and Young's modulus of vaccine coating should be larger than those of skin. Hardness and reduced modulus have been measured for silicon patch, gold coated silicon patch, OVA protein coating and mouse ear skin. Results are shown in Table 3.

Young's modulus can be calculated from reduced modulus. Young's modulus describes tensile elasticity, or the tendency of an object to deform along an axis when opposing forces are applied along that axis; it is defined as the ratio of tensile stress to tensile strain. Hardness is the characteristic of a solid material expressing its resistance to permanent deformation. From the results, it can be found that the values of hardness and reduced modulus of OVA protein vaccine coating are much higher than those of mouse ear skin or porcine skin. It is a clear evidence of robust coating, which should be able to pierce into skin without wiping off.

TABLE 3

| | Hardness (GPa) | Reduced modulus (GPa) |
|---|---|---|
| Silicon patch | 12 ± 0.47 | 173 ± 5 |
| OVA coated patch | 0.14-0.19 | 3.2-3.8 |
| Porcine skin stratum corneum (SC)* | | Dry SC: 0.1-0.3<br>Wet SC: 0.01-0.05 |

*Yuan Y. and Verma R., Colloids and Surfaces B 48 (2006) 6-12

It should be noted that in the case of the porcine skin stratum that the application of the patch was performed under differing conditions. In this regard, the patch was initially applied with the skin in a dry state, yielding a higher reduced modulus for the coating than when the skin is wet. The reason for this is the fluid on the skin hydrates the coating, reducing adherence of the coating to the projection. In some circumstances, this can be beneficial as it assists rapid delivery of the all the coating material to the subject.

Example 6

In this example, a coated patch is tested using a conventional commercially-available influenza vaccine (trivalent vaccine (Fluvax® 2007) CSL, Ltd, Melbourne Australia; consisting of viruses New Caledonia A, Wisconsin A and Malaysia B)) to assess the local delivery of vaccine within the skin (viable epidermis and dermis), as shown in FIG. 16.

FIG. 16 shows that applying patches, coated with the influenza vaccine, to the skin (for 15 minutes) achieves targeted delivery to the skin viable epidermis and underlying dermis. Within the viable epidermis the co-localization of vaccine to targeted immunologically-sensitive cells is very high (at 40%). Furthermore, the overall payload delivered within the skin is accurately quantified at 19.9±5.7 ng (per patch).

In particular, FIG. 16 shows an example of patches and measured local delivery characteristics in the mouse epidermis. Patches (a) were fabricated to the projection length of 90 μm (with Deep Reactive Ion Etching; at the Rutherford Appleton Laboratories, by Derek Jenkins) and then dry-coated with vaccine and photographed with SEM (b) and (c).

Once coated, the patch was applied to the skin and Cryo-SEM was used to visualize the skin during patch application (d). By labelling Fluvax with a fluorescent dye (Cy3), shown at 1600 in (e) and (h), confocal microscopy was used to examine co-localization (arrow heads in Panel (h)) of vaccine with MHCII, shown at 1610 in (f) and (h) containing cells (e) to (h).

The patch was applied at 1.89 m/s and held in place with 500 g for 15 minutes, penetrating to 27.7 µm (which is deeper than the epidermis thickness of 17 µm. The images (e) to (h) are a projected z-stack of the surface of the mouse skin (a hair can be seen at 1620 in (f) and (h) as a large diagonal bar) to the depth of 46 µm (which is well into the mouse ear dermis).

The dense nuclei in (g) and (h), stained with Hoechst 33342, in the epidermis were used to determine the epidermal and dermal boundary. Successful vaccine targeting to key epidermal cells (MHC Class II stained, including Langerhans cells) can be seen in two of the five vaccine deposition sites within Panel (h), highlighted with white arrow heads.

Several parameters were quantified through confocal image analysis (i) to (m) and are shown as per mm$^2$ unless otherwise noted. Nine areas in three patched ears were imaged and analyzed for all but the last two graphs (l) and (m). The final two graphs (l) and (m) show quantification of delivered vaccine payload in skin by patches. Patched mouse ears were then homogenized and used in a quantitative dot-blot, using the generated standard curve, on five mice ears. The mass of vaccine delivered per projection was determined by measuring the integrated density of nine single projections and calculating the percentage of fluorescence per projection. This was then used in conjunction with the total delivery mass to calculate the mass of Fluvax delivered per projection.

Example 7

In this example, ex vivo release kinetics of 70 kDa dextran coated 60 µm nanoprojections were determined. These data were captured over 40 minutes in living skin using fluorescent microscopy.

Projections were coated with 20 µg of rhodamine labelled dextran (70 kDa) as a surrogate for ovalbumin in 2% melthylcellulose. Confocal imaging commenced immediately after patch application with the patch in place.

4D release kinetics from 70 kDa payload in living skin are shown in FIGS. 17A and 17B. FIG. 17A shows raw intensity values over 42 minutes, whereas FIG. 17B shows the calculated diffusion coefficient over the first 15 minutes.

The data were gathered from 20 µm above the tip 1710 of projection 1700, as shown by the arrowhead 1720 in FIG. 17C. The projection 1700 is pointing down and the region 1730 represents payload release. The colored cubes 1740 (2 µm$^3$ and 2 µm away from the projection) show the 3D space that is being analyzed.

Example 8

In this example, groups of five C57BL/6 female mice aged 6 to 8 weeks were vaccinated with chicken egg albumin (Ovalbumin) protein either intramuscularly using the conventional syringe and needle, or onto the interior part of the ear skin using protein coated patch. The coating solution contains 10 mg/ml of MC, 10 mg/ml of OVA and 2 mg/ml of QA. The area of each patch is 0.16 cm$^2$. One patch per each ear was used in the vaccinations (i.e. a total of 2 patches per mouse). The patch was inserted into the skin at a speed of 1.96 m/s. The patch was kept for a further 5 minutes for the coated vaccine to be released. After 21 days, mice were bled and sera collected.

The serum samples were assayed by Enzyme-Linked ImmunoSorbent Assay (ELISA) using plates coated with Ovalbumin. Intramuscular immunised mice were injected with 6 µg of OVA protein per mouse. MNP patch immunized mice were anesthetised and a single patch was applied to each ear, resulting in a total of 4.4±1.4 µg of OVA protein delivered per mouse. The antibody levels of mice, including unimmunised, intramuscular immunised and coated patch immunised mice, are shown in FIG. 18.

Figure 18:
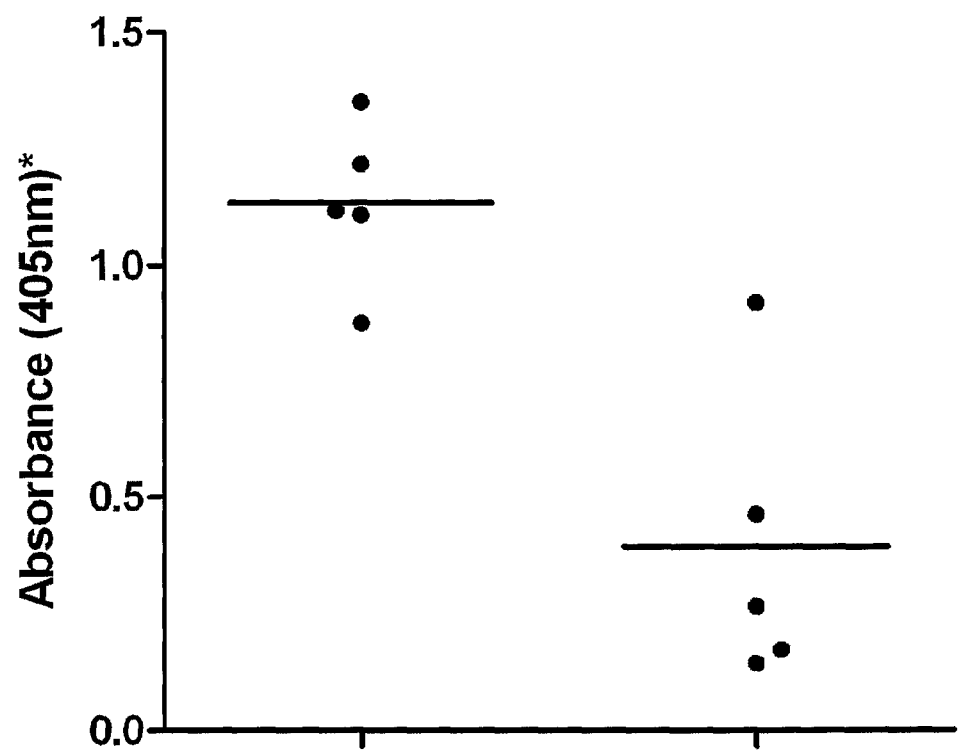
FIG. 18 is an example of comparative results of serum samples for five mice vaccinated with chicken egg albumin protein using a syringe and needle, or a protein coated patch.

The data shown in FIG. 18 demonstrates that much greater immune responses can be achieved by using coated patches at a similar dose with conventional needle and syringe.

Example 9

Figure 19A:
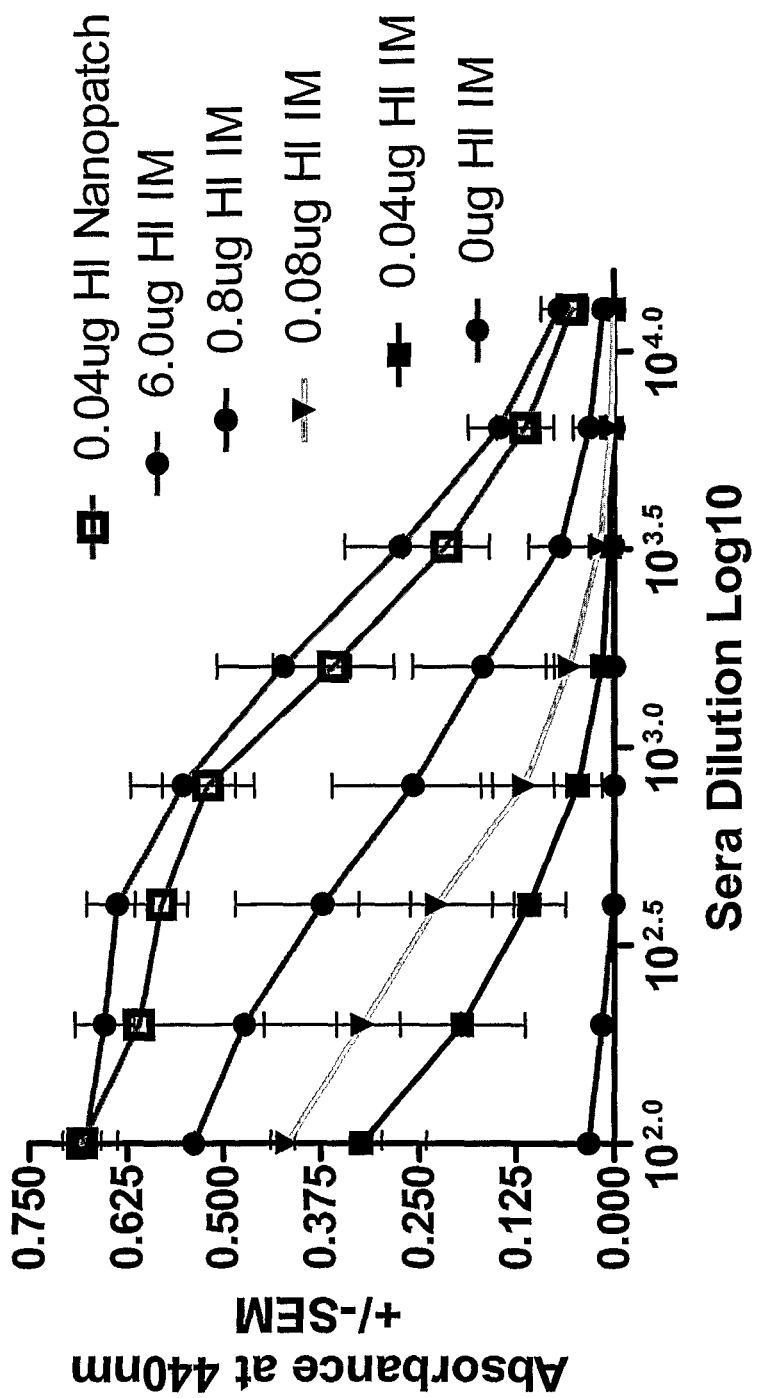
FIG. 19A is a graph showing an example of ELISA antibody reactivity for different intramuscular needle and syringe vaccine doses, and for 0.04 μg vaccine delivered using a patch having projections coated using a gas flow.

Following example 6, with these patch local skin delivery attributes established, the resultant systemic immune responses generated in mice were measured, with the results being shown in FIG. 19A. The patch mice data were compared against needle and syringe intramuscular injection controls. Using needle and syringe (gauge 0.29 needle) intramuscular injection, a range of doses were delivered to the mouse caudal thigh muscle (0 (control), 0.04, 0.08, 0.8, and 6.0 µg corresponding to the total HA as stated by the manufacturer (CSL Ltd, Melbourne, Australia). Mice were bled 63 days after one immunisation.

Firstly, as shown in FIG. 19A, the ELISA antibody reactivity (performed using sera with doubling serial dilutions starting from 1:100 up to 1:12800) was compared for the intramuscular needle and syringe doses compared with 0.04 µg delivered with two patches. The results show patch delivery (0.04 µg) achieves similar antibody levels as generated by 6.0 µg delivered by IM injection.

Notably, it will be appreciated that although this establishes a dose reduction of a factor of 150, it is not specific to vaccination against influenza.

Figures 19B, 19C:
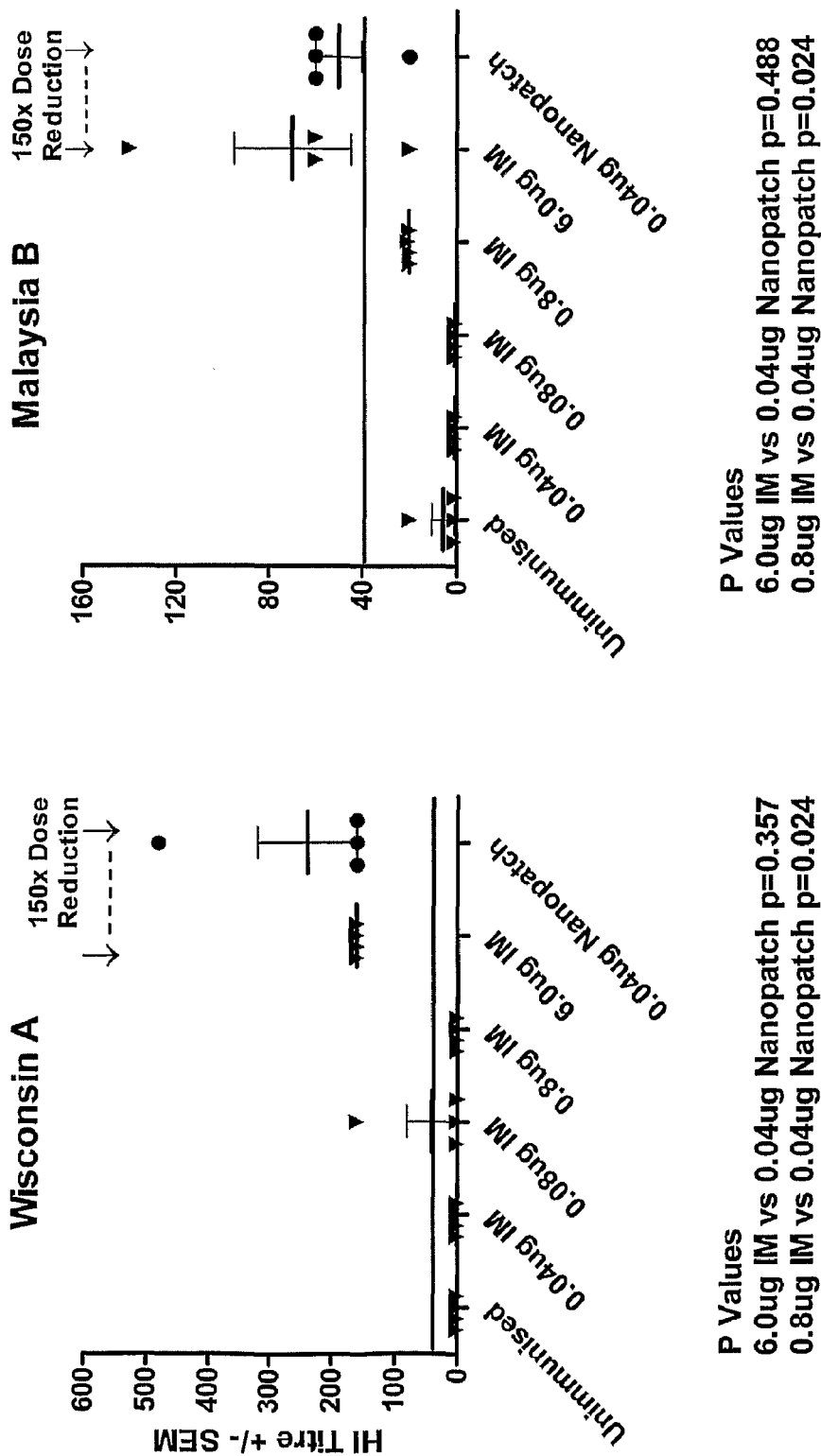
FIGS. 19B-D show graphs of example of Hemagglutinin Inhibition assays (HI) performed for different intramuscular needle and syringe vaccine doses, and for 0.04 ug vaccine delivered using a patch having projections coated using a gas flow for Wisconsin A, Malaysia B, and New Caledonia A.
Figure 19D:
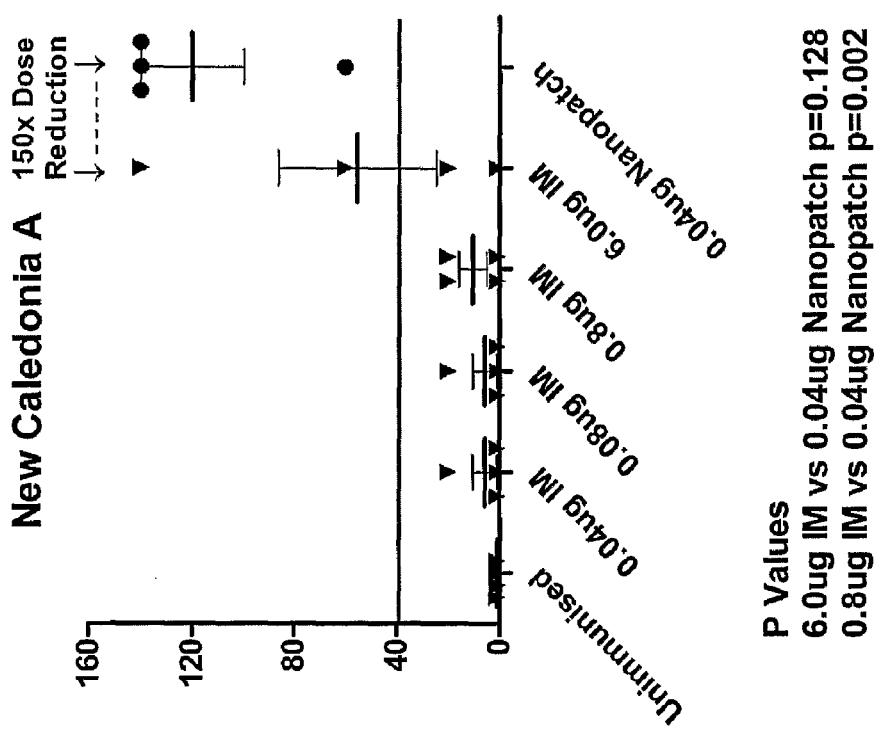

Thus, to measure relative levels of influenza protection, a heamagglutinin inhibition (HI) assay was used on the mice sera samples, with results being shown in FIGS. 19B-D. In particular, Hemagglutinin Inhibition assays (HI), were performed using the sera at different dilutions against each of the virus types (Wisconsin A, Malaysia B, and New Caledonia A).

Clearly, for all three stains of influenza, patch delivery (0.04 µg) achieved HI levels equivalent to those generated by 6.0 µg delivered by IM injection (p=0.357, 0.488 and 0.128 respectively for Wisconsin A, Malaysia B and New Caledonia A). This data shows the patch achieves a surrogate for vaccination protection against the influenza vaccine, with just a 1/150 of the dose delivered with the conventional needle and syringe.

Accordingly, it will be appreciated that dose reductions up to 150× could be achieved when influenza vaccine ((Fluvax 2007®) was delivered directly to the dermis/epidermis of mice using the patch described herein. In this particular example, the patch includes densely packed projections (average 90 µm in length) dry coated with the vaccine. This type of device is ideal for administering influenza vaccine in the case of a pandemic, not only because of the dose reduction achieved but the possibility of mass vaccinations by self administration of the vaccine. Notably, it will be appreciated that the device described can be extended to other types of vaccinations.

Thus, this example illustrates that a patch coated as described above shows may overcome the issues with using syringes and needles to vaccinate. In particular, a conventional influenza vaccine was delivered (Fluvax 2007®) to C57BL/6 mice and the results showed that the patch delivery achieves equivalent immune responses as those induced by injection but with a dose reduced by a factor of 150. Accordingly, the patch as described in this example, can overcome key shortcomings of existing vaccine delivery technologies.

Example 10

Figures 20A, 20B:
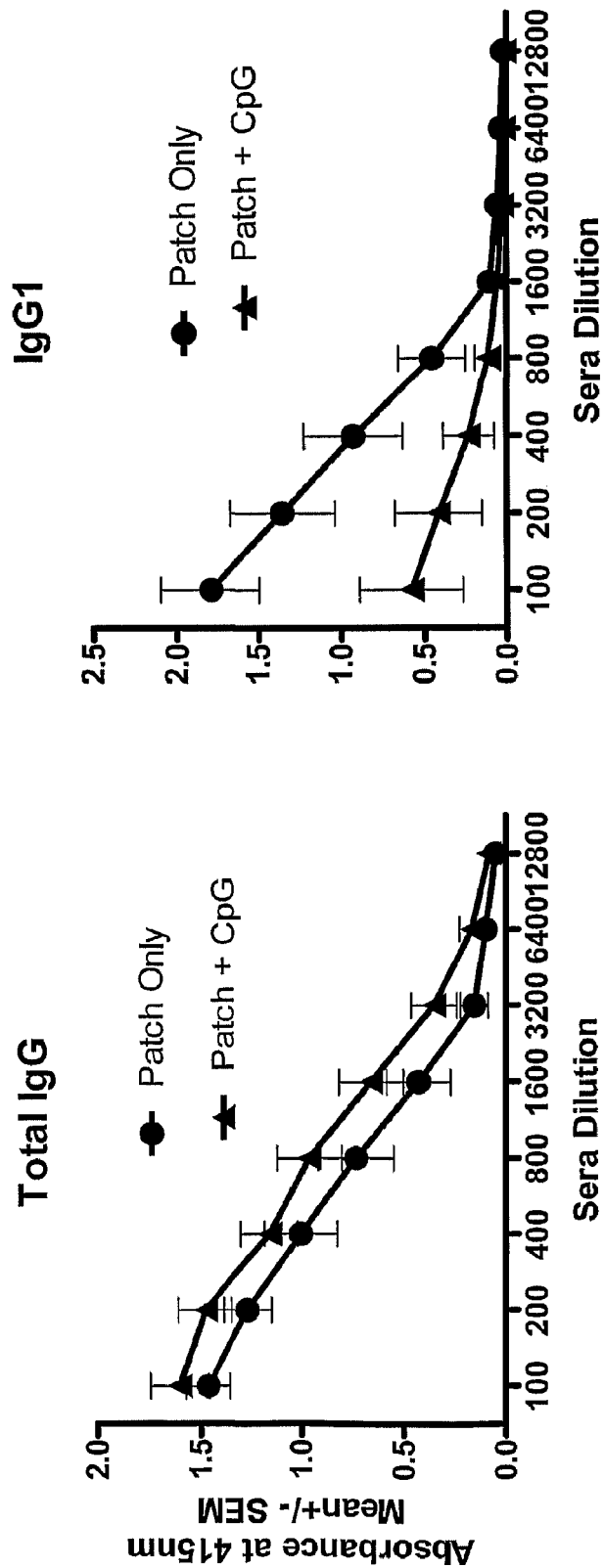
FIGS. 20A-C show graphs of examples of total IgG, IgG1 and IgG2a responses induced by coated nanopatches.
Figure 20C:
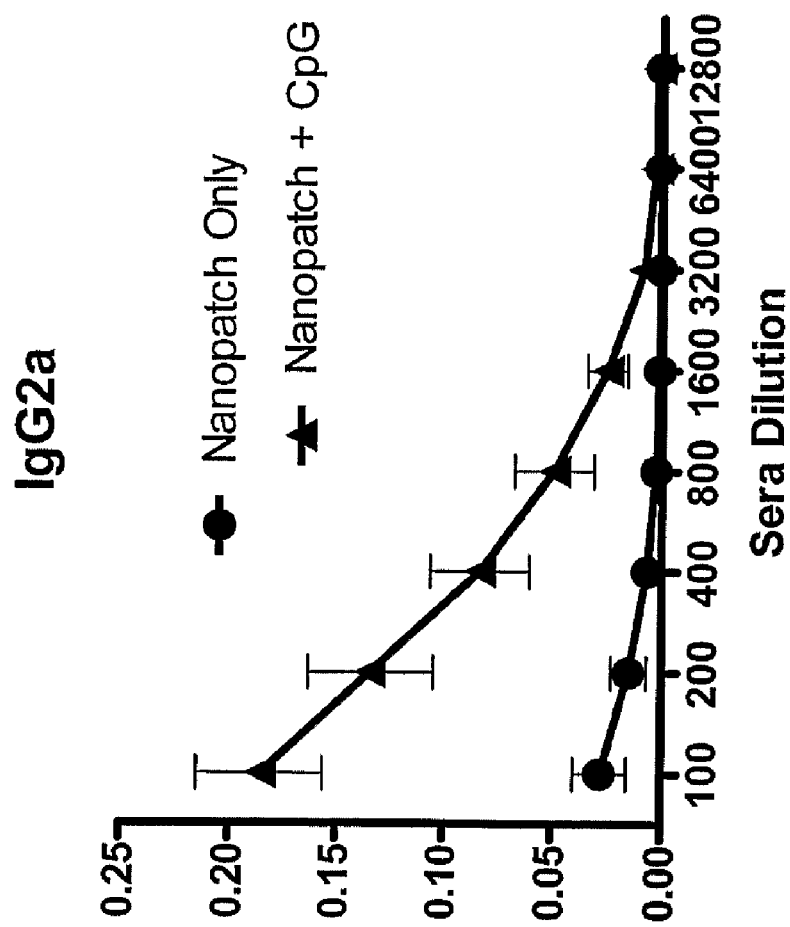

In this example, two groups of 4 C57BL/6 female mice were immunised once with Fluvax coated patch or with Fluvax+CpG (ODN 1826) adjuvant. Mice were bled 2 weeks after one vaccination, and antigen specific total IgG, IgG1 and IgG2a levels were measured using ELISA. The results shown in FIGS. 20A-C demonstrate that a total reversal of IgG1 and IgG2a responses when the adjuvant is included.

Accordingly, this example shows that the Th2 bias (Low antigen specific IgG2a/IgG1 levels) shown by the use of the coated patch could be changed to Th1 type of response, which may increase the CTL activity. This may be important in the case of cross protection to a different strain of the virus.

Example 11

Following the above example, a further example is used to investigate the ability to vaccinate subjects in more detail.

The present example combines patch and gene gun technology into a small scale device by allowing a gene gun to be used in patch application.

Figure 21A:
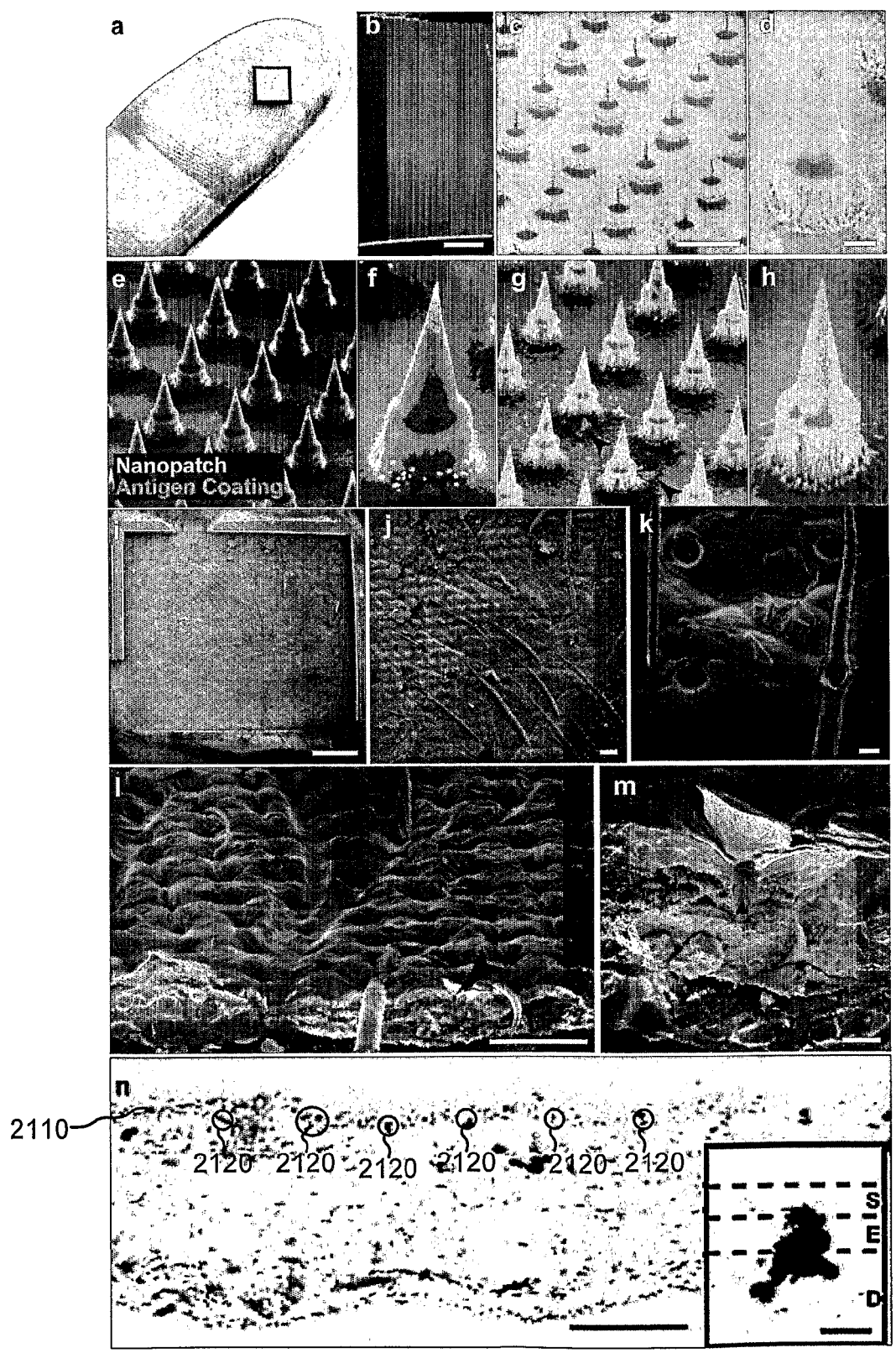
FIG. 21A shows examples of (a) the morphology of a patch, (b)-(d) the projections on the patch, (e)-(f) the patch after being antigen coated, (g)-(h) the coated patch after being applied on mouse ear for antigen delivery, (i)-(m) the penetration of the coated patch on mouse ear skin, and (n) the delivery of coating in the mouse ear skin.

In this example, the patches are created through DRIE and contained 3364 individual projections that are 30 µm wide at the base and between 45 and 130 µm in length as shown in FIGS. 21A(c) and (d). The overall patch dimensions are 5×5 mm, as shown in FIGS. 21A(a) and (b).

The projection spacing are selected to match the distribution and depth of antigen presenting cells of the epidermis. Notably, these patches are not widely spaced and are typically short (<0.5 mm). The patches may also be made by deep reactive ion etching, so that they can be composed of silica and coated with a thin (~100 nm) gold layer.

The patch projections are coated with the above described nitrogen-jet drying method that results in a consistent and robust layer of antigen and/or adjuvant as shown in FIGS. 21A(e) and (f).

It will be appreciated that the gas jet coating method can provide numerous advantages. In one particular example, the method creates a dry-coating formulation that is typically robust enough to use with different antigens and adjuvants. Notably, dip-coating techniques are difficult to use in this instance as the presently described patch has densely packed patch projections, and dip coating followed by air drying often leads to a thick layer of dried material at the base and not the patch projections.

After removal, the coating on the patch projections was removed (g) and (h). During patch application the skin is penetrated (i) to (m) (in (i) to (k) the bars indicate 1.00, 0.10, and 0.01 mm, respectively) by the projections and the strata compressed at the puncture site. The penetration of the skin by the coated patch projections resulted in the delivery of antigens to the epidermis and the upper-dermis ((n), bar is 100 and 10 µm in the panel and inset, respectively).

The coated patch can then be applied with an anchored spring device that drives the patch into the skin at 1.8 m/s, where it can remain for up to 10 minutes. As shown in the SEM images of FIGS. 21A(g) and (h) that the majority of coating is removed from the patch. The arrowheads are identifying corneocytes that have remained with the device. The high magnification image in FIG. 21A(h) illustrates that the majority of the coating has been removed during the application process.

Furthermore, FIGS. 21A(i) to 21A(k) show increased magnification of the ventral side of a mouse ear that was snap frozen during patch application. These cryo-SEM images show the penetration of the individual patch projections into the surface of the skin. The depth of penetration and shape of the skin during patch application can be seen in the cryo-fractured skin photographed at an angle in FIGS. 21A(l) and 21A(m).

In particular, FIG. 21A(m) is a single penetration site with an upturned corneocytes at the top; from this image one can appreciate that the patch can penetrate easily through the epidermis and into the dermis.

Once the patch penetrates the skin, the dried vaccine formulation can release from the patch projections and remain in the skin. This was monitored by having Fluvax® 2007 fluorescently labelled, so that sections of the skin revealed the release pattern of a dry-coated vaccine delivered by the patch. In this example the fluorescent labelling is shown at 2120 in FIG. 21A(n). In this image, the top row of nuclei 2110 highlight the epidermis with the vaccine shown at 2120 being seen through the epidermis and into the dermis.

The inset in FIG. 21A(n) shows an overlay of each deposit site with dotted lines highlighting the strata boundaries (S, stratum corneum; E, epidermis; and D, dermis). In this image this highlights the ability of the patch to deliver antigen to both the epidermis and the upper dermis. One observation from the FIG. 21A(n) is that the deposit of antigen does not appear to retain the cone shape of the patch projection, nor a cylindrical pattern; but rather resembles amorphous diffusion.

The diffusion of fluorescently labelled antigens was observed and analyzed using live confocal microscopy. Thus, a patch coated with fluorescently labeled dextran was applied to freshly excised skin and immediately imaged in 3D every minute for over 15 minutes, with the resulting diffusion of the released material being rendered in 3D and shown in FIG. 21B(a) to (c). These show that within 10 minutes the majority of diffusion had occurred. The data also indicated that the diffusion radius was approximately 1 to 2 cell diameters. This range is useful due to the even distribution of antigen presenting cells in the epidermis.

Figure 21B:
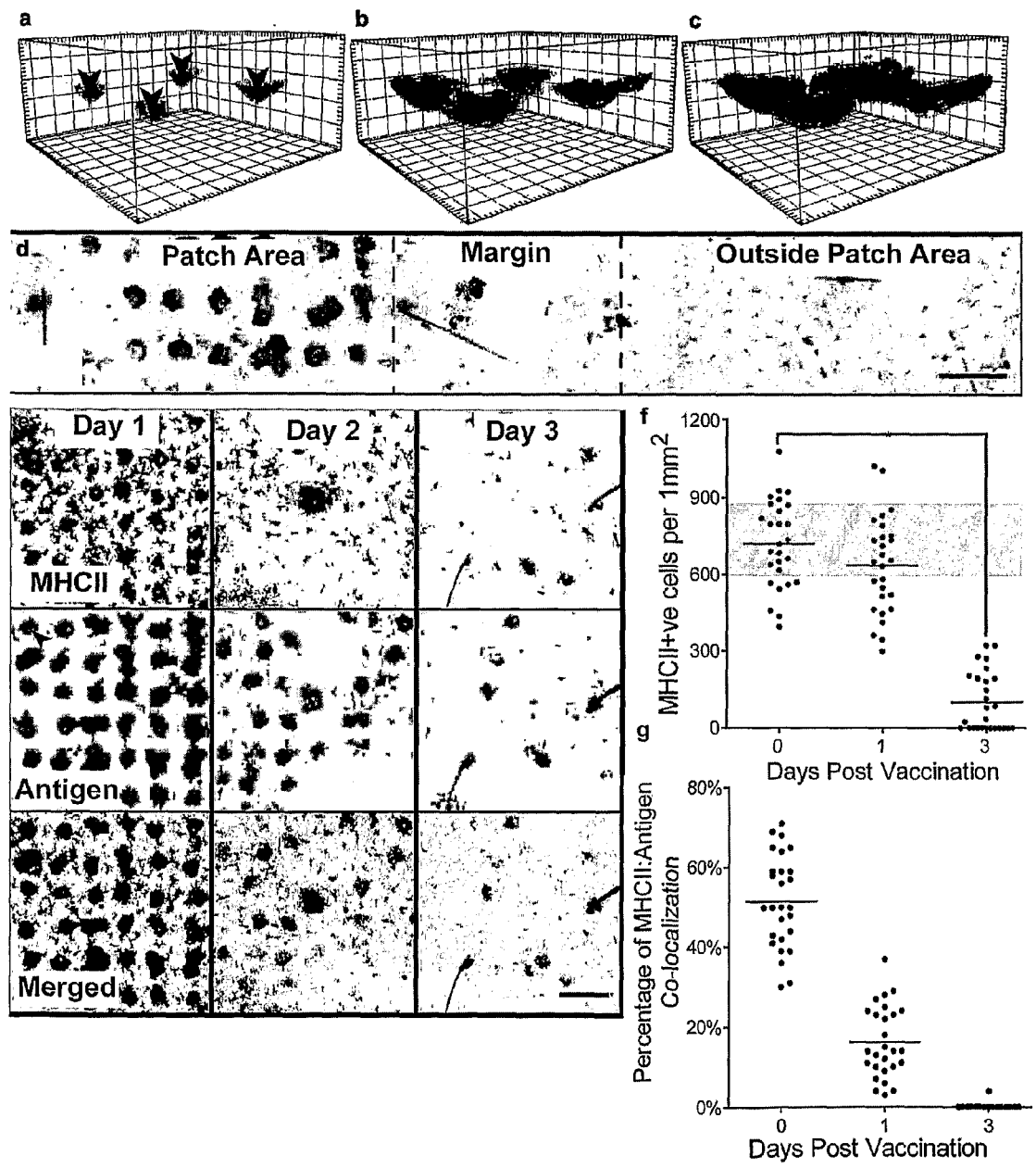
FIG. 21B shows examples of (a)-(c) the delivery of coating in mouse skin and the following diffusion after the coating being delivered in mouse ear skin, and (d)-(g) the migration of cells after the mouse ear being treated by antigen coated nanopatches.

Accordingly, this highlights the ability to deliver antigen directly to antigen presenting cells in the epidermis. Having observed the delivery, release, and diffusion of antigen in the areas where antigen presenting cells were located, it was also noted that three days after the patch delivered antigen to the skin, the antigen presenting cells (MHCII positive) were gone form the patch area but remained outside the patch projection free margin, as shown in FIG. 21B(d). In particular, this shows a series of stitched images from the patch area to the margin and into the untreated region of the skin.

This observation led to further tests with patch delivered ovalbumin (OVA). Quantification of MHCII positive cells over time revealed a rapid decline in the number of epidermal antigen presenting cells within three days, as shown in FIG. 21B(e) and (f). The number of antigen deposit sites was also tallied and showed greater that 86% (or >2800 projections per patch) of the patch projections delivered antigen into the skin.

Notably, one day after patch application the number of MHCII and antigen co-localization dropped more than the number of MHCII cells, as shown in FIGS. 21B(f) and (g).

This implies that those MHCII positive cells that were in contact with the released antigen migrated quicker than those further away. Together these observations may indicate a mechanism through which the patch could deliver antigen directly to cells with MHCII; and those cells could carry the antigen to the lymph nodes for presentation. The number of MHCII positive cells that were exposed to antigen and their migration away from the application area leads to systemic immune response studies to confirm vaccination.

Influenza antigen from the commercially available vaccine, Fluvax® was used for testing the patch delivery device of this example. The coating formulation contained 4 micrograms Hemagglutinin (HA) and 100 micrograms MC per patch. The coated patches are shown in FIGS. 21A(e) and 21A(f). A release assay based on fluorescently labeled Fluvax® showed that this configuration of patch delivered approximately 20 ng HA per device.

Figure 21C:
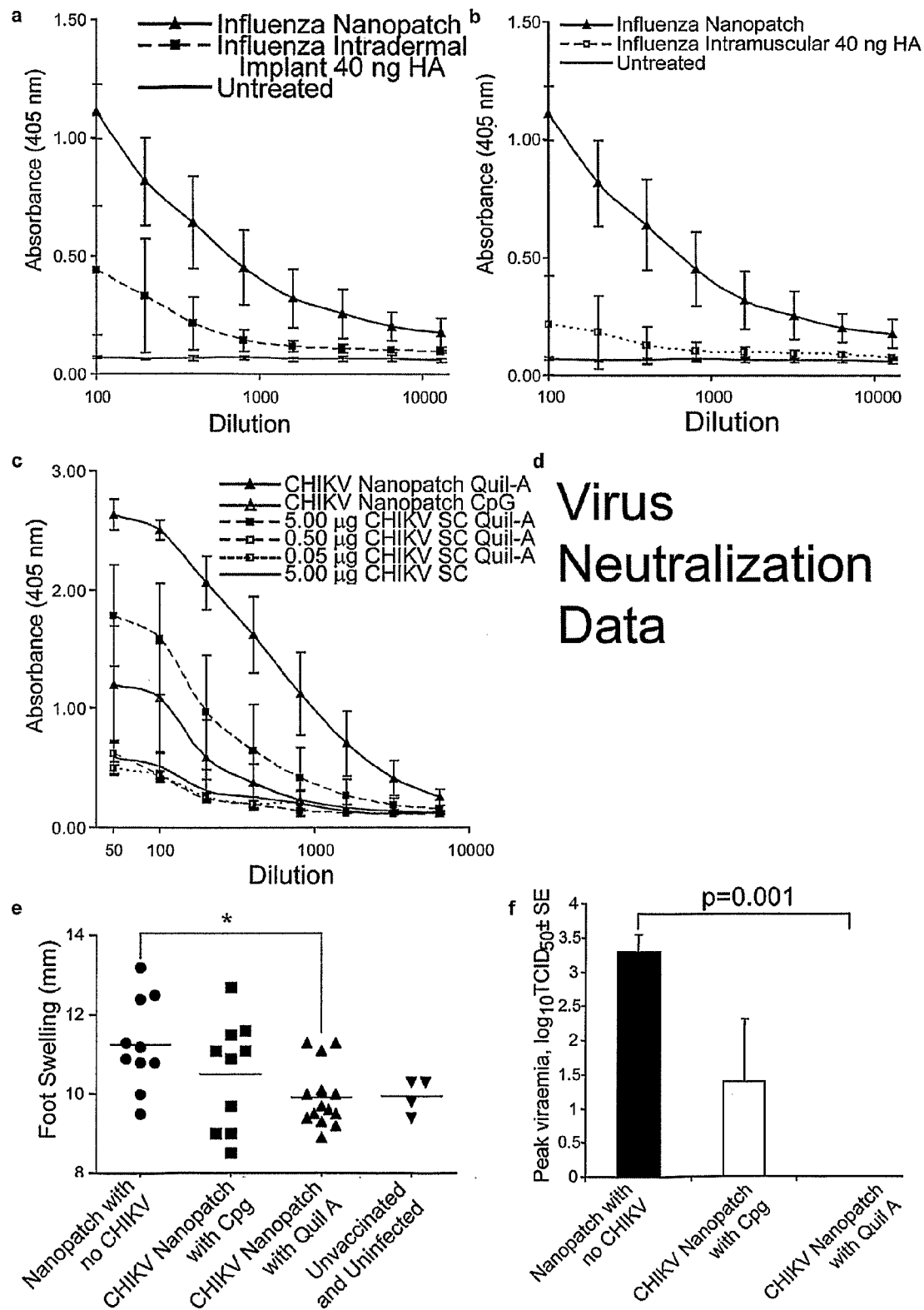
FIG. 21C shows an example of a nanopatch generated immune response and protection from Chikungunya viral challenge; and, FIGS. 22A and 22B show an example of the size distribution of PEI/DNA nanoparticles (N:P ratio of 5:1)

Notably, this small amount of antigen is enough to generate strong IgG production after 14 days (FIG. 21C(a), solid line, solid triangles). For comparison, the antibody response of patch is much greater than that from an implant containing 40 ng HA and 100 microgram MC (FIG. 21C(a), dashed line, solid squares). Unimmunized sera is shown as a solid line in FIGS. 21C(a) to 21C(c).

Immune responses from patch delivered Fluvax® was also compared to intramuscular injection of 0.04 micrograms HA (Fluvax®). However, the 40 ng HA injected dose was weaker than the patch (p=0.008) (FIG. 21C(b)). Thus, it will be appreciated that these data values indicate that patch vaccination can result in a strong immune response with a well known and strong antigen.

According to a further example, the patch technology described herein was tested with an untested antigen from a globally important emerging disease without a commercial antigen. Chikungunya virus antigen was made by irradiating cultured virus from the 2005-2006 Reunion Island out break. The irradiated virus was then coated onto the patch at 5 micrograms killed virus, 100 micrograms MC, and 6 micrograms QA (or 20 micrograms CpG). Only a single patch was applied per animal.

After 14 days a strong immune response could be seen from the group with QA as shown in FIG. 21C(c). The patch-QA response was significantly greater than the subcutaneously injected positive control that contained 5 micrograms killed virus and 6 micrograms QA to p=0.0017. The CpG adjuvant group showed a weaker response than the subcutaneous positive control, but the response was obviously higher than the subcutaneous injected 5 micrograms killed virus with no adjuvant, the negative control. Both the QA and the CpG patch groups elicited immune responses but this positive result did not indicate protection status.

After confirming the antibody response to the patch delivered Chikungunya antigen, it is determined whether or not the patch induced the protection of virus-neutralizing antibodies. The success of immunization depends on the ability of the individual to resist a challenge. Two months after immunization, live Chikungunya virus challenges were carried out. The virus was injected into the feet and this results in foot swelling and viraemia in naive individuals. Mouse models of Chikungunya infection show that the viral replication induces the expression of MCP-1. MCP-1 is a known proinflammatory gene that helps to recruit macrophages and thus the result is inflammation and swelling at the site of alphaviral injection that can be documented by measuring foot swelling. The results indicated that while the patch group with CpG did decrease swelling, only the patch group with QA was statistically significant from the sham immunized group and indistinguishable from the untreated controls.

Notably, foot swelling is a good but rough measure of the inflammatory response. However, the viraemia data shows clear protection from Chikungunya virus challenge in the patch group with QA group. This group showed no appreciable foot swelling nor was there any virus recovered from the sera after challenge. The peak viral titers were found at day 2 which is historically consistent. The sham immunized group had a mean $TCID_{50}$ of $3.3 \log_{10}$ which was much higher than the patch group with CpG as an adjuvant, to $TCID_{50}$ of $1.4 \log_{10}$. The $TCID_{50}$ from the patch group with QA had no detectable viraemia and was significantly different from the sham group, to p=0.001. Thus, it will be appreciated that patch immunization can completely protect from Chikungunya virus challenge.

Accordingly, the above example highlights that dry-coating antigens with or without adjuvant onto patch projections that have been specifically designed to target immune cells of the skin have the capacity to protect against viral infection. The patch is simple to use and quite small compared to a needle and syringe. Thus, it will be appreciated that there is no risk of needle stick injury with this device.

Thus, it will be appreciated that the patch described herein, in one example, can provide technology which has the capacity to effectively deliver antigen directly to antigen presenting cells, thereby eliciting a strong, protective immune response that holds up against challenge.

The coating methodology also developed has worked well with a variety of formulations including Influenza vaccine and killed Chikungunya virus; with and without adjuvants. The antigens were targeted to the immune cells of the skin and MHCII positive cells have been observed migrating in response to patch immunization. This immunization also led to strong and long lasting immunity to Chikungunya virus challenge. Thus, the patch described herein can provide an effective, next generation device for effective immunization.

Accordingly, this highlights that the coated patch provides a vaccine delivery method that is economical and efficient to prevent emerging, endemic, and enzootic diseases before they cause health and economic tragedies.

Example 12

In this example, epidermal targeted transfection with a projection patch dry-coated with DNA containing nanoparticles is performed.

The size distribution of PEI:DNA nanoparticles is shown in FIGS. 22A and 22B. Nanoparticles were produced at a N:P of 5:1 with PEI (25 k linear) and pEGFP DNA in ultra-pure water.

Figure 22C:
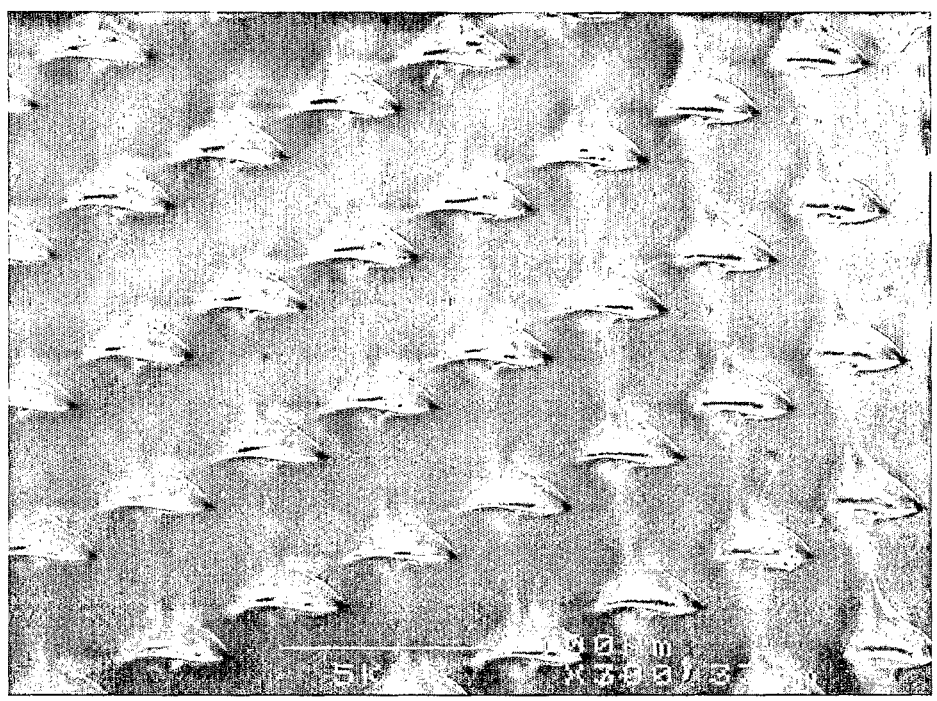
FIGS. 22C and 22D show an example of the coating of polyethylenimine (PEI)/DNA nanoparticles on patch projections before and after use respectively.
Figure 22D:
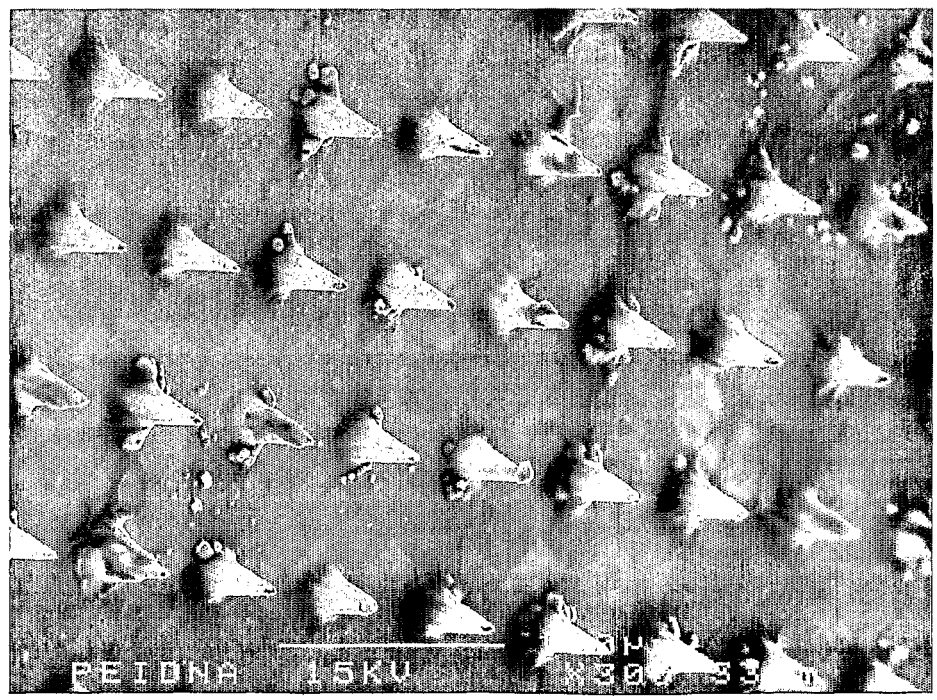

A coating solution containing methylcellulose and PEI/DNA nanoparticles was used to coat projection patches following Example 1. The morphology of the coated patches and the coated patches after being applied on mouse ear for 15 minutes for nanoparticle delivery to the mouse ear skin is shown in FIGS. 22C and 22D, respectively.

Figure 22E:
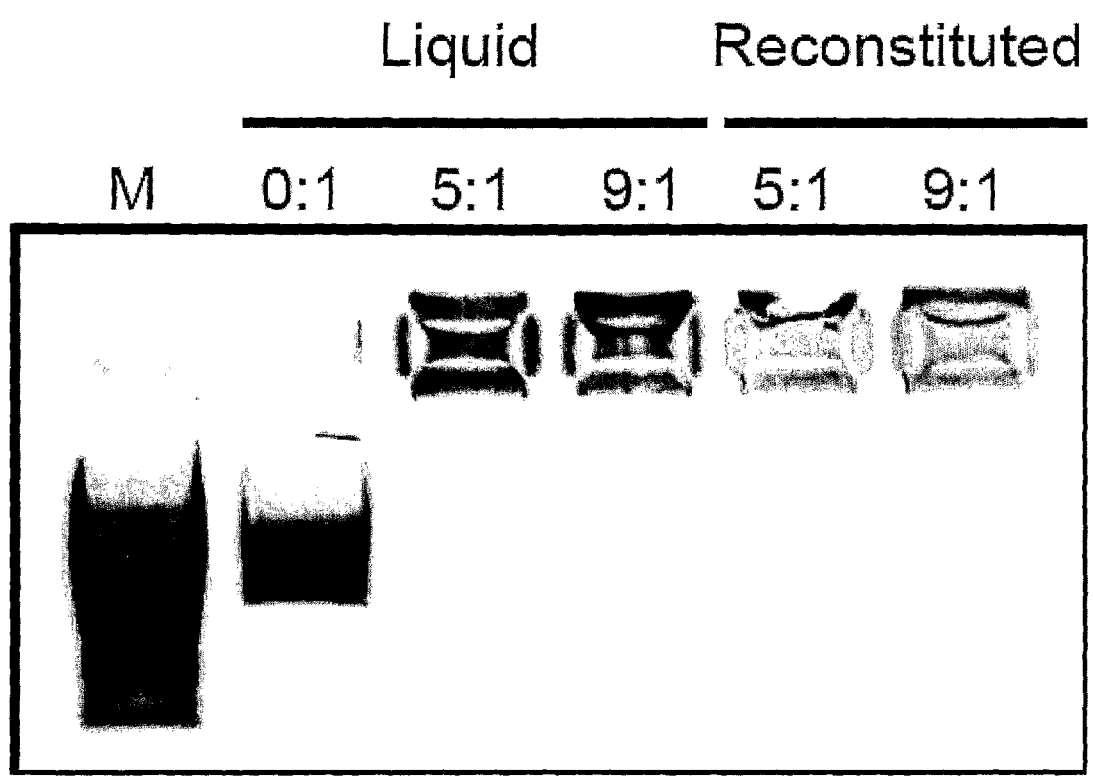
FIG. 22E shows an example agarose gel analysis for original and reconstituted PEI:DNA nanoparticles for a variety of formulations including different N:P ratios (0:1, 5:1, and 9:1); and, FIGS. 22F and 22G are example transfection images obtained using the patch of FIG. 22C.

After dry coating, the coated patches were dipped in water to get reconstituted PEI/DNA nanoparticles. The aim was to confirm that the nanoparticles did not aggregate after coating process. Agarose gel analysis was performed on original and reconstituted PEI:DNA nanoparticles for a variety of formulations including different N:P ratios (0:1, 5:1, and 9:1). The results in FIG. 22E show that dried and reconstituted PEI:DNA nanoparticles still retain their supramolecular structure and do not release free DNA despite a change in size. This is evidenced by positive staining in the well of both reconstituted samples.

Figures 22F, 22G:

Finally, patches coated with PEI/DNA nanoparticles were used to deliver nanoparticles into mouse ear skin for transfection study. The resulting transfection image is shown in FIGS. 22F and 22G. FIG. 22F shows that cells with dendrites can be transfected by PEI/DNA nanoparticles delivered by coated Nanopatches. FIG. 22G shows that the transfection is in the epidermal layer of mouse ear skin.

A number of further variations and options for use with the above described devices will now be described.

Herein, the terms "projection", "micro-nanoprojection", "nanoneedle", "nanoprojection", "needle", "rod" etc are used interchangeably to describe the projections.

A further feature is that the projections may be used for delivery not only through the skin but through other body surfaces, including mucosal surfaces, to cellular sites below the outer layer or layers of such surfaces. The term "internal site", as used herein, is to be understood as indicating a site below the outer layer(s) of skin and other tissues for which the devices of the present invention are to be used.

The device is suitable for intracellular delivery. The device is suitable for delivery to specific organelles within cells. Examples of organelles to which the device can be applied include a cell nucleus, or endoplasmic reticulum, for example.

In one example the device is provided having a needle support section, that is to say the projections comprise a suitable support section, of sufficient length to reach the desired site and a (needle) delivery end section having a length no greater than 20 microns and a maximum width no greater than 5 microns, preferably no greater than 2 microns.

In one example, the maximum width of the delivery end section is no greater than 1000 nm, even more preferably the maximum width of the delivery end section is no greater than 500 nm.

In a further example, the device is for mucosal delivery. This device may have a needle support section, that is to say the projections comprise a suitable support section, of sufficient length to reach the desired site, such as of length at least 100 microns and a (needle) delivery end section having a length no greater than 20 microns and a maximum width no greater than 5 microns, preferably no greater than 2 microns.

In one example, the device of the invention is for delivery to lung, eye, cornea, sclera or other internal organ or tissue. In a further example, the device is for in-vitro delivery to tissue, cell cultures, cell lines, organs, artificial tissues and tissue engineered products. This device typically has a needle support section, that is to say the projections comprise a suitable support section, of length at least 5 microns and a needle delivery end section having a length no greater than 20 microns and a maximum width no greater than 5 microns, preferably no greater than 2 microns.

In one example, the device comprises projections in which the (needle) delivery end section and support length, that is to say the "needle support section", is coated with a bioactive material across the whole or part of its length. The (needle) delivery end section and support length may be coated on selective areas thereof. This may depend upon the bioactive material being used or the target selected for example.

In a further example, a bioactive material is releasably incorporated into the material of which the needle, or projection, is composed. All, or part of the projection may be constructed of a biocompatible, biodegradable polymer (such as Poly Lactic Acid (PLA), PolyGlycolic Acid (PGA) or PGLA or Poly Glucleic Acid), which is formulated with the bioactive material of choice. The projections may then be inserted into the appropriate target site and, as they dissolve, the bioactive material will enter the organelle(s)/cells.

Examples of bioactive materials, which are not intended to be limiting with respect to the invention include polynucleotides and nucleic acid or protein molecules, antigens, allergens, adjuvants, molecules, elements or compounds. In addition, the device may be coated with materials such as biosensors, nanosensors or MEMS.

Illustrative material that can be delivered may include any or more of: small chemical or biochemical compounds including drugs, metabolites, amino acids, sugars, lipids, saponins, and hormones; macromolecules such as complex carbohydrates, phospholipids, peptides, polypeptides, peptidomimetics, and nucleic acids; or other organic (carbon containing) or inorganic molecules; and particulate matter including whole cells, bacteria, viruses, virus-like particles, cell membranes, dendrimers and liposomes.

The material can be selected from nucleic acids, illustrative examples of which include DNA, RNA, sense oligonucleotides, antisense oligonucleotides, ribozymes, small interfering oligonucleotides (siRNAs), micro RNAs (miRNAs), repeat associated RNAs (rasiRNA), effector RNAs (eRNAs), and any other oligonucleotides known in the art, which inhibit transcription and/or translation of a mutated or other detrimental protein. In illustrative examples of this type, the nucleic acid is in the form of an expression vector from which a polynucleotide of interest is expressible. The polynucleotide of interest may encode a polypeptide or an effector nucleic acid molecule such as sense or antisense oligonucleotides, siRNAs, miRNAs and eRNAs.

The material can be selected from peptides or polypeptides, illustrative examples of which include insulin, proinsulin, follicle stimulating hormone, insulin like growthfactor-1, insulin like growth factor-2, platelet derived growth factor, epidermal growth factor, fibroblast growth factors, nerve growth factor, colony stimulating factors, transforming growth factors, tumor necrosis factor, calcitonin, parathyroid hormone, growth hormone, bone morphogenic protein, erythropoietin, hemopoietic growth factors, luteinizing hormone, glucagon, glucagon like peptide-1, anti-angiogenic proteins, clotting factors, anti-clotting factors, atrial natriuretic factor, plasminogen activators, bombesin, thrombin, enkephalinase, vascular endothelial growth factor, interleukins, viral antigens, non-viral antigens, transport proteins, and antibodies.

The material can be selected from receptor ligands. Illustrative examples of receptors include Fc receptor, heparin sulfate receptor, vitronectin receptor, Vcam-1 receptor, hemaglutinin receptor, Pvr receptor, Icam-1 receptor, decay-accelerating protein (CD55) receptor, Car (coxsackievirus-adenovirus) receptor, integrin receptor, sialic acid receptor, HAVCr-1 receptor, low-density lipoprotein receptor, BGP (biliary glycoprotien) receptor, aminopeptidease N receptor, MHC class-1 receptor, laminin receptor, nicotinic acetylcholine receptor, CD56 receptor, nerve growth factor receptor, CD46 receptor, asialoglycoprotein receptor Gp-2, alpha-dystroglycan receptor, galactosylceramide receptor, Cxcr4 receptor, Glvr1 receptor, Ram-1 receptor, Cat receptor, Tva receptor, BLVRcp1 receptor, MHC class-2 receptor, toll-like receptors (such as TLR-1 to -6) and complement receptors.

The material can be selected from antigens including endogenous antigens produced by a host that is the subject of the stimulus or material delivery or exogenous antigens that are foreign to that host. The antigens may be in the form of soluble peptides or polypeptides or polynucleotides from which an expression product (e.g., protein or RNA) is producible. Suitable endogenous antigens include, but are not restricted to, cancer or tumor antigens. Non-limiting examples of cancer or tumor antigens include antigens from a cancer or tumor selected from ABL1 proto-oncogene, AIDS related cancers, acoustic neuroma, acute lymphocytic leukemia, acute myeloid leukemia, adenocystic carcinoma, adrenocortical cancer, agnogenic myeloid metaplasia, alopecia, alveolar soft-part sarcoma, anal cancer, angiosarcoma, aplastic anemia, astrocytoma, ataxia-telangiectasia, basal cell carcinoma (skin), bladder cancer, bone cancers, bowel cancer, brain stem glioma, brain and CNS tumors, breast cancer, CNS tumors, carcinoid tumors, cervical cancer, childhood brain tumors, childhood cancer, childhood leukemia, childhood soft tissue sarcoma, chondrosarcoma, choriocarcinoma, chronic lymphocytic leukemia, chronic myeloid leukemia, colorectal cancers, cutaneous T-cell lymphoma, dermatofibrosarcoma protuberans, desmoplastic small round cell tumor, ductal carcinoma, endocrine cancers, endometrial cancer, ependymoma, oesophageal cancer, Ewing's Sarcoma, Extra-Hepatic Bile Duct Cancer, Eye Cancer, Eye: Melanoma, Retinoblastoma, Fallopian Tube cancer, Fanconi anemia, fibrosarcoma, gall bladder cancer, gastric cancer, gastrointestinal cancers, gastrointestinal-carcinoid-tumor, genitourinary cancers, germ cell tumors, gestational-trophoblastic-disease, glioma, gynecological cancers, haematological malignancies, hairy cell leukemia, head and neck cancer, hepatocellular cancer, hereditary breast cancer, histiocytosis, Hodgkin's disease, human papillomavirus, hydatidiform mole, hypercalcemia, hypopharynx cancer, intraocular melanoma, islet cell cancer, Kaposi's sarcoma, kidney cancer, Langerhan's cell histiocytosis, laryngeal cancer, leiomyosarcoma, leukemia, Li-Fraumeni syndrome, lip cancer, liposarcoma, liver cancer, lung cancer, lymphedema, lymphoma, Hodgkin's lymphoma, non-Hodgkin's lymphoma, male breast cancer, malignant-rhabdoid tumor of kidney, medulloblastoma, melanoma, Merkel cell cancer, mesothelioma, metastatic cancer, mouth cancer, multiple endocrine neoplasia, mycosis fungoides, myelodysplastic syndromes, myeloma, myeloproliferative disorders, nasal cancer, nasopharyngeal cancer, nephroblastoma, neuroblastoma, neurofibromatosis, Nijmegen breakage syndrome, non-melanoma skin cancer, non-small-cell-lung-cancer (NSCLC), ocular cancers, esophageal cancer, oral cavity cancer, oropharynx cancer, osteosarcoma, ostomy ovarian cancer, pancreas cancer, paranasal cancer, parathyroid cancer, parotid gland cancer, penile cancer, peripheral-neuroectodermal tumours, pituitary cancer, polycythemia vera, prostate cancer, rare cancers and associated disorders, renal cell carcinoma, retinoblastoma, rhabdomyosarcoma, Rothmund-Thomson syndrome, salivary gland cancer, sarcoma, schwannoma, Sezary syndrome, skin cancer, small cell lung cancer (SCLC), small intestine cancer, soft tissue sarcoma, spinal cord tumors, squamous-cell-carcinoma-(skin), stomach cancer, synovial sarcoma, testicular cancer, thymus cancer, thyroid cancer, transitional-cell-cancer-(bladder), transitional-cell-cancer-(renal-pelvis-/-ureter), trophoblastic cancer, urethral cancer, urinary system cancer, uroplakins, uterine sarcoma, uterus cancer, vaginal cancer, vulva cancer, Waldenstrom's macroglobulinemia, Wilms' tumor. In certain examples, the cancer or tumor relates to melanoma. Illustrative examples of melanoma-related antigens include melanocyte differentiation antigen (e.g., gp100, MART, Melan-A/MART-1, TRP-1, Tyros, TRP2, MC1R, MUC1F, MUC1R or a combination thereof) and melanoma-specific antigens (e.g., BAGE, GAGE-1, gp100In4, MAGE-1 (e.g., GenBank Accession No. X54156 and AA494311), MAGE-3, MAGE4, PRAME, TRP2IN2, NYNSO1a, NYNSO1b, LAGE1, p97 melanoma antigen (e.g., GenBank Accession No. M12154) p5 protein, gp75, oncofetal antigen, GM2 and GD2 gangliosides, cdc27, p21ras, gp100$^{Pmel117}$ or a combination thereof. Other tumour-specific antigens include, but are not limited to: etv6, aml1, cyclophilin b (acute lymphoblastic leukemia); Ig-idiotype (B cell lymphoma); E-cadherin, α-catenin, β-catenin, γ-catenin, p120ctn (glioma); p21ras (bladder cancer); p21ras (biliary cancer); MUC family, HER2/neu, c-erbB-2 (breast cancer); p53, p21ras (cervical carcinoma); p21ras, HER2/neu, c-erbB-2, MUC family, Cripto-1protein, Pim-1 protein (colon carcinoma); Colorectal associated antigen (CRC)-CO17-1A/GA733, APC (colorectal cancer); carcinoembryonic antigen (CEA) (colorectal cancer; choriocarcinoma); cyclophilin b (epithelial cell cancer); HER2/neu, c-erbB-2, ga733 glycoprotein (gastric cancer); α-fetoprotein (hepatocellular cancer); Imp-1, EBNA-1 (Hodgkin's lymphoma); CEA, MAGE-3, NY-ESO-1 (lung cancer); cyclophilin b (lymphoid cell-derived leukemia); MUC family, p21ras (myeloma); HER2/neu, c-erbB-2 (non-small cell lung carcinoma); Imp-1, EBNA-1 (nasopharyngeal cancer); MUC family, HER2/neu, c-erbB-2, MAGE-A4, NY-ESO-1 (ovarian cancer); Prostate Specific Antigen (PSA) and its antigenic epitopes PSA-1, PSA-2, and PSA-3, PSMA, HER2/neu, c-erbB-2, ga733 glycoprotein (prostate cancer); HER2/neu, c-erbB-2 (renal cancer); viral products such as human papillomavirus proteins (squamous cell cancers of the cervix and esophagus); NY-ESO-1 (testicular cancer); and HTLV-1 epitopes (T cell leukemia).

Foreign antigens are suitably selected from transplantation antigens, allergens as well as antigens from pathogenic organisms. Transplantation antigens can be derived from donor cells or tissues from e.g., heart, lung, liver, pancreas, kidney, neural graft components, or from the donor antigen-presenting cells bearing MHC loaded with self antigen in the absence of exogenous antigen.

Non-limiting examples of allergens include Fel d 1 (i.e., the feline skin and salivary gland allergen of the domestic cat *Felis domesticus*, the amino acid sequence of which is disclosed International Publication WO 91/06571), Der p I, Der p II, Der fI or Der fII (i.e., the major protein allergens from the house dust mite *dermatophagoides*, the amino acid sequence of which is disclosed in International Publication WO 94/24281). Other allergens may be derived, for example from the following: grass, tree and weed (including ragweed) pollens; fungi and moulds; foods such as fish, shellfish, crab, lobster, peanuts, nuts, wheat gluten, eggs and milk; stinging insects such as bee, wasp, and hornet and the chirnomidae (non-biting midges); other insects such as the housefly, fruitfly, sheep blow fly, screw worm fly, grain weevil, silkworm, honeybee, non-biting midge larvae, bee moth larvae, mealworm, cockroach and larvae of *Tenibrio molitor* beetle; spiders and mites, including the house dust mite; allergens found in the dander, urine, saliva, blood or other bodily fluid of mammals such as cat, dog, cow, pig, sheep, horse, rabbit, rat, guinea pig, mouse and gerbil; airborne particulates in general; latex; and protein surfactant additives.

The material can be pathogenic organisms such as, but are not limited to, viruses, bacteria, fungi parasites, algae and protozoa and amoebae. Illustrative viruses include viruses responsible for diseases including, but not limited to, measles, mumps, rubella, poliomyelitis, hepatitis A, B (e.g., GenBank Accession No. E02707), and C (e.g., GenBank Accession No. E06890), as well as other hepatitis viruses, influenza, adenovirus (e.g., types 4 and 7), rabies (e.g., GenBank Accession No. M34678), yellow fever, Epstein-Barr virus and other herpesviruses such as papillomavirus, Ebola virus, influenza virus, Japanese encephalitis (e.g., GenBank Accession No. E07883), dengue (e.g., GenBank Accession No. M24444), hantavirus, Sendai virus, respiratory syncytial virus, othromyxoviruses, vesicular stomatitis virus, visna virus, cytomegalovirus and human immunodeficiency virus (HIV) (e.g., GenBank Accession No. U18552). Any suitable antigen derived from such viruses are useful in the practice of the present invention. For example, illustrative retroviral antigens derived from HIV include, but are not limited to, antigens such as gene products of the gag, poi, and env genes, the Nef protein, reverse transcriptase, and other HIV components. Illustrative examples of hepatitis viral antigens include, but are not limited to, antigens such as the S, M, and L proteins of hepatitis B virus, the pre-S antigen of hepatitis B virus, and other hepatitis, e.g., hepatitis A, B, and C, viral components such as hepatitis C viral RNA. Illustrative examples of influenza viral antigens include; but are not limited to, antigens such as hemagglutinin and neurarninidase and other influenza viral components. Illustrative examples of measles viral antigens include, but are not limited to, antigens such as the measles virus fusion protein and other measles virus components. Illustrative examples of rubella viral antigens include, but are not limited to, antigens such as proteins E1 and E2 and other rubella virus components; rotaviral antigens such as VP7sc and other rotaviral components. Illustrative examples of cytomegaloviral antigens include, but are not limited to, antigens such as envelope glycoprotein B and other cytomegaloviral antigen components. Non-limiting examples of respiratory syncytial viral antigens include antigens such as the RSV fusion protein, the M2 protein and other respiratory syncytial viral antigen components. Illustrative examples of herpes simplex viral antigens include, but are not limited to, antigens such as immediate early proteins, glycoprotein D, and other herpes simplex viral antigen components. Non-limiting examples of varicella zoster viral antigens include antigens such as 9PI, gpII, and other varicella zoster viral antigen components. Non-limiting examples of Japanese encephalitis viral antigens include antigens such as proteins E, M-E, M-E-NS 1, NS 1, NS 1-NS2A, 80% E, and other Japanese encephalitis viral antigen components. Representative examples of rabies viral antigens include, but are not limited to, antigens such as rabies glycoprotein, rabies nucleoprotein and other rabies viral antigen components. Illustrative examples of papillomavirus antigens include, but are not limited to, the L1 and L2 capsid proteins as well as the E6/E7 antigens associated with cervical cancers, See Fundamental Virology, Second Edition, eds. Fields, B. N. and Knipe, D. M., 1991, Raven Press, New York, for additional examples of viral antigens.

Illustrative examples of fungi include *Acremonium* spp., *Aspergillus* spp., *Basidiobolus* spp., *Bipolaris* spp., *Blastomyces dermatidis*, *Candida* spp., *Cladophialophora carrionii*, *Coccoidiodes immitis*, *Conidiobolus* spp., *Cryptococcus* spp., *Curvularia* spp., *Epidermophyton* spp., *Exophiala jeanselmei*, *Exserohilum* spp., *Fonsecaea compacta*, *Fonsecaea pedrosoi*, *Fusarium oxysporum*, *Fusarium solani*, *Geotrichum candidum*, *Histoplasma capsulatum* var. *capsulatum*, *Histoplasma capsulatum* var. *duboisii*, *Hortaea werneckii*, *Lacazia loboi*, *Lasiodiplodia theobromae*, *Leptosphaeria senegalensis*, *Madurella grisea*, *Madurella mycetomatis*, *Malassezia furfur*, *Microsporum* spp., *Neotestudina rosatii*, *Onychocola canadensis*, *Paracoccidioides brasiliensis*, *Phialophora verrucosa*, *Piedraia hortae*, *Piedra iahortae*, *Pityriasis versicolor*, *Pseudallesheria boydii*, *Pyrenochaeta romeroi*, *Rhizopus arrhizus*, *Scopulariopsis brevicaulis*, *Scytalidium dimidiatum*, *Sporothrix schenckii*, *Trichophyton* spp., *Trichosporon* spp., *Zygomcete fungi*, *Absidia corymbifera*, *Rhizomucor pusillus* and *Rhizopus arrhizus*. Thus, representative fungal antigens that can be used in the compositions and methods of the present invention include, but are not limited to, candida fungal antigen components; *histoplasma* fungal antigens such as heat shock protein 60 (HSP60) and other *histoplasma* fungal antigen components; cryptococcal fungal antigens such as capsular polysaccharides and other cryptococcal fungal antigen components; *coccidiodes* fungal antigens such as spherule antigens and other *coccidiodes* fungal antigen components; and *tinea* fungal antigens such as trichophytin and other *coccidiodes* fungal antigen components.

Illustrative examples of bacteria include bacteria that are responsible for diseases including, but not restricted to, diphtheria (e.g., *Corynebacterium diphtheria*), pertussis (e.g., *Bordetella pertussis*, GenBank Accession No. M35274), tetanus (e.g., *Clostridium tetani*, GenBank Accession No. M64353), tuberculosis (e.g., *Mycobacterium tuberculosis*), bacterial pneumonias (e.g., *Haemophilus influenzae*.), cholera (e.g., *Vibrio cholerae*), anthrax (e.g., *Bacillus anthracis*), typhoid, plague, shigellosis (e.g., *Shigella dysenteriae*), botulism (e.g., *Clostridium botulinum*), salmonellosis (e.g., GenBank Accession No. L03833), peptic ulcers (e.g., *Helicobacter pylori*), Legionnaire's Disease, Lyme disease (e.g., GenBank Accession No. U59487), Other pathogenic bacteria include *Escherichia coli*, *Clostridium perfringens*, *Pseudomonas aeruginosa*, *Staphylococcus aureus* and *Streptococcus pyogenes*. Thus, bacterial antigens which can be used in the compositions and methods of the invention include, but are not limited to: pertussis bacterial antigens such as pertussis toxin, filamentous hemagglutinin, pertactin, F M2, FIM3, adenylate cyclase and other pertussis bacterial antigen components; diphtheria bacterial antigens such as diphtheria toxin or toxoid and other diphtheria bacterial antigen components; tetanus bacterial antigens such as tetanus toxin or toxoid and other tetanus bacterial antigen components, streptococcal bacterial antigens such as M proteins and other streptococcal bacterial antigen components; gram-negative bacilli bacterial antigens such as lipopolysaccharides and other gram-negative bacterial antigen components; *Mycobacterium tuberculosis* bacterial antigens such as mycolic acid, heat shock protein 65 (HSP65), the kDa major secreted protein, antigen 85A and other mycobacterial antigen components; *Helicobacter pylori* bacterial antigen components, pneumococcal bacterial antigens such as pneumolysin, pneumococcal capsular polysaccharides and other pnermiococcal bacterial antigen components; *Haemophilus influenza* bacterial antigens such as capsular polysaccharides and other *Haemophilus influenza* bacterial antigen components; anthrax bacterial antigens such as anthrax protective antigen and other anthrax bacterial antigen components; rickettsiae bacterial antigens such as rompA and other rickettsiae bacterial antigen component. Also included with the bacterial antigens described herein are any other bacterial, mycobacterial, mycoplasmal, rickettsial, or chlamydial antigens.

Illustrative examples of protozoa include protozoa that are responsible for diseases including, but not limited to, malaria (e.g., GenBank Accession No. X53832), hookworm, onchocerciasis (e.g., GenBank Accession No. M27807), schistosomiasis (e.g., GenBank Accession No. LOS 198), toxoplasmosis, trypanosomiasis, leishmaniasis, giardiasis (GenBank Accession No. M33641), amoebiasis, filariasis (e.g., GenBank Accession No. J03266), borreliosis, and trichinosis. Thus, protozoal antigens which can be used in the compositions and methods of the invention include, but are not limited to: *plasmodium falciparum* antigens such as merozoite surface antigens, sporozoite surface antigens, circumsporozoite antigens, gametocyte/gamete surface antigens, blood-stage antigen pf 155/RESA and other plasmodial antigen components; *toxoplasma* antigens such as SAG-1, p30 and other *toxoplasma*) antigen components; schistosomae antigens such as glutathione-S-transferase, paramyosin, and other schistosomal antigen components; *leishmania major* and other leishmaniae antigens such as gp63, lipophosphoglycan and its associated protein and other leishmanial antigen components; and *trypanosoma cruzi* antigens such as the 75-77 kDa antigen, the 56 kDa antigen and other trypanosomal antigen components.

The material can be toxin components acting as antigens. Illustrative examples of toxins include, but are not restricted to, staphylococcal enterotoxins, toxic shock syndrome toxin; retroviral antigens (e.g., antigens derived from HIV), streptococcal antigens, staphylococcal enterotoxin-A (SEA), staphylococcal enterotoxin-B (SEB), staphylococcal enterotoxin$_{1-3}$ (SE$_{1-3}$), staphylococcal enterotoxin-D (SED), staphylococcal enterotoxin-E (SEE) as well as toxins derived from mycoplasma, *mycobacterium*, and herpes viruses.

In specific examples, the antigen is delivered to antigen-presenting cells. Such antigen-presenting cells include professional or facultative antigen-presenting cells. Professional antigen-presenting cells function physiologically to present antigen in a form that is recognised by specific T cell receptors so as to stimulate or anergise a T lymphocyte or B lymphocyte mediated immune response. Professional antigen-presenting cells not only process and present antigens in the context of the major histocompatability complex (MHC), but also possess the additional immunoregulatory molecules required to complete T cell activation or induce a tolerogenic response. Professional antigen-presenting cells include, but are not limited to, macrophages, monocytes, B lymphocytes, cells of myeloid lineage, including monocytic-granulocytic-DC precursors, marginal zone Kupffer cells, microglia, T cells, Langerhans cells and dendritic cells including interdigitating dendritic cells and follicular dendritic cells. Non-professional or facultative antigen-presenting cells typically lack one or more of the immunoregulatory molecules required to complete T lymphocyte activation or anergy. Examples of non-professional or facultative antigen-presenting cells include, but are not limited to, activated T lymphocytes, eosinophils, keratinocytes, astrocytes, follicular cells, microglial cells, thymic cortical cells, endothelial cells, Schwann cells, retinal pigment epithelial cells, myoblasts, vascular smooth muscle cells, chondrocytes, enterocytes, thymocytes, kidney tubule cells and fibroblasts. In some examples, the antigen-presenting cell is selected from monocytes, macrophages, B lymphocytes, cells of myeloid lineage, dendritic cells or Langerhans cells. In certain advantageous examples, the antigen-presenting cell expresses CD11c and includes a dendritic cell or Langerhans cell. In some examples the antigen-presenting cell stimulates an immune response. In other examples, the antigen-presenting cell induces a tolerogenic response.

The delivery of exogenous antigen to an antigen-presenting cell can be enhanced by methods known to practitioners in the art. For example, several different strategies have been developed for delivery of exogenous antigen to the endogenous processing pathway of antigen-presenting cells, especially dendritic cells. These methods include insertion of antigen into pH-sensitive liposomes (Zhou and Huang, 1994, *Immunomethods*, 4:229-235), osmotic lysis of pinosomes after pinocytic uptake of soluble antigen (Moore et al., 1988, *Cell*, 54:777-785), coupling of antigens to potent adjuvants (Aichele et al., 1990, *J. Exp. Med.*, 171: 1815-1820; Gao et al., 1991, *J. Immunol.*, 147: 3268-3273; Schulz et al., 1991, *Proc. Natl. Acad. Sci. USA*, 88: 991-993; Kuzu et al., 1993, *Euro. J. Immunol.*, 23: 1397-1400; and Jondal et al., 1996, *Immunity* 5: 295-302) and apoptotic cell delivery of antigen (Albert et al. 1998, *Nature* 392:86-89; Albert et al. 1998, *Nature Med.* 4:1321-1324; and in International Publications WO 99/42564 and WO 01/85207). Recombinant bacteria (eg. *E. coli*) or transfected host mammalian cells may be pulsed onto dendritic cells (as particulate antigen, or apoptotic bodies respectively) for antigen delivery. Recombinant chimeric virus-like particles (VLPs) have also been used as vehicles for delivery of exogenous heterologous antigen to the MHC class I processing pathway of a dendritic cell line (Bachmann et al., 1996, *Eur. J. Immunol.*, 26(11): 2595-2600).

Alternatively, or in addition, an antigen may be linked to, or otherwise associated with, a cytolysin to enhance the transfer of the antigen into the cytosol of an antigen-presenting cell of the invention for delivery to the MHC class I pathway. Exemplary cytolysins include saponin compounds such as saponin-containing Immune Stimulating Complexes (ISCOMs) (see e.g., Cox and Coulter, 1997, *Vaccine* 15(3): 248-256 and U.S. Pat. No. 6,352,697), phospholipases (see, e.g., Camilli et al., 1991, *J. Exp. Med.* 173: 751-754), pore-forming toxins (e.g., an α-toxin), natural cytolysins of gram-positive bacteria, such as listeriolysin O (LLO, e.g., Mengaud et al., 1988, *Infect. Immun.* 56: 766-772 and Portnoy et al., 1992, *Infect. Immun.* 60: 2710-2717), streptolysin O (SLO, e.g., Palmer et al., 1998, *Biochemistry* 37(8): 2378-2383) and perfringolysin O (PFO, e.g., Rossjohn et al., *Cell* 89(5): 685-692). Where the antigen-presenting cell is phagosomal, acid activated cytolysins may be advantageously used. For example, listeriolysin exhibits greater pore-forming ability at mildly acidic pH (the pH conditions within the phagosome), thereby facilitating delivery of vacuole (including phagosome and endosome) contents to the cytoplasm (see, e.g., Portnoy et al., *Infect. Immun.* 1992, 60: 2710-2717).

The cytolysin may be provided together with a pre-selected antigen in the form of a single composition or may be provided as a separate composition, for contacting the antigen-presenting cells. In one example, the cytolysin is fused or otherwise linked to the antigen, wherein the fusion or linkage permits the delivery of the antigen to the cytosol of the target cell. In another example, the cytolysin and antigen are provided in the form of a delivery vehicle such as, but not limited to, a liposome or a microbial delivery vehicle selected from virus, bacterium, or yeast. Suitably, when the delivery vehicle is a microbial delivery vehicle, the delivery vehicle is non-virulent. In a preferred example of this type, the delivery vehicle is a non-virulent bacterium, as for example described by Portnoy et al. in U.S. Pat. No. 6,287,556, comprising a first polynucleotide encoding a non-secreted functional cytolysin operably linked to a regulatory polynucleotide which expresses the cytolysin in the bacterium, and a second polynucleotide encoding one or more pre-selected antigens. Non-secreted cytolysins may be provided by various mechanisms, e.g., absence of a functional signal sequence, a secretion incompetent microbe, such as microbes having genetic lesions (e.g., a functional signal sequence mutation), or poisoned microbes, etc. A wide variety of nonvirulent, non-pathogenic bacteria may be used; preferred microbes are relatively well characterised strains, particularly laboratory strains of *E. coli*, such as MC4100, MC1061, DH5α, etc. Other bacteria that can be engineered for the invention include well-characterised, nonvirulent, non-pathogenic strains of *Listeria monocytogenes, Shigella flexneri, mycobacterium, Salmonella, Bacillus subtilis*, etc. In a particular example, the bacteria are attenuated to be non-replicative, non-integrative into the host cell genome, and/or non-motile inter- or intra-cellularly.

The coated patches described above can be used to deliver one or more antigens to virtually any antigen-presenting cell capable of endocytosis of the subject vehicle, including phagocytic and non-phagocytic antigen-presenting cells. In examples when the delivery vehicle is a microbe, the subject methods generally require microbial uptake by the target cell and subsequent lysis within the antigen-presenting cell vacuole (including phagosomes and endosomes).

In other examples, the antigen is produced inside the antigen-presenting cell by introduction of a suitable expression vector as for example described above. The antigen-encoding portion of the expression vector may comprise a naturally-occurring sequence or a variant thereof, which has been engineered using recombinant techniques. In one example of a variant, the codon composition of an antigen-encoding polynucleotide is modified to permit enhanced expression of the antigen in a target cell or tissue of choice using methods as set forth in detail in International Publications WO 99/02694 and WO 00/42215. Briefly, these methods are based on the observation that translational efficiencies of different codons vary between different cells or tissues and that these differences can be exploited, together with codon composition of a gene, to regulate expression of a protein in a particular cell or tissue type. Thus, for the construction of codon-optimised polynucleotides, at least one existing codon of a parent polynucleotide is replaced with a synonymous codon that has a higher translational efficiency in a target cell or tissue than the existing codon it replaces. Although it is preferable to replace all the existing codons of a parent nucleic acid molecule with synonymous codons which have that higher translational efficiency, this is not necessary because increased expression can be accomplished even with partial replacement. Suitably, the replacement step affects 5, 10, 15, 20, 25, 30%, more preferably 35, 40, 50, 60, 70% or more of the existing codons of a parent polynucleotide.

The expression vector for introduction into the antigen-presenting cell will be compatible therewith such that the antigen-encoding polynucleotide is expressible by the cell. For example, expression vectors of this type can be derived from viral DNA sequences including, but not limited to, adenovirus, adeno-associated viruses, herpes-simplex viruses and retroviruses such as B, C, and D retroviruses as well as spumaviruses and modified lentiviruses. Suitable expression vectors for transfection of animal cells are described, for example, by Wu and Ataai (2000, *Curr. Opin. Biotechnol.* 11(2):205-208), Vigna and Naldini (2000, *J. Gene Med.* 2(5): 308-316), Kay, et al. (2001, *Nat. Med.* 7(0:33-40), Athanasopoulos, et al. (2000, *Int. J. Mol. Med.* 6(4):363-375) and Walther and Stein (2000, *Drugs* 60(2):249-271).

In one aspect, the device is provided in the form of a patch containing a plurality of needles (projections) for application to a body surface. A multiplicity of projections can allow multiple cells and organelles to be targeted and provided with a material at the same time. The patch may be of any suitable shape, such as square or round for example. The overall number of projections per patch depends upon the particular application in which the device is to be used. Preferably, the patch has at least 10 needles per mm, and more preferably at least 100 needles per mm$^2$. Considerations and specific examples of such a patch are provided in more detail below.

Examples of specific manufacturing steps used to fabricate the device are described in greater detail below. In one preferred aspect, the device of the invention is constructed from biocompatible materials such as Titanium, Gold, Silver or Silicon, for example. This may be the entire device, or alternatively it may only be the projections or the delivery end section of the projections which are made from the biocompatible materials.

One manufacturing method for the device utilises the Deep Reactive Ion Etching (DRIE) of the patterns direct from silicon wafers, see the construction section below.

Another manufacturing method for the device utilises manufacturing from a male template constructed with X-ray lithography, electrodeposition and moulding (LIGA). The templates are then multiply inserted into a soft polymer to produce a plurality of masks. The masks are then vacuum deposited/sputtered with the material of choice for the nano-projections, such as titanium, gold, silver, or tungsten. Magnetron sputtering may also be applied, see the construction section below.

An alternative means for producing masks is with 2 photon Stereolithography, a technique which is known in the art and is described in more detail below.

In one example, the device is constructed of silicon.

The device may be for a single use or may be used and then recoated with the same or a different bioactive material or other stimulus, for example.

In one example, the device comprises projections which are of differing lengths and/or diameters (or thicknesses depending on the shape of the projections) to allow targeting of different targets within the same use of the device.

Persons skilled in the art will appreciate that numerous variations and modifications will become apparent. All such variations and modifications which become apparent to persons skilled in the art, should be considered to fall within the spirit and scope that the invention broadly appearing before described.

The claims defining the invention are as follows:

1. A method of coating a material onto projections provided on a patch, wherein the method includes:
    a) applying a coating solution containing the material to at least the projections; and,
    b) using a gas flow to i) distribute the applied coating solution over the projections; and ii) dry the coating solution.

2. A method according to claim 1, wherein the material includes at least one of:
    a) nanoparticles;
    b) a nucleic acid or protein;
    c) an antigen, allergen, or adjuvant;
    d) parasites, bacteria, viruses, or virus-like particles;
    e) quantum dots, SERS tags, Raman tags or other nanobiosensors;
    f) metals or metallic compounds; and,
    g) molecules, elements or compounds.

3. A method according to claim 1, wherein the coating solution includes a therapeutic agent.

4. A method according to claim 3, wherein the therapeutic agent is at least one of:
    a) DNA; and,
    b) protein.

5. A method according to claim 1, wherein the coating solution includes at least one of:
    a) a viscosity enhancer;
    b) a surfactant; and,
    c) an adjuvant.

6. A method according to claim 5, wherein at least one of:
    a) the viscosity enhancer is 0% to 90% of the coating solution; and,
    b) the surfactant is 0% to 90% of the coating solution.

7. A method according to claim 5, wherein the viscosity enhancer is at least one of methylcellulose (MC), carboxymethylcellulose (CMC), gelatin, agar, and agarose.

8. A method according to claim 1, wherein the coating solution has a viscosity of between $10^{-3}$ Pa·S and 1 Pa·S.

9. A method according to claim 8, wherein the coating solution has a viscosity of 0.01-0.06 Pa·S.

10. A method according to claim 1, wherein the coating solution has a surface tension of between 0.023 N/m and 0.073 N/m.

11. A method according to claim 10, wherein the coating solution has a surface tension of 0.03-0.04 N/m.

12. A method according to claim 1, wherein the gas flow is induced at least in part by extracting gas from a container containing the patch.

13. A method according to claim 1, wherein the patch has a surface area of approximately 0.16 cm$^2$.

14. A method according to claim 1, wherein the projections have a length of between 10 to 400 µm.

15. A method according to claim 14, wherein the projections have a length of 90 µm.

16. A method according to claim 1, wherein the projections have a radius of curvature of greater than 1 µm.

17. A method according to claim 16, wherein the projections have a radius of curvature greater than 5 µm.

18. A method according to claim 1, wherein the projections include a support section and a targeting section.

19. A method according to claim 1, wherein the projections are solid.

20. A method according to claim 1, wherein the projections are non-porous and non-hollow.

21. A method according to claim 1, wherein the patch is at least one of:
a) hydrophobic; and,
b) hydrophilic.

22. A method according to claim 1, wherein the applied coating solution is evenly distributed over the projections using the gas flow.

23. A method according to claim 1, wherein using the gas flow to distribute the applied coating solution causes the projections to be completely wetted by the coating solution.

24. A method according to claim 1, wherein the method includes providing the gas flow using a gas jet directed towards the patch.

25. A method according to claim 24, wherein the method includes using the gas jet to evenly disperse the coating solution over the projections.

26. A method according to claim 24, wherein the gas flow is provided at a gas flow rate using the gas jet, the distribution of the applied coating solution over the projections being controlled, at least in part, by selecting the gas flow rate.

27. A method according to claim 24, wherein the method includes using multiple gas jets to distribute and dry the coating solution.

* * * * *